United States Patent
De Taboada et al.

(10) Patent No.: US 12,427,335 B2
(45) Date of Patent: Sep. 30, 2025

(54) APPARATUS AND METHOD FOR IRRADIATING A SURFACE WITH LIGHT

(71) Applicant: Pthera LLC, Newark, DE (US)

(72) Inventors: Luis De Taboada, Carlsbad, CA (US);
Jackson Streeter, Newberry, FL (US);
Scott Bradley, San Marcos, CA (US);
Scott Delapp, San Diego, CA (US);
Terry McNeill, Ramona, CA (US)

(73) Assignee: Pthera LLC, Newark, DE (US)

( * ) Notice: Subject to any disclaimer, the term of this patent is extended or adjusted under 35 U.S.C. 154(b) by 270 days.

(21) Appl. No.: 17/572,186

(22) Filed: Jan. 10, 2022

(65) Prior Publication Data

US 2022/0126114 A1 Apr. 28, 2022

Related U.S. Application Data

(63) Continuation of application No. 16/445,661, filed on Jun. 19, 2019, now Pat. No. 11,219,782, which is a
(Continued)

(51) Int. Cl.
*A61N 5/06* (2006.01)
*A61B 17/00* (2006.01)
(Continued)

(52) U.S. Cl.
CPC ......... *A61N 5/0618* (2013.01); *A61N 5/0617* (2013.01); *A61N 5/0622* (2013.01);
(Continued)

(58) Field of Classification Search
CPC ........ A61B 18/20; A61B 18/203; A61N 5/06; A61N 5/0616
See application file for complete search history.

(56) References Cited

U.S. PATENT DOCUMENTS 3,735,755 A 5/1973 Eggleton et al.
3,810,367 A 5/1974 Peterson
(Continued)

FOREIGN PATENT DOCUMENTS

DE 3200584 7/1983
DE 4108328 9/1992
(Continued)

OTHER PUBLICATIONS

U.S. Appl. No. 10/723,171, filed Nov. 26, 2003, Streeter.
(Continued)

*Primary Examiner* — Lynsey C Eiseman
(74) *Attorney, Agent, or Firm* — Fish & Richardson P.C.

(57) ABSTRACT

An apparatus and method is provided for irradiating a portion of a patient's scalp with light. The apparatus includes a source of light including one or more wavelengths in a range of about 630 nanometers to about 1064 nanometers. The apparatus further includes an output optical element in optical communication with the source. The output optical element includes an emission surface configured to emit a light beam having a cross-sectional area greater than about 2 cm$^2$ at the emission surface of the output optical element and having a time-averaged irradiance in a range of about 10 mW/cm$^2$ to about 10 W/cm$^2$ across the cross-sectional area. The apparatus further includes a thermally conductive portion configured to be placed in thermal communication with the irradiated portion of the patient's scalp and to remove heat from the irradiated portion of the patient's scalp at a rate in a range of about 0.1 Watt to about 5 Watts.

5 Claims, 38 Drawing Sheets

Related U.S. Application Data continuation of application No. 12/389,294, filed on Feb. 19, 2009, now Pat. No. 10,357,662.

(51) Int. Cl.
*A61N 5/00* (2006.01)
*A61N 5/067* (2006.01)

(52) U.S. Cl.
CPC ............... *A61B 2017/00084* (2013.01); *A61N 2005/007* (2013.01); *A61N 5/0616* (2013.01); *A61N 2005/0629* (2013.01); *A61N 2005/063* (2013.01); *A61N 2005/0644* (2013.01); *A61N 2005/0647* (2013.01); *A61N 2005/0659* (2013.01); *A61N 5/067* (2021.08)

(56) References Cited

U.S. PATENT DOCUMENTS

| | | |
|---|---|---|
| 4,315,514 A | 2/1982 | Drewes et al. |
| 4,343,301 A | 8/1982 | Indech |
| 4,630,273 A | 12/1986 | Inoue et al. |
| 4,633,872 A | 1/1987 | Chaffee et al. |
| 4,669,466 A | 6/1987 | L'Esperance |
| 4,671,285 A | 6/1987 | Walker |
| 4,798,215 A | 1/1989 | Turner |
| 4,846,196 A | 7/1989 | Wiksell et al. |
| 4,850,351 A | 7/1989 | Herman et al. |
| 4,930,504 A | 6/1990 | Diamantopoulos et al. |
| 4,951,482 A | 8/1990 | Gilbert |
| 4,951,653 A | 8/1990 | Fry et al. |
| 4,966,144 A | 10/1990 | Rochkind et al. |
| 5,029,581 A | 7/1991 | Kaga et al. |
| 5,037,374 A | 8/1991 | Carol |
| 5,047,006 A | 9/1991 | Brandston et al. |
| 5,054,470 A | 10/1991 | Fry et al. |
| 5,150,704 A | 9/1992 | Tatebayashi et al. |
| 5,259,380 A | 11/1993 | Mendes et al. |
| 5,267,294 A | 11/1993 | Kuroda et al. |
| 5,282,797 A | 2/1994 | Chess |
| 5,344,418 A * | 9/1994 | Ghaffari ............... A61B 18/203 606/9 |
| 5,358,503 A | 10/1994 | Bertwell et al. |
| 5,368,555 A | 11/1994 | Sussman et al. |
| 5,401,270 A | 3/1995 | Muller et al. |
| 5,441,495 A | 8/1995 | Liboff et al. |
| 5,445,146 A | 8/1995 | Bellinger |
| 5,445,608 A | 8/1995 | Chen et al. |
| 5,464,436 A | 11/1995 | Smith |
| 5,474,528 A | 12/1995 | Meserol |
| 5,501,655 A | 3/1996 | Rolt |
| 5,511,563 A | 4/1996 | Diamond |
| 5,540,737 A | 7/1996 | Fenn |
| 5,580,550 A | 12/1996 | Gough et al. |
| 5,580,555 A | 12/1996 | Schwartz |
| 5,601,526 A | 2/1997 | Chapelon et al. |
| 5,616,140 A | 4/1997 | Prescott |
| 5,617,258 A | 4/1997 | Negus et al. |
| 5,621,091 A | 4/1997 | Kunkel et al. |
| 5,622,168 A | 4/1997 | Keusch et al. |
| 5,627,870 A | 5/1997 | Kopecky |
| 5,640,978 A | 6/1997 | Wong |
| 5,643,334 A | 7/1997 | Eckhouse et al. |
| 5,728,090 A | 3/1998 | Martin et al. |
| 5,755,752 A | 5/1998 | Segal |
| 5,762,867 A | 6/1998 | D'Silva |
| 5,817,008 A | 10/1998 | Rafert et al. |
| 5,842,477 A | 12/1998 | Naughton et al. |
| 5,843,073 A | 12/1998 | Sinofsky |
| 5,849,585 A | 12/1998 | Mather et al. |
| 5,871,521 A | 2/1999 | Kaneda et al. |
| 5,879,376 A | 3/1999 | Miller |
| 5,902,741 A | 5/1999 | Purchio et al. |
| 5,928,207 A | 7/1999 | Pisano et al. |
| 5,928,945 A | 7/1999 | Seliktar et al. |
| 5,954,762 A | 9/1999 | Di Mino et al. |
| 5,958,761 A | 9/1999 | Yogev et al. |
| 5,983,141 A | 11/1999 | Sluijter et al. |
| 5,989,245 A | 11/1999 | Prescott |
| 6,030,767 A | 2/2000 | Wagner et al. |
| 6,033,431 A | 3/2000 | Segal |
| 6,042,531 A | 3/2000 | Holcomb |
| 6,045,575 A | 4/2000 | Rosen et al. |
| 6,046,046 A | 4/2000 | Hassanein |
| 6,060,306 A | 5/2000 | Flatt et al. |
| 6,063,108 A | 5/2000 | Salansky et al. |
| 6,100,290 A | 8/2000 | Levy et al. |
| 6,107,325 A | 8/2000 | Chan et al. |
| 6,107,608 A | 8/2000 | Hayes |
| 6,112,110 A | 8/2000 | Wilk |
| 6,117,128 A | 9/2000 | Gregory |
| 6,129,748 A | 10/2000 | Kamei |
| 6,143,878 A | 11/2000 | Koopman et al. |
| 6,146,410 A | 11/2000 | Nagypal et al. |
| 6,149,679 A | 11/2000 | Di Mino et al. |
| 6,156,028 A | 12/2000 | Prescott |
| 6,162,211 A * | 12/2000 | Tankovich ........... A61B 18/203 606/9 |
| 6,179,771 B1 | 1/2001 | Mueller |
| 6,179,830 B1 | 1/2001 | Kokubu |
| 6,187,210 B1 | 2/2001 | Lebouitz et al. |
| 6,198,958 B1 | 3/2001 | Ives et al. |
| 6,210,317 B1 | 4/2001 | Bonlie |
| 6,210,425 B1 | 4/2001 | Chen |
| 6,214,035 B1 | 4/2001 | Streeter |
| 6,221,095 B1 | 4/2001 | Van Zuylen et al. |
| 6,267,780 B1 | 7/2001 | Streeter |
| 6,273,885 B1 | 8/2001 | Koop et al. |
| 6,273,905 B1 | 8/2001 | Streeter |
| 6,277,974 B1 | 8/2001 | Lo et al. |
| 6,290,713 B1 | 9/2001 | Russell |
| 6,290,714 B1 | 9/2001 | Streeter |
| 6,306,130 B1 | 10/2001 | Anderson et al. |
| 6,312,451 B1 | 11/2001 | Streeter |
| 6,344,050 B1 | 2/2002 | Chen |
| 6,358,272 B1 | 3/2002 | Wilden |
| 6,363,285 B1 | 3/2002 | Wey |
| 6,364,907 B1 | 4/2002 | Obochi et al. |
| 6,379,295 B1 | 4/2002 | Woo |
| 6,395,016 B1 | 5/2002 | Oron et al. |
| 6,397,107 B1 | 5/2002 | Lee et al. |
| 6,402,678 B1 | 6/2002 | Fischell et al. |
| 6,421,562 B1 | 7/2002 | Ross |
| 6,443,974 B1 | 9/2002 | Oron et al. |
| 6,443,978 B1 | 9/2002 | Zharov |
| 6,447,537 B1 | 9/2002 | Hartman |
| 6,471,716 B1 | 10/2002 | Pecukonis |
| 6,494,900 B1 | 12/2002 | Salansky et al. |
| 6,514,220 B2 | 2/2003 | Melton, Jr. et al. |
| 6,537,301 B1 | 3/2003 | Kamei |
| 6,537,304 B1 | 3/2003 | Oron |
| 6,551,308 B1 | 4/2003 | Muller et al. |
| 6,571,735 B1 | 6/2003 | Wilkinson |
| 6,602,274 B1 | 8/2003 | Chen |
| 6,663,659 B2 | 12/2003 | McDaniel |
| 6,689,062 B1 | 2/2004 | Mesallum |
| 6,743,222 B2 | 6/2004 | Durkin et al. |
| 6,758,845 B1 | 7/2004 | Weckwerth et al. |
| 6,899,723 B2 | 5/2005 | Chen |
| 6,918,922 B2 | 7/2005 | Oron |
| 6,974,224 B2 | 12/2005 | Thomas-Benedict |
| 7,041,094 B2 | 5/2006 | Connors et al. |
| 7,118,563 B2 | 10/2006 | Weckwerth et al. |
| 7,192,279 B2 | 3/2007 | Rogovsky |
| 7,303,578 B2 | 12/2007 | De Taboada et al. |
| 7,344,555 B2 | 3/2008 | Anders et al. |
| 7,351,253 B2 | 4/2008 | DiMauro et al. |
| 7,534,255 B1 | 5/2009 | Streeter et al. |
| 7,559,945 B2 | 7/2009 | Breden et al. |
| 7,848,035 B2 | 12/2010 | DeLapp et al. |
| 10,357,662 B2 | 7/2019 | De Taboada et al. |
| 11,218,782 B2 | 1/2022 | Taboada et al. |
| 2001/0044623 A1 | 11/2001 | Chen |
| 2002/0029071 A1 | 3/2002 | Whitehurst |

(56) References Cited

U.S. PATENT DOCUMENTS

| | | |
|---|---|---|
| 2002/0068927 A1 | 6/2002 | Prescot |
| 2002/0087205 A1 | 7/2002 | Chen |
| 2002/0123781 A1 | 9/2002 | Shanks et al. |
| 2002/0156371 A1 | 10/2002 | Hedlund et al. |
| 2002/0161418 A1 | 10/2002 | Wilkens et al. |
| 2002/0173780 A1* | 11/2002 | Altshuler ............ A61B 18/203 606/90 |
| 2002/0188334 A1 | 12/2002 | Calgren |
| 2002/0198575 A1 | 12/2002 | Sullivan |
| 2003/0004556 A1 | 1/2003 | McDaniel |
| 2003/0021124 A1 | 1/2003 | Elbrecht et al. |
| 2003/0109906 A1 | 6/2003 | Streeter |
| 2003/0125782 A1 | 7/2003 | Streeter |
| 2003/0125783 A1 | 7/2003 | Moran |
| 2003/0144712 A1 | 7/2003 | Streeter |
| 2003/0167080 A1 | 9/2003 | Hart et al. |
| 2003/0212442 A1 | 11/2003 | Streeter |
| 2003/0216797 A1 | 11/2003 | Oron |
| 2004/0014199 A1 | 1/2004 | Streeter |
| 2004/0015214 A1 | 1/2004 | Simkin et al. |
| 2004/0030325 A1 | 2/2004 | Cahir et al. |
| 2004/0044384 A1 | 3/2004 | Leber et al. |
| 2004/0073278 A1 | 4/2004 | Pachys |
| 2004/0093042 A1 | 5/2004 | Altshuler et al. |
| 2004/0132002 A1 | 7/2004 | Steeter |
| 2004/0138727 A1* | 7/2004 | Taboada ............ A61N 5/0613 607/88 |
| 2004/0143248 A1 | 7/2004 | Marchitlo |
| 2004/0153130 A1 | 8/2004 | Oron et al. |
| 2004/0153131 A1 | 8/2004 | Yorke |
| 2004/0176823 A1* | 9/2004 | Island ............ A61N 5/0616 607/88 |
| 2004/0220513 A1 | 11/2004 | Streeter |
| 2004/0260367 A1 | 12/2004 | De Taboada et al. |
| 2005/0009161 A1 | 1/2005 | Streeter |
| 2005/0024853 A1 | 2/2005 | Thomas-Benedict |
| 2005/0107851 A1 | 5/2005 | De Taboada et al. |
| 2005/0143792 A1 | 6/2005 | Jay |
| 2005/0154382 A1* | 7/2005 | Altshuler ............ A61B 18/203 606/9 |
| 2005/0159793 A1 | 7/2005 | Streeter |
| 2005/0187595 A1 | 8/2005 | Streeter |
| 2005/0203595 A1 | 9/2005 | Oron |
| 2006/0149343 A1* | 7/2006 | Altshuler ............ A61B 18/203 607/90 |
| 2007/0142881 A1 | 6/2007 | Hennings |
| 2007/0179482 A1* | 8/2007 | Anderson ............ A61B 18/203 606/2 |
| 2007/0179570 A1 | 8/2007 | De Taboada et al. |
| 2007/0179571 A1 | 8/2007 | De Taboada et al. |
| 2007/0198004 A1 | 8/2007 | Altschuler et al. |
| 2007/0213791 A1* | 9/2007 | Van Hal ............ A61B 18/203 607/88 |
| 2007/0255359 A1 | 11/2007 | Neev |
| 2008/0172047 A1* | 7/2008 | Altshuler ............ A61H 39/002 606/9 |
| 2010/0211136 A1 | 8/2010 | De Taboada et al. |
| 2019/0351252 A1 | 11/2019 | Taboada et al. |

FOREIGN PATENT DOCUMENTS

| | | |
|---|---|---|
| DE | 4213053 | 10/1993 |
| DE | 29515096 | 1/1996 |
| EP | 0130950 | 4/1990 |
| EP | 1226787 | 7/1992 |
| EP | 0763371 | 3/1997 |
| EP | 0783904 | 7/1997 |
| EP | 0827716 | 3/1998 |
| EP | 1074275 | 2/2001 |
| EP | 2082696 | 7/2009 |
| JP | 04023634 | 2/1992 |
| WO | WO 92/03964 | 3/1992 |
| WO | WO 96/36397 | 11/1996 |
| WO | WO 96/36396 | 1/1997 |
| WO | WO 98/04321 | 2/1998 |
| WO | WO 98/22573 | 5/1998 |
| WO | WO 98/33556 | 8/1998 |
| WO | WO 99/16369 | 4/1999 |
| WO | WO 99/42178 | 8/1999 |
| WO | WO 99/46005 | 9/1999 |
| WO | WO 99/62599 | 12/1999 |
| WO | WO 00/25684 | 5/2000 |
| WO | WO 00/35534 | 6/2000 |
| WO | WO 01/30296 | 5/2001 |
| WO | WO 02/055149 | 7/2002 |
| WO | WO 02/092509 | 11/2002 |
| WO | WO 02/098509 | 12/2002 |
| WO | WO 05/025672 | 3/2005 |
| WO | WO 06/115761 | 11/2006 |
| WO | WO 06/138659 | 12/2006 |
| WO | WO 08/049905 | 5/2008 |

OTHER PUBLICATIONS

Accelrys, "Optical Absorption Spectra of Melanins—A Comparison of Theoretical and Experimental Results," Chemicals Case Study, upon information and belief, available no later than Feb. 19, 2009, retrieved from URL <http://docplayer.net/30389381-Optical-absorption-spectra-of-melanins-a-comparison-of-theoretical-and-experimental-results.html>, 5 pages.

Agov, B. S., et al., "On the mechanism of therapeutic action of helium-neon laser in ischemic heart disease", KUN MED (Mose), pp. 102-105, 1985.

Arvidsson, Andreas, et al., "Neuronal replacement from endogenous precursors in the adult rat brain after stroke", Nature Medicine, vol. 8, No. 9, Sep. 2002, pp. 963-970.

Asahi, Minoru, et al., Expression of Interleukin B Converting Enzyme Gene Family and bc1-2 Gene Family in the Rat Brain Following Permanent Occlusion of the Middle Cerebral Artery, Journal of Cerebral Blood Flow & Metabolism, vol. 17, No. 1, Jan. 1997, 12 pages.

Assia, E. et al., "Temporal Parameters of Low Energy Laser Irradiation for Optimal Delay of Post-Traumatic Degeneration of Rat Optic Nerve", Brain Research, vol. 476, 1989, pp. 205-212.

Basford, Jeffrey R., M.D., Ph.D., "Lasers in Orthopedic Surgery—Laser Therapy: Scientific Basis and Clinical Role", May 1993, vol. 16, No. 5, pp. 541-547.

Belevich et al., "Exploring the proton pump mechanism of cytochrome c oxidase in real time," PNAS, Feb. 2007, 104(8):2685-2690.

Belevich et al., "Proton-coupled electron transfer drives the proton pump of cytochrome c oxidase," Nature, Apr. 2006, 440:829-832.

Belkin, M. et al., "A Critical Review of Low Energy Laser Bioeffects", Lasers and Light in Ophthalmology, vol. 2, No. 1, pp. 63-71, 1988.

Bevilacqua et al., "In Vivo Local Determination of Tissue Optical Properties: Applications to the Human Brain," Applied Optics, vol. 28, No. 22, Aug. 1, 1999, pp. 4939-4950.

Bibikova, A. et al., "Enhancement of Angiogenesis in Regenerating Gastroenemius Muscle of the Toad (Bufo viridis) by Low-Energy Laser Irradiation", Anatomy and Embryology (1994), vol. 190, pp. 597-602.

Bibikova, A. et al., "Enhancement of Muscle Regeneration in the Toad (Bufo viridis) Gastrocnemius Muscle by Low-Energy Laser Irradiation", The Anatomical Record, vol. 235, 1993, pp. 374-380.

Brazzle, John, et al., Active Microneedles with Integrated Functionality, Technical Digest of the 2000 Solid-State Sensor and Actuator Workshop, Department of Bioengineering, University of Utah, Salt Lake City, Utah 84112 (five pages) (2000).

Brill, G.E., et al., Modifying influence of low level laser irradiation on the relationships in endothelial cell—blood platelet system, 10th Congress of the European Society: for Photobiology:, Vienna, Austria (one page). Jun. 8, 2004.

Burton et al., "Relation Between Pressure and Flow in the Human Forearm." J. Appl, Physiology, Nov. 1951, 4(5):329-339.

Byrnes, K.R., et al., Light Therapy Promotes Axonal Regeneration After Acute Spinal Cord Injury in Adult Rats, Program No. 275.2, Society: for Neuroscience, 2003, Abstract, 1 page.

(56) References Cited

OTHER PUBLICATIONS

Catanzaro et al., "Managing Tissue Heating in Laser Therapy to Enable Double-Blind Clinical Study," Mechanisms for Low-Light Therapy, Proc. of the SPIE, Feb. 28, 2006, 6140:199-208.
Chance et al.: "Comparison of Time-Resolved and -Unresolved Measurements of Deoxyhemoglobin in Brain," Proc. Natl Acad. Sci. USA, vol. 85, ul. 1988; pp. 4971-4975.
Cohen, Michael A., Method of Forming Microneedles and other Micron-Scale Transdermal Probes, Office of Technology Licensing, University of California, Berkeley, http://otl.berkeley.edu/technology/inventiondetail.Php/1000335, Abstract (two pages) Dec. 5, 2003.
Conlan, M.J. et al., "Biostimulation of Wound Healing by Low-Energy Laser Irradiation", Journal of Clin. Periodontology, vol. 23, 1996, pp. 492-496.
DeTaboada et al., "Transcranial application of low-energy laser irradiation improves neurological deficits in rats following acute stroke," Lasers Surg. Med., Jan. 2006, vol. 38:70-73.
Dirnagl, Ulrich, et al., Pathobiology of ischaemic stroke: an integrated view, TINS, vol. 22, No. 9, 1999, pp. 391-397.
Dobson, J., et al., Theory and Applications of a Magnetic Force Bioreactor, European Cells and Materials, vol. 4, Suppl. 2, 2002 (pp. 42-44).
Eells, JT, et al., Therapeutic photobiomodulation for methanol-induced retinal toxicity, Proceedings National Academy: of Science (PNAS}, vol. 100, No. 6, Mar. 18, 2003, pp. 3439-3444.
Elimadi, Aziz, et al., Trimetazidine Counteracts the Hepatic Injury Associated with Ischemia-Reperfusion by Michondrial Function, Journal of Phamacology: and Experimental Therapeutics, vol. 286, No. 1, 1998, pp. 23-28.
EPO Extended Search Report re EP Application No. 09170679.6, dated Jan. 4, 2010. in 6 pages.
Firbank et al.; "A Theoretical Study of the Signal Contributions of Regions of the Adult Head to Near-Infrared Spectroscopy Studies of Visual Evoked Responses," Neuroimage, No. 8, 1998, pp. 69-78.
Fisher, M., "Characterizing the Target of Acute Stroke Therapy", Stroke, 1997, vol. 28, pp. 866-872.
Gage, Fred H., Brain, Repair Yourself, Scientific American, Sep. 2003, pp. 47-53.
Gasparyan, Levon V., Biochemical and Biophysical Effects of Low Level Laser Irradiation, MAL 2000, Helsinki, Finland (three pages), Sep. 28-30, 2000.
Gasparyan, Levon V., et al., Low Level Laser Therapy of Male Genital Tract Chronic Inflammations, WALT 2-nd Congress {Kansas City, USA), 1998 (two pages).
Gasparyan, Levon V., et al., The influence of LED irradiation at different wavelengths on functional activity of blood platelets, 10th Congress of the European Society of Photobiology, Vienna, Austria, 2003 (one page).
Gasparyan, Levon V., et al., The influence of LED irradiation at different wavelengths with antioxidants on functional activity of blood platelets, Laser, Florence, 2003 (one page).
Gasparyan, Levon V., Experience of Russian {former USSR) Scientists in LLL T and UV Blood Irradiation, MAL 2000, Helsinki, Finland (four pages), Sep. 28-30, 2000.
Gasparyan, Levon V., Investigation of Sensations, Associated with Laser Blood Irradiation, WALT 2-nd Congress (Kansas City, USA), 1998 (two pages).
Gasparyan, Levon V., Millimeter Wave Therapy, MAL 2000, Helsinki, Finland (three pages), Sep. 28-30, 2000.
Gordon, G. A., "The Use of low power lasers in sports medicine", Clinical Sports Medicine 2, 53-61 (1990).
Gross, Garrett J., et al., Mechanisms of Postischemic Contractile Dysfunction, Myocardial Protection From Surgical Ischemic-Reperfusion Injury, An International Symposium, Asheville, North Carolina, Sep. 21-24, 1997, pp. 1898-1904.
Hamblin et al., "Mechanisms of Low Level Light Therapy," Proc. of SPIE, Feb. 2006, 6140:614001-1-614001-12.
Iadecola, Costantino, et al., Inhibition of inducible nitric oxide synthase ameliorates ischemic damage, Am. J. Physiol., vol. 268, 1995, pp. R286-R292.

Ilic et al., "Effects of power densities, continuous and pulse frequencies, and number of sessions of low-level laser therapy on intact rat brain," Photomed. Laser Surg., Aug. 2006, 24(4):458-466.
International Preliminary Report on Patentability for PCT/US04/029724 (ACULSR.5CP1 HPC), dated Mar. 23, 2006, 8 pages.
International Preliminary Report on Patentability for PCT/US2005/004873 (ACULSR.OOSQPC), dated Sep. 14, 2006, 15 pages.
International Preliminary Report on Patentability for PCT/US2007/002219 (ACULSR.052VPC), dated May 2, 1998, 10 pages.
International Preliminary Report on Patentability for PCT/US2007/002474 (ACULSR.051VPC), dated Apr. 16, 2008, 11 pages.
International Search Report and Written Opinion dated Oct. 28, 2009 for PCT/US2009/037121 (ACULSR.062QPC) in 20 pages.
International Search Report and Written Opinion for PCT/US2005/004873 (ACULSR.008QPC), dated Sep. 5, 2005, 22 pages.
International Search Report and Written Opinion for PCT/US2007/002219 (ACULSR.052VPC), dated Jul. 5, 2007, 12 pages.
International Search Report and Written Opinion for PCT/US2007/002474 (ACULSR.051VPC), dated Sep. 27, 2007, 16 pages.
International Search Report for PCT/CA99/00156, dated Jun. 11, 1999, 3 pages.
International Search Report for PCT/US02/36808 (ACULSR.009VPC), dated Apr. 2, 2003, 2 pages.
International Search Report for PCT/US03/00747 (ACULSR.007VPC), dated May 14, 2003, 3 pages.
Janssen et al., "Modeling of temperature and perfusion during scalp cooling," Phys. Med. Biol., Aug. 18, 2005, 50:4065-4073.
Karu et al., "Cell attachment to extracellular matrices is modulated by pulsed radiation at 820 nm and chemicals that modify the activity of enzymes in the plasma membrane," Lasers in Surgery and Medicine, Sep. 2001, 29(3):274-281.
Karu, et al., Biostimulation of HeLa Cells by Low-Intensity Visible Light. II. Stimulation of DNA and RNA Synthesis in a Wide Spectral Range. IL Nuovo Cimento. (1984) p. 309-318.
Karu, T.I., Low power laser therapy, in Biomedical Photonics Handbook, Ch. 48, Editor-in-Chief Tuan Vo-Dinh, Boca Raton, CRC Press, 2003, 29 pages.
Karu, Tiina, Mechanisms of interaction of monochromatic visible light with cells, Proc. SPIE, vol. 2630, pp. 2-9, 1996.
Karu, Tiina, Mechanisms of Low-Power Laser Light Action on Cellular Level, Effects of Low-Power Light on Biological Systems V, Proceedings of SPIE, Jul. 7, 2000, vol. 4159 pp. 1-17.
Karu, Tiina, Photobiological Fundamentals of Low Power Laser Therapy, IEEE Journal of Quantum Electronics, vol. QE-23, No. 10, Oct. 1987, pp. 1703-1717.
Lampl et al., "Infrared laser therapy for ischemic stroke: a new treatment strategy: Results of the NeuroThera Effectiveness and Safety Trial-I (NEST-I)," Stroke, Jun. 1, 2007, 38(6):1843-9.
Lapchak et al., "Neuroprotective effects of the spin trap agent disodium-[(tert-butylimino)methyl]benzene-1,3-disulfonate N-oxide (generic NXY-059) in a rabbit small clot embolic stroke model: Combination studies with the thrombolytic tissue plasminogen activator," Stroke, May 2002, 33(5):1411-1415.
Lapchak et al., "Transcranial infrared laser therapy improves clinical rating scores after embolic strokes in rabbits," Stroke, May 2004, 35(8):1985-1988.
Laser Exchange: Delivering the medicine of the future, http://www.laserexchange.co.uk/lase-therapy/ultrasound.htm; 42 pages, Oct. 13, 2004.
Lepselter et al., "Biological and clinical aspects in laser hair removal," J. Dermatological Treatment, 2004, 15(2):72-83.
Leung, Mason C.P., et al., Treatment of Experimentally Induced Transient Cerebral Ischemia with Low Energy Laser Inhibits Nitric Oxide Synthase Activity and Up-Regulates the Expressioh of Transforming Growth Factor-Beta 1, Laser in Surgery and Medicine, 31 :283-288 (2002).
Lisman et al., "Two Light-Induced Processes in the Photoreceptor Cells of Limulus Ventral Eye," J. Gen. Physiology, Nov. 1971, 58(5):544-561.
Lychagov, Vladislav V., et al. Experimental study of NIRtransmittance of the human skull, Proc. of SPIE, vol. 6085, 2006 (five pages).

(56) References Cited

OTHER PUBLICATIONS

Matas et al., "Eliminating the Issue of Skin Color in Assessment of the Blanch Response," Adv. in Skin & Wound Care, Jul. 2001, 14(4):180-188.
Mester, E., et al., Effect of Laser Rays on Wound Healing, The American Journal of Surgery, vol. 122, Oct. 1971, pp. 532-535.
Mochizuki-Oda, Noriko, et al., Effects of near-infra-red laser irradiation on adenosine triphosphate and adenosine diphosphate contents of rat brain tissue, Neuroscience Letters 323, May 3, 2002, pp. 207-210.
Niitsuma et al., "Experimental study of decubitus ulcer formation in the rabbit ear lobe," J. of Rehab. Res. and Dev., Jan. 2003, 40(1):67-72.
Nishioka, Norman S., et al., Reflection and Transmission of Laser Light From the Esophagus: The Influence of Incident Angle, Gastroenterology:, vol. 94, 1988, pp. 1180-1185.
Nissan, M. et al., "HeNe Laser Irradiation Delivered Transcutaneously: Its Effect on the Sciatic Nerve of Rats", Lasers in Surgery and Medicine, vol. 6, pp. 435-438, 1986.
Olesin, Al, et al., Laser irradiation of venous blood for production of reperfusion syndrome in myocardial infarction, Patologisheskaia fiziologiia, Sep-Dec., 1992 (5-6) p. 20-3, ISSN 0031-2991 Journal Code: 0376421, English abstract of Russian article), 1 page.
Oron, Uri, et al., Attenuation of Infarct Size in Rats and Dogs after Myocardial Infarction by Low-Energy Laser Irradiation, Lasers in Surgery and Medicine, vol. 28, 2001, pp. 204-211.
Oron, Uri, et al., Low-Energy Laser Irradiation Reduces Formation of Scar Tissue After Myocardial Infarction in Rats and Dogs, Circulation, vol. 103, Jan. 16, 2001, pp. 296-301.
Park, James L., Ph.D., et al., Mechanisms of Myocardial Reperfusion Injury, The Annals of Thoracic Surgery, Official Journal of Thoracic Surgeons and the Southern Thoracic Surgical Association, vol. 68, No. 5, Nov. 1999, pp. 1905-1912.
Physical Therapy, The Efficacy of Laser Therapy for Musculoskeletal and Skin Disorders: A Criteria-Based Metanalysis of Randomized Clinical Trials, vol. 72, No. 7, Jul. 1992, pp. 483/12-491/21.
Pogue et al.: "Comparison of Image Geometries for Diffuse Optical Tomography of Tissue," Optics Express, vol. 4, No. 8, Apr. 12, 1999, pp. 270-286.
Semenza, Gregg L., et al., Regulation of Mammalian 02 Homeostatis by Hypoxia-Inducible Factor 1, Ann. Rev. Cell Dev. Biol., vol. 15, 1999, pp. 551-578.
Smith, Kendric C., "The Photobiological Basis of Low Level Laser Radiation Therapy", Photobiological Basis of LLLT, pp. 1-7, 1991.
Sommer et al., "Stressed cells survive better with light," J. Proteome Res., Aug. 2002, (2002), 1(5):475.
Stys, Peter K., Anoxis and Ischemic Injury of Myelinated Axons in CNS White Matter: From Mechanistic Concepts to Therapeutics, J. Cereb. Blood Flow Metab., vol. 18, No. 1, Jan. 1998, 42 pages (037C1 lists DD. 2-25).
Thor Laser, 100mW, Thor, lllt, LLLT, Low Level Laser Therapy, low level laser therapy, Lazer, Thorl., http:///www.thorlaser.com/specs/100m W.html, Oct. 6, 1999, p. 1.
Thor Laser, Specifications, Thor: Specifications, Thor, lllt, LLLT, Low Level Laser Therapy, low level laser therapy, http://www.thorlaser.com/specs, Oct. 6, 1999, pp. 1-2.
Thor, Specification, 200mW/650nm Laser probe, http://www.thorlaser.com/specs/200mW650nm.html, web page (1 page), Oct. 6, 1999.
Thor, Specification, 200mW/810 nm Laser probe, http://www.thorlaser.com/specs/ 200mWhtml, web page (1 page), Oct. 6, 2009.
Thor, Specification, 30mW Red Laser probe, www.thorlaser.com/specs/ 680.html, web page (1 page), Oct. 6, 1999.
Thor, Specification, 500mW/810nm Laser probe, http://www.thorlaser.com/specs/ 500mW.html, web page (1 page), Oct. 6, 1999.
Thor: Is LLT Different from Ultrasound?, http://www.thorlaser.com/LLLT/is-LLLT-diff-from-ultrasound.htm, 2 pages, Oct. 13, 2004.
Thor: Product List, Thor, lllt, LLLT, Low Level Laser Therapy, Laz., http://www.thorlaser.com/prodlist/index.html, Oct. 6, 1999, pp. 1-4.
Toon, John, Taking the "Ouch" Out of Needles: Arrays of Micron-Scale "Microneedles" Offer New Technique for Drug Delivery, Georgia Tech Research News, Jun. 22, 1998 (three pages).
Toricelli, P., et al., Laser Biostimulation of cartilage: in vitro evaluation, Biomed. Pharmacother., 2001, vol. 55, pp. 117-120.
Tuchin, Valery, Tissue Optics: Light Scattering Methods and Instruments for Medical Diagnosis, SPIE Press, Tutorial Texts in Optical Engineering, vol. TT38, 2000, pp. 3-11, 2000.
Tuner, Jan, et al., Low Level Laser Therapy, Clinical Practice and Scientific Background, Prima Books in Sweden AB, 1999, pp. 1-9, 45-58, 62-114, 113-116, 118, 132-134, 134-135, 149-151, 151-156, 185, 334-364.
Van Breugel et al. "He-Ne laser irradiation affects proliferation of cultured rat-Schwann cells in a dose-dependent manner," Journal of Neurocytology 22, 185-190 (1993).
Van Breugel, Hans H.F.1., et al., Power Density and Exposure Time of He-Ne Laser Irradiation are More Important than Total Energy Dose in Photo-Biomoducation of Human Fibroblasts InVitro, Lasers in Surgery and Medicine (1992), Wiley-Liss, Inc., pp. 528-537.
Weiss, N et al., "Enhancement of Muscle Regeneration in the Rat Gastrocnemius Muscle by Low Energy Laser Irradiation", Anat. Embroyl. (1992), vol. 186, pp. 497-503.
Wells et al., "Biophysical mechanisms responsible for pulsed low-level laser excitation of neural tissue," Proc. of SPIE, Mar. 2006, 6084:60840X-1-60840X-7.
Wong-Riley, Margaret T.T., et al., Light-emitting diode treatment reverse the effect of TTX on cytochrome oxidase in neurons, NeuroRegort, vol. 12, No. 14, Oct. 8, 2001, pp. 3033-3037.
Yaakobi, Tali, et al., Long-term effect of low energy laser irradiation on infarction and reperfusion injury in the rat heart, J. Aqri. Physiol., vol. 90, 2001, pp. 2411-2419.

\* cited by examiner

APPARATUS AND METHOD FOR IRRADIATING A SURFACE WITH LIGHT

CROSS-REFERENCE TO RELATED APPLICATIONS

The present application is a continuation application of U.S. patent application Ser. No. 16/445,661 filed on Jun. 19, 20219 (now U.S. Pat. No. 11,219,782), which is a continuation of U.S. patent application Ser. No. 12/389,294 filed on Feb. 19, 2009 (now U.S. Pat. No. 10,357,662), which are hereby incorporated by reference in their entireties.

BACKGROUND OF THE INVENTION

Field of the Invention

The present invention relates in general to phototherapy, and more particularly, to novel apparatuses and methods for phototherapy of brain tissue.

Description of the Related Art

There are numerous neurologic conditions, such as neurodegenerative diseases (e.g., Alzheimer's disease, Parkinson's disease), Huntington's disease, demyelinating diseases (e.g., multiple sclerosis), cranial nerve palsies, traumatic brain injury, stroke, and spinal cord injury which could possibly benefit from application of phototherapy. Most of these conditions cause significant morbidity and mortality and involve tremendous burden to society, families and caregivers. Many neurologic conditions have no currently available effective therapies or the therapies that are available are not adequate to restore functional recovery, sustain quality of life, or halt disease progression.

One example of a neurologic condition that remains a major unmet medical need is stroke, also called cerebrovascular accident (CVA). Stroke is caused by a sudden disruption of blood flow to a discrete area of the brain that is brought on by the lodging of a clot in an artery supplying blood to an area of the brain (called an ischemic stroke), or by a cerebral hemorrhage due to a ruptured aneurysm or a burst artery (called a hemorrhagic stroke). There are over 750,000 stroke victims per year in the United States, and approximately 85% of all strokes are ischemic and 15% are hemorrhagic. The consequence of stroke is a loss of function in the affected brain region and concomitant loss of bodily function in areas of the body controlled by the affected brain region. Depending upon the extent and location of the primary insult in the brain, loss of function varies greatly from mild or severe, and may be temporary or permanent. Lifestyle factors such as smoking, diet, level of physical activity and high cholesterol increase the risk of stroke, and thus stroke is a major cause of human suffering in developed nations. Stroke is the third leading cause of death in most developed nations, including the United States.

Stroke treatment is often restricted to providing basic life support at the time of the stroke, followed by rehabilitation. Currently, the only FDA-cleared treatment of ischemic stroke involves thrombolytic therapy using tissue plasminogen activator (tPA). However, tPA can only be used within three hours of stroke onset and has several contraindications, therefore, only a small percentage of stroke victims receive this drug.

A high level of interest and clinical need remains in finding new and improved therapeutic interventions for treatment of stroke and other neurologic conditions that continue to devastate millions of lives each year and where few effective therapies exist.

SUMMARY OF THE INVENTION

In certain embodiments, an apparatus is provided for irradiating a portion of a patient's scalp with light. The apparatus comprises a source of light comprising one or more wavelengths in a range of about 630 nanometers to about 1064 nanometers. The apparatus further comprises an output optical element in optical communication with the source. The output optical element comprises an emission surface configured to emit a light beam having a cross-sectional area greater than about 2 cm$^2$ at the emission surface of the output optical element and having a time-averaged irradiance in a range of about 10 mW/cm$^2$ to about 10 W/cm$^2$ across the cross-sectional area. The apparatus further comprises a thermally conductive portion configured to be placed in thermal communication with the irradiated portion of the patient's scalp and to remove heat from the irradiated portion of the patient's scalp at a rate in a range of about 0.1 Watt to about 5 Watts.

In certain embodiments, a method of irradiating a surface with light is provided. The method comprises emitting a light beam from an emission surface of an optical element. The light beam at the emission surface has one or more wavelengths in a range of about 630 nanometers to about 1064 nanometers, a cross-sectional area greater than about 2 cm$^2$, and a time-averaged irradiance in a range of about 10 mW/cm$^2$ to about 10 W/cm$^2$ across the cross-sectional area. The method further comprises removing heat from the emission surface at a rate in a range of about 0.1 Watt to about 5 Watts. The method further comprises impinging the irradiated surface with the light beam.

In certain embodiments, an apparatus is provided for irradiating a patient's scalp with light. The apparatus comprises a first portion and a second portion mechanically coupled to the first portion and in optical communication with the first portion. The second portion is configured to be placed in thermal communication with the patient's scalp such that the light from the first portion propagates through the second portion during operation of the apparatus. The first portion and the second portion are configured to move relative to one another in response to the second portion being placed in thermal communication with the patient's scalp.

In certain embodiments, a method of irradiating a surface with light is provided. The method comprises providing an apparatus comprising a first portion and a second portion mechanically coupled to the first portion and in optical communication with the first portion. The first portion and the second portion are configured to move relative to one another. The method further comprises placing the second portion in thermal communication with the surface. The method further comprises irradiating the surface such that the light from the first portion propagates through the second portion. The method further comprises moving the first portion and the second portion relative to one another in response to the second portion being placed in thermal communication with the surface.

In certain embodiments, an apparatus is provided for irradiating a patient's scalp with light. The apparatus comprises an output optical assembly comprising an emission surface, wherein during operation of the apparatus, light propagates through the output optical assembly along a first optical path to the emission surface. The apparatus further comprise a sensor spaced from the output optical assembly. The sensor is positioned to receive radiation from the output optical assembly propagating through the output optical assembly along a second optical path, the first optical path and the second optical path having a non-zero angle therebetween.

In certain embodiments, a method for irradiating a surface with light is provided. The method comprises providing an optical element comprising a substantially optically transmissive and substantially thermally conductive material, the optical element having a first surface and a second surface. The method further comprises placing the first surface in thermal communication with the irradiated surface. The method further comprises propagating light along a first optical path through the second surface and through the first surface to the irradiated surface. The method further comprises detecting radiation propagating along a second optical path from at least a portion of the second surface, the first optical path and the second optical path having a non-zero angle therebetween.

In certain embodiments, an apparatus is provided for irradiating a patient's scalp with light. The apparatus comprises a thermoelectric assembly responsive to an electric current applied to the thermoelectric assembly by cooling at least a first surface of the thermoelectric assembly and heating at least a second surface of the thermoelectric assembly. The thermoelectric assembly is configured to be releasably mechanically coupled to an output optical assembly so as to have the first surface in thermal communication with the output optical assembly. The thermoelectric assembly generally surrounds a first region, wherein, during operation of the apparatus, light irradiating a portion of the patient's scalp propagates through the first region. The apparatus further comprises a heat sink in thermal communication with the second surface of the thermoelectric assembly.

In certain embodiments, an apparatus wearable by a patient is provided. The apparatus comprises a body adapted to be worn over at least a portion of the patient's scalp. The apparatus further comprises a plurality of indicators corresponding to a plurality of treatment site locations at the patient's scalp where light is to be applied to irradiate at least a portion of the patient's brain.

In certain embodiments, an apparatus wearable by a patient is provided. The apparatus comprises means for identifying a plurality of treatment site locations at the patient's scalp where light is to be applied to irradiate at least a portion of the patient's brain. The apparatus further comprises means for indicating to an operator a sequential order for irradiating the treatment site locations.

In certain embodiments, a method for denoting a brain phototherapy procedure is provided. The method comprises identifying a plurality of treatment site locations at a patient's scalp, wherein at least one of the treatment site locations has an area of at least 1 cm$^2$. The method further comprises indicating a sequential order for irradiation of the treatment site locations.

In certain embodiments, a method of treating a patient's brain is provided. The method comprises noninvasively irradiating a first area of at least 1 cm$^2$ of the patient's scalp with laser light during a first time period. The method further comprises noninvasively irradiating a second area of at least 1 cm$^2$ of the patient's scalp with laser light during a second time period, wherein the first area and the second area do not overlap one another, wherein the first time period and the second time period do not overlap one another.

For purposes of summarizing the present invention, certain aspects, advantages, and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

DETAILED DESCRIPTION OF THE PREFERRED EMBODIMENT

Figure 1:
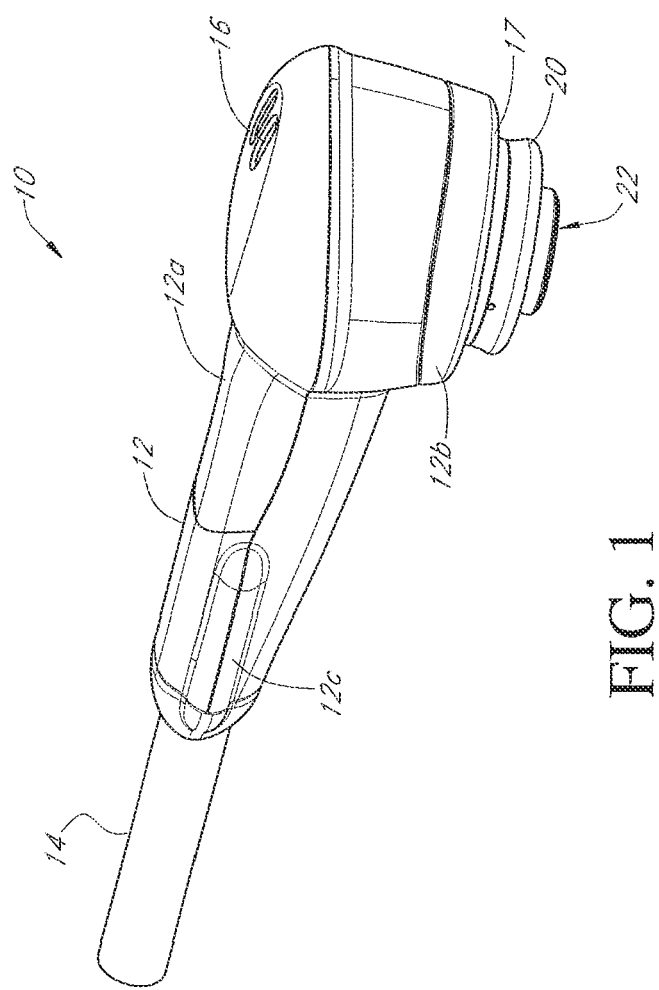
FIG. 1 schematically illustrates an example beam delivery apparatus in accordance with certain embodiments described herein.

Low level light therapy ("LLLT") or phototherapy involves therapeutic administration of light energy to a patient at lower irradiances than those used for cutting, cauterizing, or ablating biological tissue, resulting in desirable biostimulatory effects while leaving tissue undamaged. In non-invasive phototherapy, it is desirable to apply an efficacious amount of light energy to the internal tissue to be treated using light sources positioned outside the body. (See, e.g., U.S. Pat. Nos. 6,537,304 and 6,918,922, both of which are incorporated in their entireties by reference herein.)

Laser therapy has been shown to be effective in a variety of settings, including treating lymphoedema and muscular trauma, and carpal tunnel syndrome. Recent studies have shown that laser-generated infrared radiation is able to penetrate various tissues, including the brain, and to modify function. In addition, laser-generated infrared radiation can induce effects including, but not limited to, angiogenesis, modify growth factor (transforming growth factor-β) signaling pathways, and enhance protein synthesis.

However, absorption of the light energy by intervening tissue can limit the amount of light energy delivered to the target tissue site, while heating the intervening tissue. In addition, scattering of the light energy by intervening tissue can limit the irradiance (or power density) or energy density delivered to the target tissue site. Brute force attempts to circumvent these effects by increasing the power and/or irradiance applied to the outside surface of the body can result in damage (e.g., burning) of the intervening tissue.

Non-invasive phototherapy methods are circumscribed by setting selected treatment parameters within specified limits so as to preferably avoid damaging the intervening tissue. A review of the existing scientific literature in this field would cast doubt on whether a set of undamaging, yet efficacious, parameters could be found for treating neurologic conditions. However, certain embodiments, as described herein, provide devices and methods which can achieve this goal.

Such embodiments may include selecting a wavelength of light at which the absorption by intervening tissue is below a damaging level. Such embodiments may also include setting the power output of the light source at low, yet efficacious, irradiances (e.g., between approximately 100 µW/cm$^2$ to approximately 10 W/cm$^2$) at the target tissue site, and time periods of application of the light energy at a few seconds to minutes to achieve an efficacious energy density at the target tissue site being treated. Other parameters can also be varied in the use of phototherapy. These other parameters contribute to the light energy that is actually delivered to the treated tissue and may play key roles in the efficacy of phototherapy. In certain embodiments, the irradiated portion of the brain can comprise the entire brain.

In certain embodiments, the target area of the patient's brain includes the area of infarct, i.e. to neurons within the "zone of danger." In other embodiments, the target area includes portions of the brain not within the zone of danger. Information regarding the biomedical mechanisms or reactions involved in phototherapy is provided by Tiina I. Karu in "Mechanisms of Low-Power Laser Light Action on Cellular Level", Proceedings of SPIE Vol. 4159 (2000), Effects of Low-Power Light on Biological Systems V, Ed. Rachel Lubart, pp. 1-17, and Michael R. Hamblin et al., "Mechanisms of Low Level Light Therapy," Proc. of SPIE, Vol. 6140, 614001 (2006), each of which is incorporated in its entirety by reference herein.

In certain embodiments, the apparatuses and methods of phototherapy described herein are used to treat strokes or other sources of neurodegeneration. As used herein, the term "neurodegeneration" refers to the process of cell destruction resulting from primary destructive events such as stroke or CVA, as well as from secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amylotrophic lateral sclerosis, heat stroke, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules, including but not limited to, apoptosis, depletion of cellular energy stores because of changes in mitochondrial membrane permeability, release or failure in the reuptake of excessive glutamate, reperfusion injury, and activity of cytokines and inflammation. Both primary and secondary mechanisms contribute to forming a "zone of danger" for neurons, wherein the neurons in the zone have at least temporarily survived the primary destructive event, but are at risk of dying due to processes having delayed effect.

In certain embodiments, the apparatuses and methods described herein are used to provide neuroprotection. As used herein, the term "neuroprotection" refers to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

In certain embodiments, the apparatuses and methods described herein are used to improve neurologic function, to provide neurologic enhancement, or to regain previously lost neurologic function. The term "neurologic function" as used herein includes both cognitive function and motor function. The term "neurologic enhancement" as used herein includes both cognitive enhancement and motor enhancement. The terms "cognitive enhancement" and "motor enhancement" as used herein refer to the improving or heightening of cognitive function and motor function, respectively.

The term "cognitive function" as used herein refers to cognition and cognitive or mental processes or functions, including those relating to knowing, thinking, learning, perception, memory (including immediate, recent, or remote memory), and judging. Symptoms of loss of cognitive function can also include changes in personality, mood, and behavior of the patient. The term "motor function" as used herein refers to those bodily functions relating to muscular movements, primarily conscious muscular movements, including motor coordination, performance of simple and complex motor acts, and the like.

Diseases or conditions affecting neurologic function include, but are not limited to, Alzheimer's disease, dementia, AIDS or HIV infection, Cruetzfeldt-Jakob disease, head trauma (including single-event trauma and long-term trauma such as multiple concussions or other traumas which may result from athletic injury), Lewy body disease, Pick's disease, Parkinson's disease, Huntington's disease, drug or alcohol abuse, brain tumors, hydrocephalus, kidney or liver disease, stroke, depression, and other mental diseases which cause disruption in cognitive function, and neurodegeneration.

Beam Delivery Apparatus

The phototherapy methods for the treatment of stroke described herein may be practiced and described using various light delivery systems. Such light delivery systems may include a low level laser therapy apparatus such as that shown and described in U.S. Pat. Nos. 6,214,035, 6,267,780, 6,273,905, 6,290,714, and 7,303,578, and U.S. Pat. Appl. Publ. No. 2007/0179571 A1, each of which is incorporated in its entirety by reference herein.

FIG. 1 schematically illustrates an example beam delivery apparatus 10 in accordance with certain embodiments described herein. The apparatus 10 comprises a housing 12, a flexible conduit 14 operatively coupled to the housing 12, and at least one status indicator 16. In certain embodiments, the apparatus 10 comprises an output optical assembly 20 comprising an emission surface 22 through which a light beam 30 is emitted. The output optical assembly 20 is configured to be releasably mechanically coupled to other components of the apparatus 10.

In certain embodiments, the housing 12 is sized to be easily held in one hand (e.g., having a length of approximately 5⅞ inches). The housing 12 of certain embodiments further comprises one or more portions 12a, 12b comprising a biocompatible material since they may contact the operator, the patient, or both. For example, one or more low durometer elastomer materials (e.g., rubber, polymers, thermoplastic resins) can be used in certain embodiments. The portion 12a is configured to be grasped by a user's hand during operation of the apparatus 10. The housing 12 of certain embodiments is configured so that the emission surface 22 can be held in position and sequentially moved by hand to irradiate selected portions of the patient's skin. In certain embodiments, the housing 12 comprises one or more recesses or protrusions which facilitate the housing 12 being gripped by the user. In certain embodiments, the housing 12 is configured to be placed on a testing system to measure or monitor the operative parameters of the apparatus 10. The housing 12 of certain such embodiments comprises an alignment rib 12c configured to provide a registration protrusion which mates with a corresponding registration recess on the testing system to facilitate proper alignment of the emission surface 22 with the testing system. The housing 12 of certain embodiments comprises two or more portions (e.g., 2-piece cast urethane with 60A overmolding or 3-piece Lustran® with thermoplastic elastomer overmolding) which fit together to form a shell in which other operative components are held. In certain embodiments, the light used by the apparatus 10 can cause eye damage if viewed by an individual. In such embodiments, the apparatus 10 can be configured to provide eye protection so as to avoid viewing of the light by individuals. For example, opaque materials can be used for the housing 12 and appropriately placed to block the light from being viewed directly. In addition, interlocks can be provided so that the light source is not activated unless the apparatus 10 is in place, or other appropriate safety measures are taken.

In certain embodiments, the housing 12 further comprises a flexible boot 17 generally surrounding the portion of the apparatus 10 which is releasably mounted to the output optical assembly 20. The boot 17 of certain embodiments provides a barrier to control, inhibit, prevent, minimize, or reduce contaminants from entering the housing 12. Thus, by virtue of the boot 17 providing a barrier, the contamination entering the housing 12 is lower than it would otherwise be if the boot 17 did not provide a barrier. Example materials for the flexible boot 17 include but are not limited to, rubber or another elastomer.

In certain embodiments, the conduit 14 is configured to operatively couple the apparatus 10 to various control, power, and cooling systems that are spaced from the housing 12. In certain embodiments, the conduit 14 comprises at least one optical fiber configured to transmit light from a light source to the apparatus 10 to be emitted from the emission surface 22. In certain embodiments, the conduit 14 further comprises one or more electrically conductive wires (e.g., one 20-conductor cable, four 6-conductor cables, ground braid) configured to transmit signals between the apparatus 10 (e.g., trigger switches or temperature sensors within the apparatus 10) and a control system spaced from the apparatus 10 and/or to provide electrical power to the apparatus 10 (e.g., for a thermoelectric cooler) from a power system. In still other embodiments, the apparatus 10 comprises a power source (e.g., a battery). In certain embodiments, the conduit 14 comprises one or more coolant tubes (e.g., 0.125-inch inner diameter) configured to have a coolant (e.g., liquid or gas) flow to the apparatus 10 from a cooling system. In certain embodiments, the conduit 14 comprises one or more connectors which are mechanically coupled to one or more corresponding connectors within the housing 12. For example, the conduit 14 can comprise an SMA connector at an end of the optical fiber which is mechanically coupled to a corresponding SMA mount within the housing 12.

In certain embodiments, the conduit 14 comprises a protective sheath around the one or more fibers, wires, and tubes of the conduit 14. The protective sheath of certain embodiments controls, inhibits, prevents, minimizes, or reduces light from exiting the conduit 14 in the event of a failure of the at least one optical fiber. Thus, by virtue of having the sheath, the light exiting the conduit 14 upon fiber failure is lower than it would otherwise be without the sheath. In certain embodiments, the protective sheath comprises a strain relief apparatus having a plurality of rigid segments (e.g., stainless steel), with each segment having a generally cylindrical tubular shape and a longitudinal axis. Each segment is articulately coupled to neighboring segments such that an angle between the longitudinal axes of neighboring segments is limited to be less than a predetermined angle. In certain embodiments, the protective sheath allows the conduit 14 to be moved and to bend, but advantageously limits the radius of curvature of the bend to be sufficiently large to avoid breaking the one or more fibers, wires, or tubes therein. In certain embodiments, the sheath comprises a flexible compression spring (e.g., 4 inches in length) to provide bend relief and/or a tension line to provide strain relief.

In certain embodiments, the at least one status indicator 16 comprises one, two, or more light-emitting diodes (LEDs) which are lit to visually provide the user with information regarding the status of the apparatus 10. For example, the at least one status indicator 16 can be used in certain embodiments to indicate when the laser source is ready to lase pending engagement of the trigger. In certain embodiments, the LEDs can be lit to show different colors depending on whether the optical power, electrical power, or coolant flow being provided to the apparatus 10 are sufficient for operation of the apparatus 10. In certain embodiments, the at least one status indicator 16 provides information regarding whether the output optical assembly 20 is properly mounted to the apparatus 10. Other types of status indicators (e.g., flags, sound alarms) are also compatible with certain embodiments described herein.

Figure 2A:
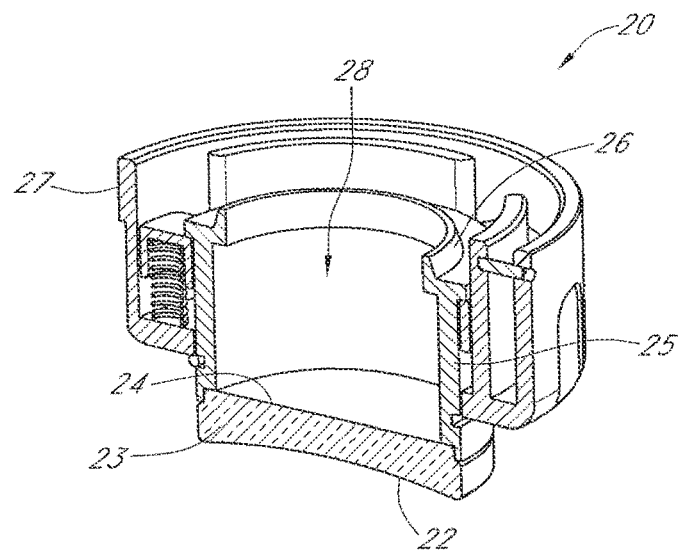
FIG. 2A schematically illustrates a cross-sectional view of an example output optical assembly in accordance with certain embodiments described herein.
Figure 2B:
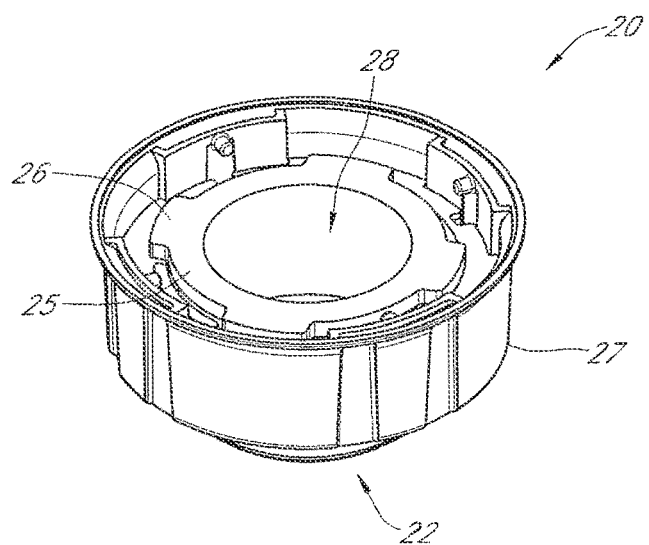
FIG. 2B schematically illustrates another example output optical assembly in accordance with certain embodiments described herein.

FIG. 2A schematically illustrates a cross-sectional view of an example output optical assembly 20 in accordance with certain embodiments described herein. FIG. 2B schematically illustrates another example output optical assembly 20 in accordance with certain embodiments described herein. The output optical assembly 20 comprises an optical element 23 comprising the emission surface 22 and a surface 24 facing generally away from the emission surface 22. As used herein, the term "element" is used in its broadest sense, including, but not limited to, as a reference to a constituent or distinct part of a composite device. The output optical assembly 20 further comprises a thermal conduit 25 in thermal communication with the optical element 23 (e.g., with a portion of the surface 24). The thermal conduit 25 comprises at least one surface 26 configured to be in thermal communication with at least one heat dissipating surface of the apparatus 10 (e.g., a surface of a cooling mechanism). The output optical assembly 20 further comprises a coupling portion 27 (e.g., spring-loaded 3-pin bayonet mount or 4-pin bayonet mount) configured to be releasably attached and detached from the housing 12. In certain embodiments, the output optical assembly 20 comprises one or more springs which provide a sufficient force on the at least one surface 26 towards the at least one heat dissipating surface of the apparatus 10 to have the desired thermal conductivity between the two. Various examples of output optical assemblies 20 compatible with certain embodiments described herein are described more fully in U.S. patent application Ser. No. 12/233,498, which is incorporated in its entirety by reference herein.

In certain embodiments, the output optical assembly 20 is configured to be placed in thermal communication with the patient's scalp (e.g., the optical element 23 is configured to contact the patient's scalp or is configured to be spaced from the patient's scalp but to contact a thermally conductive material in contact with the patient's scalp). In certain embodiments in which the output optical assembly 20 is cooled, the output optical assembly 20 cools at least a portion of the patient's scalp (e.g., the portion of the scalp being irradiated). Thus, in certain embodiments, the output optical assembly 20 is adapted to control, inhibit, prevent, minimize, or reduce temperature increases at the scalp caused by the light. Thus, by virtue of the output optical assembly 20 cooling the portion of the patient's scalp being irradiated, the temperature of the irradiated portion of the patient's scalp is lower than it would otherwise be if the output optical assembly 20 did not cool the irradiated portion of the scalp. For example, by cooling the irradiated portion of the patient's scalp using the output optical assembly 20, the temperature of the irradiated portion of the patient's scalp can be higher than the temperature of the portion of the patient's scalp if it were not irradiated, but lower than the temperature of the portion of the patient's scalp if it were irradiated but not cooled. In certain embodiments, the patient's scalp comprises hair and skin which cover the patient's skull. In other embodiments, at least a portion of the hair is removed prior to the phototherapy treatment, so that the output optical assembly 20 substantially contacts the skin of the scalp.

The optical element 23 of certain embodiments is thermally conductive, and optically transmissive at wavelengths which are transmitted by skin. For example, in certain embodiments, the thermal conductivity of the optical element 23 is sufficient to remove heat from the irradiated portion of the patient's scalp, and the optical transmissivity of the optical element 23, at wavelengths selected to provide the desired irradiance at a target region of the brain, is sufficient to allow the desired irradiance of light to propagate through the optical element 23 to irradiated the patient's scalp. In certain embodiments, the optical element 23 comprises a rigid material, while in certain other embodiments, the optical element 23 comprises a low durometer, thermally conductive, optically transmissive material (e.g., a flexible bag or container filled with a thermally conductive, optically transmissive liquid such as water). Example rigid materials for the optical element 23 include, but are not limited to, sapphire, diamond, calcium fluoride, and zinc selenide. In certain embodiments, the optical element 23 has an emission surface 22 configured to face generally towards the surface to be irradiated (e.g., the patient's scalp). In certain embodiments, the emission surface 22 is adapted to be placed in contact with either the irradiated surface or with a substantially optically transmissive and substantially thermally conductive material which is in contact with the irradiated surface. The emission surface 22 of certain embodiments is configured to be in thermal communication with the surface to be irradiated by the light beam emitted from the emission surface 22. In certain such embodiments, the thermal conductivity of the optical element 23 is sufficiently high to allow heat to flow from the emission surface 22 to the thermal conduit 25 at a sufficient rate to control, inhibit, prevent, minimize, or reduce damage to the skin or discomfort to the patient from excessive heating of the skin due to the irradiation. Thus, by virtue of the thermal conductivity of the optical element 23, any damage to the skin or discomfort to the patient can be lower than it would otherwise be if the optical element 23 did not have a sufficiently high thermal conductivity. For example, the damage to the skin or discomfort to the patient can be higher than it would be if the portion of the patient's scalp were not irradiated, but the damage to the skin or discomfort to the patient would be lower than it would be if the optical element 23 did not have a sufficiently high thermal conductivity.

In certain embodiments, the optical element 23 has a thermal conductivity of at least approximately 10 watts/meter-K. In certain other embodiments, the thermal conductivity of the optical element 23 is at least approximately 15 watts/meter-K. Examples of materials for the optical element 23 in accordance with certain embodiments described herein include, but are not limited to, sapphire which has a thermal conductivity of approximately 23.1 watts/meter-K, and diamond which has a thermal conductivity between approximately 895 watts/meter-K and approximately 2300 watts/meter-K.

In certain embodiments, the emission surface 22 is adapted to conform to the curvature of the scalp. The emission surface 22 of certain embodiments is concave (e.g., generally spherical with a radius of curvature of about 100 millimeters). By fitting to the curvature of the scalp, the emission surface 22 advantageously controls, inhibits, prevents, minimizes, or reduces temperature increases at the scalp that would otherwise result from air-filled gaps between the emission surface 22 and the scalp. Thus, by virtue of the emission surface 22 fitting to the curvature of the portion of the patient's scalp being irradiated, the temperature of the irradiated portion of the patient's scalp is lower than it would otherwise be if the emission surface 22 did not fit to the curvature of the irradiated portion of the scalp. For example, by fitting the emission surface 22 to the curvature of the irradiated portion of the patient's scalp, the temperature of the irradiated portion of the patient's scalp can be higher than the temperature of the portion of the patient's scalp if it were not irradiated, but lower than the temperature of the portion of the patient's scalp if it were irradiated but the emission surface 22 did not fit to the portion of the patient's scalp. The existence of air gaps between the emission surface 22 and the scalp can reduce the thermal conductivity between the emission surface 22 and the scalp, thereby increasing the probability of heating the scalp by the irradiation.

In addition, the refractive-index mismatches between such an air gap and the emission surface 22 and/or the scalp can cause a portion of the light propagating toward the scalp to be reflected away from the scalp. In certain embodiments, the emission surface 22 is placed in contact with the skin of the scalp so as to advantageously substantially reduce air gaps between the emission surface 22 and the scalp in the optical path of the light. In certain other embodiments in which an intervening material (e.g., a substantially optically transmissive and substantially thermally conductive gel) is in contact with the skin and with the emission surface 22, the emission surface 22 is placed in contact with the intervening material so as to advantageously avoid creating air gaps between the emission surface 22 and the intervening material or between the intervening material and the skin. In certain embodiments, the intervening material has a refractive index at a wavelength of light impinging the scalp which substantially matches the refractive index of the scalp (e.g., about 1.3), thereby reducing any index-mismatch-generated back reflections between the emission surface 22 and the scalp. Examples of materials compatible with certain such embodiments described herein include, but are not limited to, glycerol, water, and silica gels. Example index-matching gels include, but are not limited to, those available from Nye Lubricants, Inc. of Fairhaven, Massachusetts.

In certain embodiments, the emission surface 22 comprises one or more optical coatings, films, layers, membranes, etc. in the optical path of the transmitted light which are adapted to reduce back reflections. By reducing back reflections, the emission surface 22 increases the amount of light transmitted to the brain and reduces the need to use higher irradiances which may otherwise create temperature increases at the scalp.

Figure 3A:
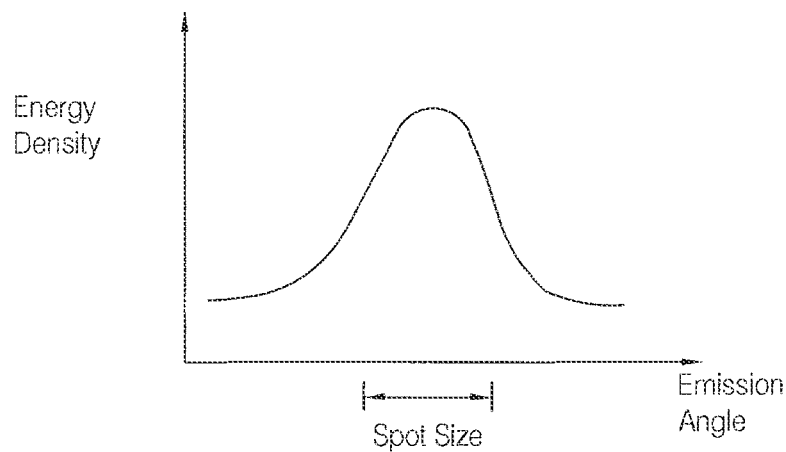
FIGS. 3A and 3B schematically illustrate the diffusive effect on the light by the output optical assembly.
Figure 3B:
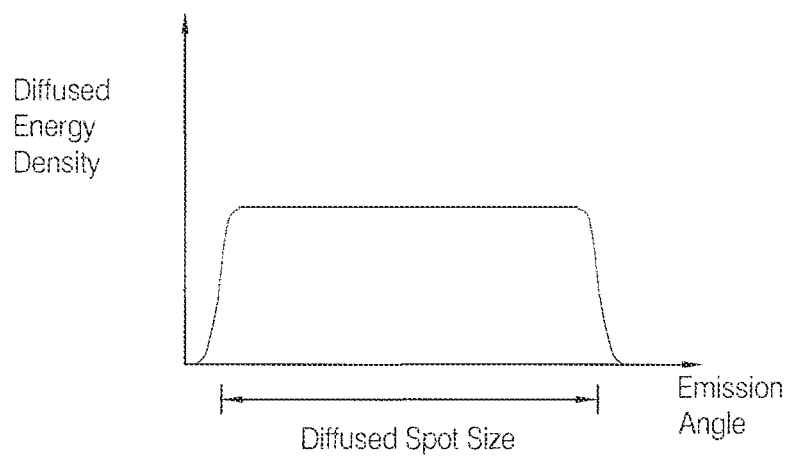

In certain embodiments, the output optical assembly 20 is adapted to diffuse the light prior to reaching the scalp to advantageously homogenize the light beam prior to reaching the emission surface 22. Generally, intervening tissues of the scalp and skull are highly scattering, which can reduce the impact of non-uniform beam intensity distributions on the illumination of the patient's cerebral cortex. However, non-uniform beam intensity distributions with substantial inhomogeneities could result in some portions of the patient's scalp being heated more than others (e.g., localized heating where a "hot spot" of the light beam impinges the patient's scalp). In certain embodiments, the output optical assembly 20 advantageously homogenizes the light beam to have a non-uniformity less than approximately 3 millimeters. FIGS. 3A and 3B schematically illustrate the diffusive effect on the light by the output optical assembly 20. An example energy density profile of the light prior to being transmitted through the output optical assembly 20, as illustrated by FIG. 3A, is peaked at a particular emission angle. After being diffused by the output optical assembly 20, as illustrated by FIG. 3B, the energy density profile of the light does not have a substantial peak at any particular emission angle, but is substantially evenly distributed among a range of emission angles. By diffusing the light, the output optical assembly 20 distributes the light energy substantially evenly over the area to be illuminated, thereby controlling, inhibiting, preventing, minimizing, or reducing "hot spots" which would otherwise create temperature increases at the scalp. Thus, by virtue of the output optical assembly 20 diffusing the light, the temperature of the irradiated portion of the patient's scalp is lower than it would otherwise be if the output optical assembly 20 did not diffuse the light. For example, by diffusing the light using the output optical assembly 20, the temperature of the irradiated portion of the patient's scalp can be higher than the temperature of the portion of the patient's scalp if it were not irradiated, but lower than the temperature of the portion of the patient's scalp if it were irradiated but the light were not diffused by the output optical assembly 20. In addition, by diffusing the light prior to reaching the scalp, the output optical assembly 20 can effectively increase the spot size of the light impinging the scalp, thereby advantageously lowering the irradiance at the scalp, as described in U.S. Pat. No. 7,303,578, which is incorporated in its entirety by reference herein.

In certain embodiments, the output optical assembly 20 provides sufficient diffusion of the light such that the irradiance of the light is less than a maximum tolerable level of the scalp and brain. For example, the maximum tolerable level of certain embodiments is a level at which the patient experiences discomfort or pain, while in certain other embodiments, the maximum level is a level at which the patient's scalp is damaged (e.g., burned). In certain other embodiments, the output optical assembly 20 provides sufficient diffusion of the light such that the irradiance of the light equals a therapeutic value at the subdermal target tissue. The output optical assembly 20 can comprise example diffusers including, but are not limited to, holographic diffusers such as those available from Physical Optics Corp. of Torrance, California and Display Optics P/N SN1333 from Reflexite Corp. of Avon, Connecticut.

In certain embodiments, the output optical assembly 20 provides a reusable interface between the apparatus 10 and the patient's scalp. In such embodiments, the output optical assembly 20 can be cleaned or sterilized between uses of the apparatus 10, particularly between uses by different patients. In other embodiments, the output optical assembly 20 provides a disposable and replaceable interface between the apparatus 10 and the patient's scalp. By using pre-sterilized and pre-packaged replaceable interfaces, certain embodiments can advantageously provide sterilized interfaces without undergoing cleaning or sterilization processing immediately before use.

In certain embodiments, the output optical assembly 20 is adapted to apply pressure to at least an irradiated portion of the scalp. For example, the output optical assembly 20 is capable of applying pressure to at least an irradiated portion of the scalp upon a force being applied to the apparatus 10 (e.g., by an operator of the apparatus 10 pressing the apparatus 10 against the patient's scalp by hand or by mechanical means to generate force, such as weights, springs, tension straps). By applying sufficient pressure, the output optical assembly 20 can blanch the portion of the scalp by forcing at least some blood out the optical path of the light energy. (For a general discussion of skin blanching, see, e.g., A. C. Burton et al., "Relation Between Blood Pressure and Flow in the Human Forearm," J. Appl. Physiology, Vol. 4, No. 5, pp. 329-339 (1951); A. Matas et al., "Eliminating the Issue of Skin Color in Assessment of the Blanch Response," Adv. in Skin & Wound Care, Vol. 14(4, part 1 of 2), pp. 180-188 (July/August 2001); J. Niitsuma et al., "Experimental study of decubitus ulcer formation in the rabbit ear lobe," J. of Rehab. Res. and Dev., Vol. 40, No. 1, pp. 67-72 (January/February 2003).) The blood removal resulting from the pressure applied by the output optical assembly 20 to the scalp decreases the corresponding absorption of the light energy by blood in the scalp. As a result, temperature increases due to absorption of the light energy by blood at the scalp are reduced. As a further result, the fraction of the light energy transmitted to the subdermal target tissue of the brain is increased. In certain embodiments, a pressure of at least 0.1 pound per square inch is used to blanch the irradiated portion of the scalp, while in certain other embodiments, a pressure of at least one pound per square inch is used to blanch the irradiated portion of the scalp. In certain embodiments, a pressure of at least about two pounds per square inch is used to blanch the irradiated portion of the scalp. Other values or ranges of pressures for blanching the irradiated portion of the scalp are also compatible with certain embodiments described herein. The maximum pressure used to blanch the irradiated portion of the scalp is limited in certain embodiments by patient comfort levels and tissue damage levels.

Figure 4A:
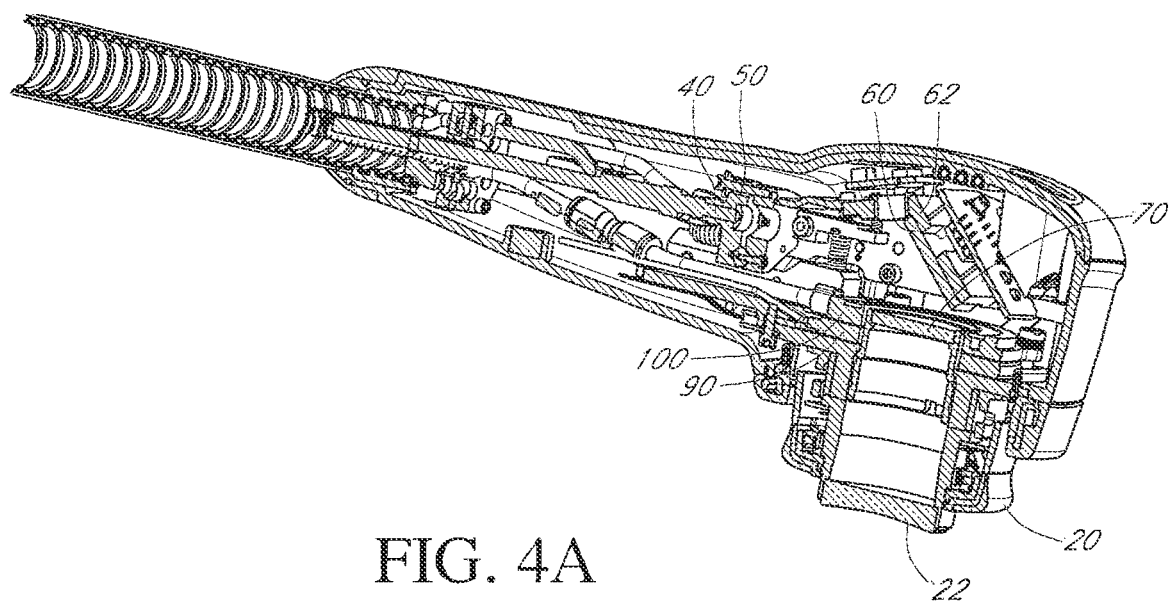
FIGS. 4A and 4B schematically illustrate cross-sectional views of two example beam delivery apparatuses in accordance with certain embodiments described herein.
Figure 4B:
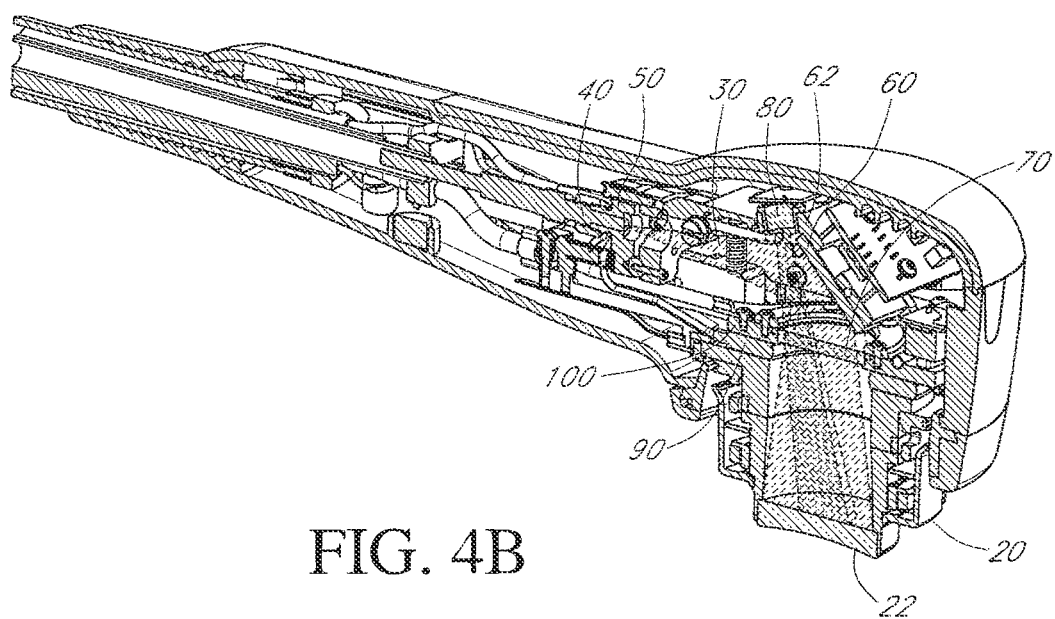

FIGS. 4A and 4B schematically illustrate cross-sectional views of two example beam delivery apparatuses 10 in accordance with certain embodiments described herein. In FIGS. 4A and 4B, the apparatus 10 comprises an output optical assembly 20 having an emission surface 22 and releasably operatively coupled to the other components of the apparatus 10. The apparatus 10 comprises an optical fiber 40, a fiber alignment mechanism 50 operatively coupled to the optical fiber 40, a mirror 60 in optical communication with the optical fiber 40, and a window 70 in optical communication with the mirror 60. During operation of the apparatus 10, light 30 from the optical fiber 40 propagates to the mirror 60 and is reflected by the mirror 60 to propagate through the window 70. The light 30 transmitted through the window 70 propagates through the output optical assembly 20 along a first optical path and is emitted from the emission surface 22. In certain embodiments, the apparatus 10 comprises additional optical elements (e.g., lenses, diffusers, and/or waveguides) which transmit at least a portion of the light received via the optical fiber 40 to the emission surface 22. In certain such embodiments, the additional optical elements of the apparatus 10 shape, format, or otherwise modify the light such that the light beam emitted from the emission surface 22 has the desired beam intensity profile.

In certain embodiments, the optical fiber 40 comprises a step-index or graded-index optical fiber. The optical fiber 40 of certain embodiments is single-mode, while in certain other embodiments, the optical fiber is multimode. An example optical fiber 40 compatible with certain embodiments described herein has a 1000-micron diameter and a numerical aperture of approximately 0.22.

Figure 5:
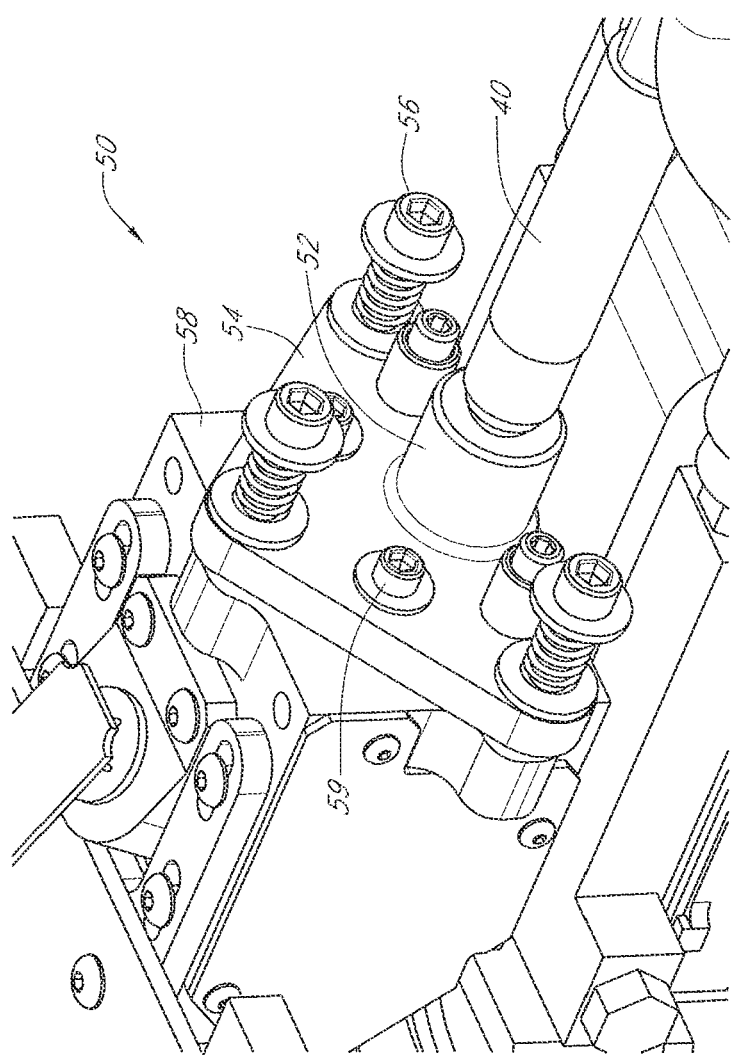
FIG. 5 schematically illustrates an example fiber alignment mechanism in accordance with certain embodiments described herein.

FIG. 5 schematically illustrates an example fiber alignment mechanism 50 in accordance with certain embodiments described herein. In certain embodiments, the fiber alignment mechanism 50 is mechanically coupled to a portion of the optical fiber 40 and is configured to allow adjustments of the position, tilt, or both of the end of the optical fiber 40 from which the light is emitted. In certain embodiments, the fiber alignment mechanism 50 provides an adjustment range of at least ±5 degrees. The fiber alignment mechanism 50 of FIG. 5 comprises a connector 52 (e.g., SMA connector) mechanically coupled to the optical fiber 40, a plate 54 (e.g., a kinematic tilt stage) mechanically coupled to the connector 52, and a plurality of adjustment screws 56 (e.g., 80 turns per inch or 100 turns per inch) adjustably coupled to the plate 54. By turning the adjustment screws 56, a distance between a portion of the plate 54 and a corresponding portion of a reference structure 58 can be adjusted. In certain embodiments, the fiber alignment mechanism 50 comprises one or more locking screws 59 configured to be tightened so as to fix the plate 54 at a position, orientation, or both relative to the reference structure 58. Other configurations of the fiber alignment mechanism 50 are also compatible with certain embodiments described herein.

Figure 6:
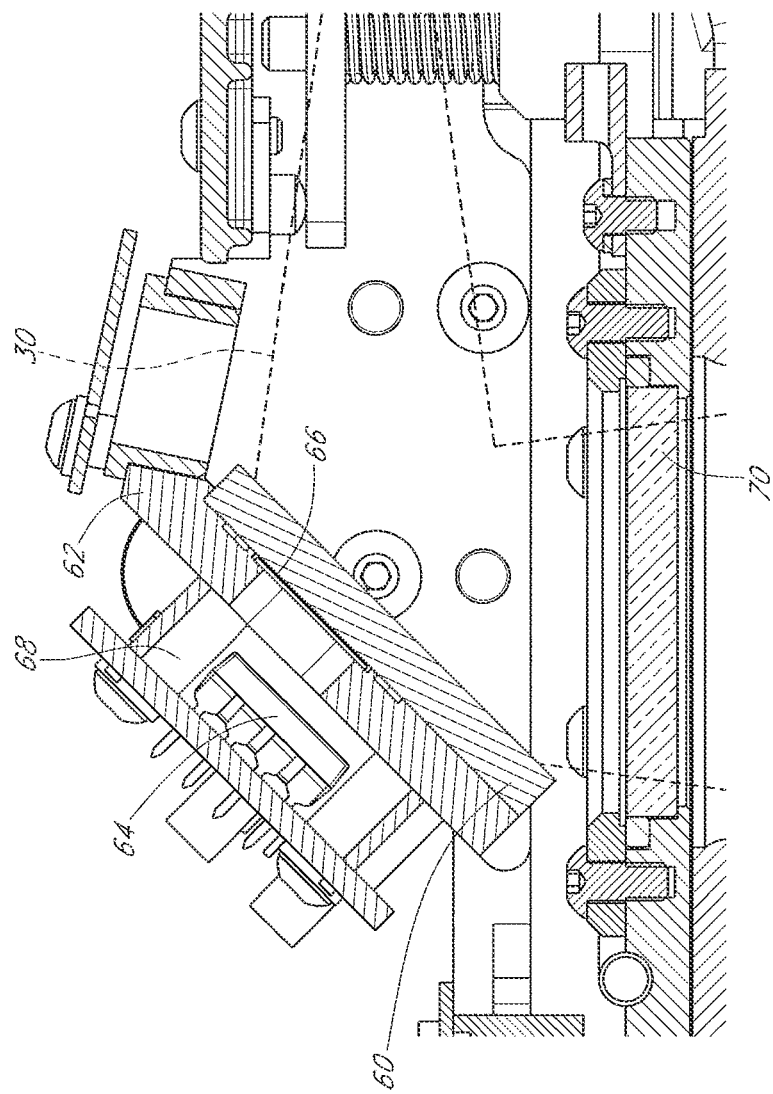
FIG. 6 schematically illustrates an example mirror compatible with certain embodiments described herein.

FIG. 6 schematically illustrates an example mirror 60 compatible with certain embodiments described herein. In certain embodiments, the mirror 60 is substantially reflective of light emitted from the optical fiber 40 to reflect the light through a non-zero angle (e.g., 90 degrees). The mirror 60 of certain embodiments comprises a glass substrate coated on at least one side by a metal (e.g., gold or aluminum). Examples of mirrors 60 compatible with certain embodiments described herein include, but are not limited to, a flat, generally planar glass mirror (e.g., NT43-886 available from Edmund Optics Inc. of Barrington, New Jersey). The mirror 60 of certain embodiments can be configured to have an optical power (e.g., the mirror 60 can be concave) and be adapted to shape, format, or otherwise modify the light to produce a desired beam intensity profile. In certain embodiments, the mirror 60 is bonded around its perimeter by an adhesive (e.g., OP-29 adhesive available from Dymax Corp. of Torrington, Connecticut) to a support structure 62.

In certain embodiments, the mirror 60 is partially transmissive of light emitted from the optical fiber 40. In certain such embodiments, the support structure 62 comprises an opening and the apparatus 10 comprises at least one light sensor 64 positioned to receive light transmitted through the mirror 60 and the opening of the support structure 62. The at least one light sensor 64 is configured to generate a signal indicative of the intensity of the received light, thereby providing a measure of the intensity of the light reaching the mirror 60. Examples of light sensors 64 compatible with certain embodiments described herein include, but are not limited to, OPT101 photodiode available from Texas Instruments of Dallas, Texas. In certain embodiments, a plurality of light sensors 64 are used to provide operational redundancy to confirm that light with a sufficient intensity for operation of the apparatus 10 is being provided by the optical fiber 40. In certain embodiments, a diffuser 66 is positioned to diffuse the light transmitted through the mirror 60 before the light impinges the light sensor 64. In certain embodiments, the light sensor 64 is protected from stray light by an opaque shroud 68 generally surrounding the light sensor 64.

In certain embodiments, the window 70 is substantially transmissive to infrared radiation. Example windows 70 compatible with certain embodiments described herein include, but are not limited to, a flat, generally planar CaF$_2$ window (e.g., TechSpec® calcium fluoride window available from Edmund Optics Inc. of Barrington, New Jersey).

In certain embodiments, the window 70 at least partially bounds a region within the apparatus 10 which contains the mirror 60. The window 70 of certain such embodiments substantially seals the region against contaminants (e.g., dust, debris) from entering the region from outside the region. For example, when the output optical assembly 20 is decoupled from the apparatus 10, the window 70 controls, inhibits, prevents, minimizes, or reduces contaminants entering the region. Thus, by virtue of the window 70 substantially sealing the region, the contamination of the region is lower than it would otherwise be if the window 70 did not substantially seal the region.

Figure 7:
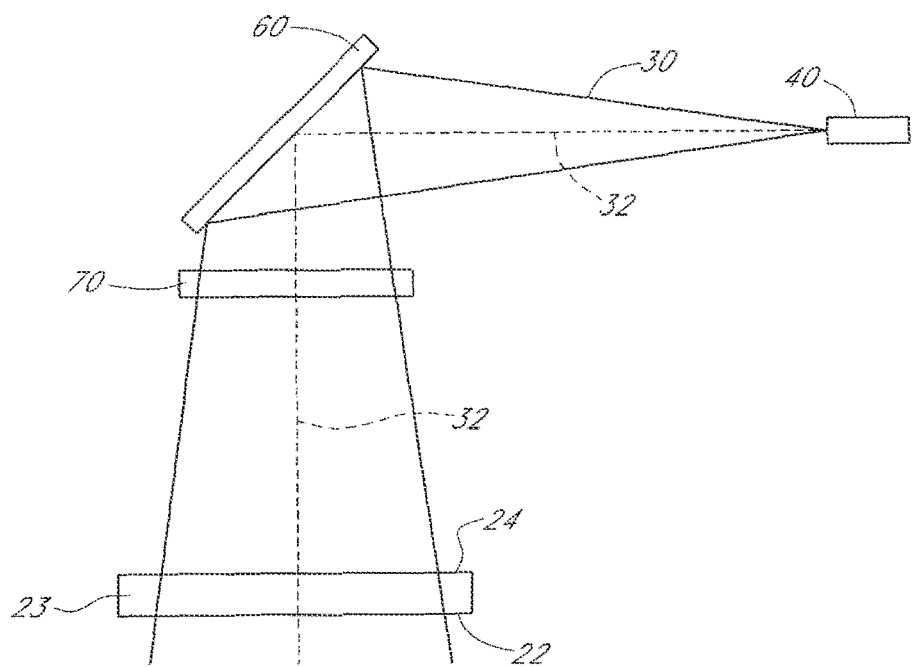
FIG. 7 schematically illustrates an example first optical path of light emitted from the optical fiber in accordance with certain embodiments described herein.

FIG. 7 schematically illustrates an example first optical path 32 of light 30 emitted from the optical fiber 40 in accordance with certain embodiments described herein. The diverging light 30 exiting the optical fiber 40 propagates along the first optical path 32 towards the mirror 60. The light 30 is reflected by the mirror 60 and propagates along the first optical path 32 through the window 70, impinges or is received by the surface 24 of the optical element 23, and is emitted from the emission surface 22 towards the surface to be irradiated. In certain embodiments, the mirror 60 reflects the light 30 through an angle of about 90 degrees. In certain embodiments, the mirror 60 is about 2.3 inches from the face of the optical fiber 40 and the first optical path 32 is about 4.55 inches in length from the fiber output face to the emission surface 22 of the optical element 23.

Figure 8:
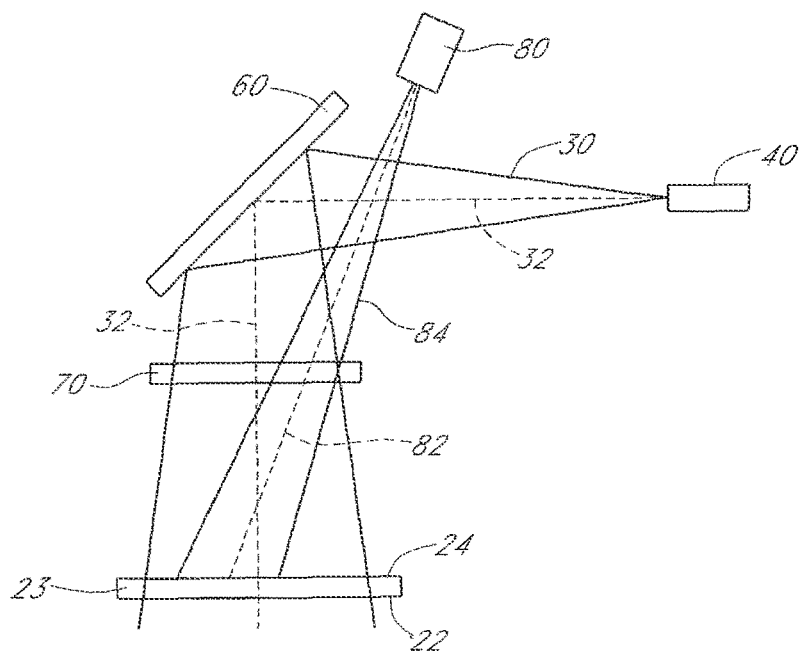
FIG. 8 schematically illustrates an example second optical path of radiation received by the sensor.

In certain embodiments, the apparatus 10 further comprises a sensor 80 spaced from the output optical assembly 20. FIG. 8 schematically illustrates an example second optical path 82 of radiation 84 received by the sensor 80. The sensor 80 is positioned to receive the radiation 84 from the output optical assembly 20 propagating through the output optical assembly 20 along the second optical path 82. The first optical path 32 and the second optical path 82 have a non-zero angle therebetween. In certain embodiments, the second optical path 82 is co-planar with the first optical path 32, while in certain other embodiments, the first optical path 32 and the second optical path 82 are non-co-planar with one another. The sensor 80 of certain embodiments receives radiation 84 propagating along the second optical path 82 from at least a portion of the surface 24 of the optical element 23 during operation of the apparatus 10.

The sensor 80 of certain embodiments comprises a temperature sensor (e.g., thermopile) configured to receive infrared radiation from a region and to generate a signal indicative of the temperature of the region. Examples of temperature sensors compatible with certain embodiments described herein include, but are not limited to, DX-0496 thermopile available from Dexter Research Center, Inc. of Dexter, Michigan. In certain embodiments, the field-of-view of the sensor 80 comprises an area of about 0.26 square inches of the surface 24 spaced from the thermal conduit 25 (e.g., by a distance between 0.05 inch and 0.3 inch). In certain other embodiments, the field-of-view of the sensor 80 comprises an area of about 0.57 square inches of the surface 24.

In certain embodiments, the sensor 80 is responsive to the received radiation 84 by generating a signal indicative of a temperature of the skin or of a portion of the output optical assembly 20 (e.g., the optical element 23). In certain such embodiments, the apparatus 10 further comprises a controller configured to receive the signal from the sensor 80 and to cause a warning to be generated, to turn off a source of the light propagating along the first optical path 32, or both in response to the signal indicating that the temperature is above a predetermined threshold temperature (e.g., 42 degrees Celsius).

The sensor 80 of certain embodiments is not in thermal communication with the output optical assembly 20. As shown in FIG. 8, the infrared-transmissive window 70 is between the sensor 80 and the output optical assembly 20. The light 30 propagating along the first optical path 32 and the infrared radiation 84 propagating along the second optical path 82 both propagate through the window 70. In certain embodiments, the sensor 80 is wholly or at least partially within a region of the housing 12 at least partially bound, and substantially sealed by the window 70 against contaminants from entering the region from outside the region.

In certain embodiments, the apparatus 10 is adapted to cool the irradiated portion of the scalp by removing heat from the scalp so as to control, inhibit, prevent, minimize, or reduce temperature increases at the scalp. Thus, by virtue of the apparatus 10 cooling the irradiated portion of the patient's scalp, the temperature of the irradiated portion of the patient's scalp is lower than it would otherwise be if the apparatus 10 did not cool the irradiated portion of the scalp. For example, by cooling the irradiated portion of the patient's scalp using the apparatus 10, the temperature of the irradiated portion of the patient's scalp can be higher than the temperature of the portion of the patient's scalp if it were not irradiated, but lower than the temperature of the portion of the patient's scalp if it were irradiated but not cooled. Referring to FIGS. 4A and 4B, in certain embodiments, the apparatus 10 comprises a thermoelectric assembly 90 and a heat sink 100 in thermal communication with the thermoelectric assembly 90. In certain embodiments, the thermoelectric assembly 90 actively cools the patient's skin via the output optical assembly 20, thereby advantageously avoiding large temperature gradients at the patient's skin which would otherwise cause discomfort to the patient. In certain embodiments, the apparatus 10 further comprises one or more temperature sensors (e.g., thermocouples, thermistors) which generate electrical signals indicative of the temperature of the thermoelectric assembly 90.

In certain embodiments, the thermoelectric assembly 90 comprises at least one thermoelectric element 91 and a thermal conduit 92. The at least one thermoelectric element 91 of the thermoelectric assembly 90 is responsive to an electric current applied to the thermoelectric assembly 90 by cooling at least a first surface 93 of the thermoelectric assembly 90 and heating at least a second surface 94 of the thermoelectric assembly 90. The thermoelectric assembly 90 is configured to be releasably mechanically coupled to the output optical assembly 20 so as to have the first surface 93 in thermal communication with the output optical assembly 20. In certain embodiments, the first surface 93 comprises a surface of the thermal conduit 92 and the second surface 94 comprises a surface of the thermoelectric element 91.

Figure 9A:
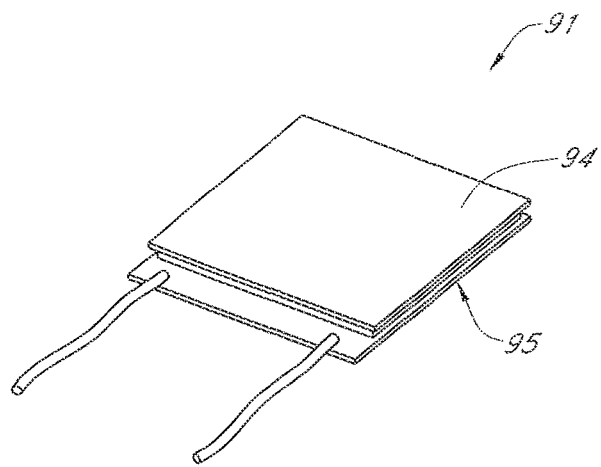
FIG. 9A schematically illustrates an example thermoelectric element and FIG. 9B schematically illustrates two views of an example thermal conduit in accordance with certain embodiments described herein.
Figure 9B:
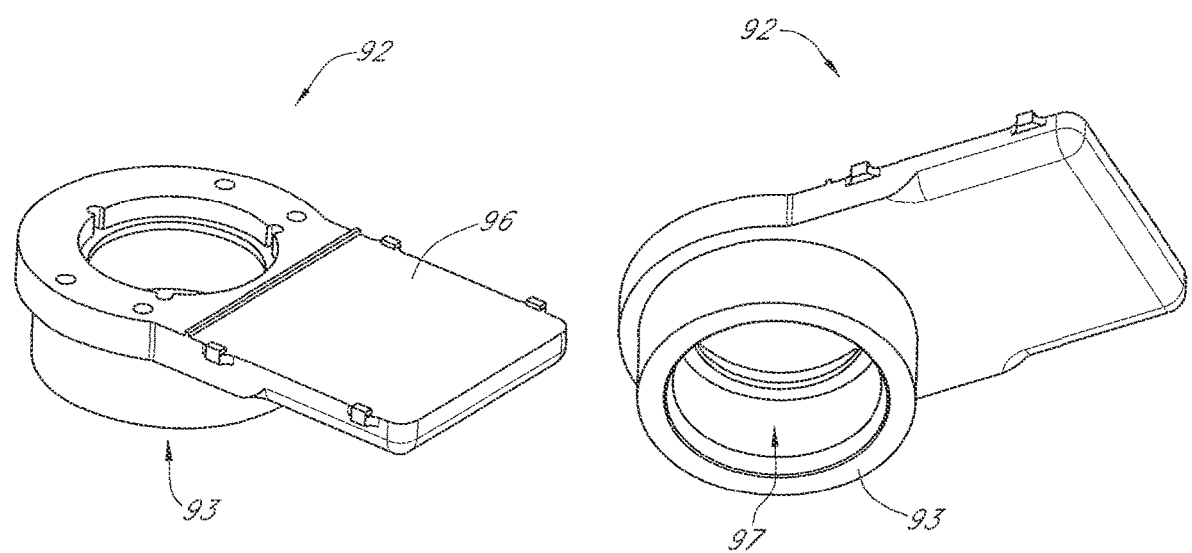
Figure 10A:
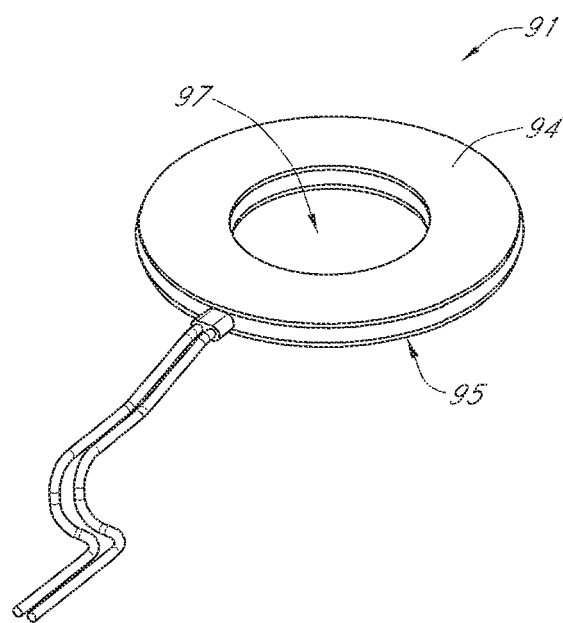
FIG. 10A schematically illustrates another example thermoelectric element and FIG. 10B schematically illustrates two views of another example thermal conduit in accordance with certain embodiments described herein.
Figure 10B:
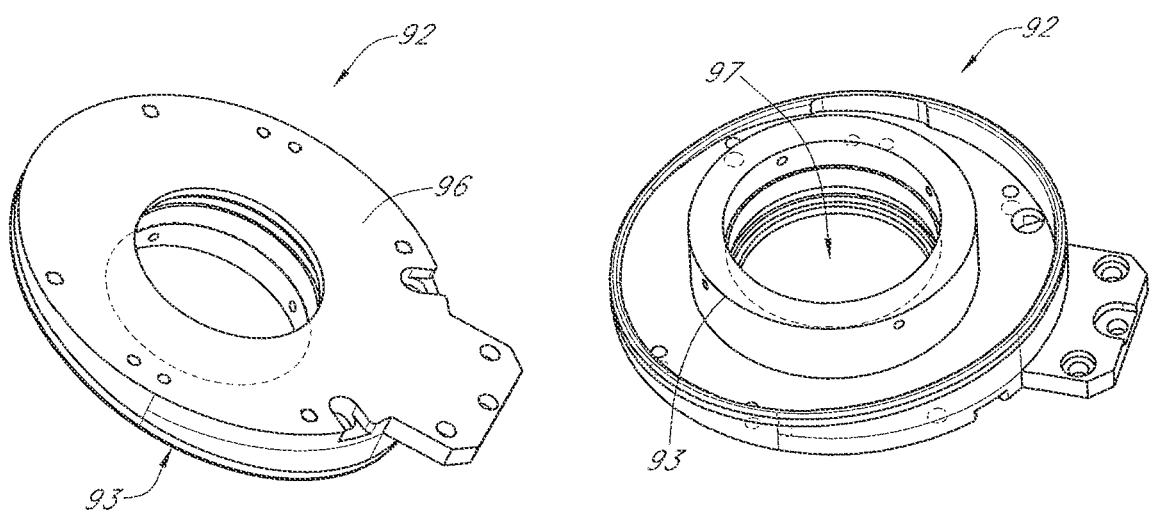

FIG. 9A schematically illustrates an example thermoelectric element 91 and FIG. 9B schematically illustrates two views of an example thermal conduit 92 in accordance with certain embodiments described herein. FIG. 10A schematically illustrates another example thermoelectric element 91 and FIG. 10B schematically illustrates two views of another example thermal conduit 92 in accordance with certain embodiments described herein. The thermoelectric element 91 has a surface 95 configured to be in thermal communication with a corresponding surface 96 of the thermal conduit 92 (e.g., by a thermally conductive adhesive). Upon application of an electric current to the thermoelectric element 91, the second surface 94 is heated and the surface 95 is cooled, thereby cooling the first surface 93. In certain such embodiments, the first surface 93 serves as at least one heat dissipating surface of the apparatus 10 configured to be in thermal communication with the at least one surface 26 of the thermal conduit 25 of the output optical assembly 20 (e.g., by contacting or mating so as to provide a thermally conductive connection between the thermoelectric assembly 26 and the output optical assembly 20). By having the thermally conductive output optical assembly 20 in thermal communication with the thermoelectric assembly 90, certain embodiments advantageously provide a conduit for heat conduction away from the treatment site (e.g., the skin). In certain embodiments, the output optical assembly 20 is pressed against the patient's skin and transfers heat away from the treatment site.

Examples of thermoelectric elements 91 compatible with certain embodiments described herein include, but are not limited to, DT12-6, $Q_{max}$=60 W, square thermoelectric element available from Marlow Industries of Dallas, Texas, and $Q_{max}$=45 W toroidal- or donut-shaped thermoelectric element from Ferrotec Corp. of Bedford, New Hampshire. In certain embodiments, the thermoelectric element 91 removes heat from the output optical assembly 20 at a rate in a range of about 0.1 Watt to about 5 Watts or in a range of about 1 Watt to about 3 Watts. Example temperature controllers for operating the thermoelectric assembly 90 in accordance with certain embodiments described herein include, but are not limited to, MPT-5000 available from Wavelength Electronics, Inc. of Bozeman, Montana. Example materials for the thermal conduit 92 compatible with certain embodiments described herein include, but are not limited to, aluminum and copper. The thermal conduit 92 of certain embodiments has a thermal mass in a range of about 30 grams to about 70 grams, and has a thermal length between surface 93 and surface 96 in a range of about 0.5 inch to about 3.5 inches.

In certain embodiments, the thermoelectric assembly 90 generally surrounds a first region 97, wherein, during operation of the apparatus 10, light irradiating a portion of the patient's skin propagates through the first region 97. As shown in FIGS. 9B and 10B, in certain embodiments, the first region 97 comprises an aperture through the thermal conduit 92. As shown in FIG. 10B, the first region 97 in certain embodiments further comprises an aperture through the thermoelectric element 91. In certain embodiments, the thermoelectric assembly 90 comprises a plurality of thermoelectric elements 91 which are spaced from one another and are distributed to generally surround the first region 97. As used herein, the term "generally surrounds" has its broadest reasonable interpretation, including but not limited to, encircles or extends around at least one margin of the region, or being distributed around at least one margin of the region with one or more gaps along the at least one margin.

Figure 11A:
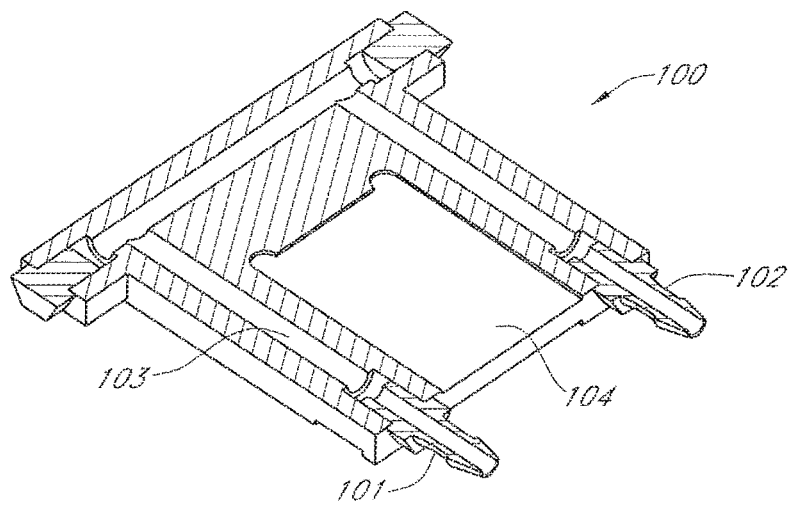
FIG. 11A schematically illustrates a cross-sectional view of an example heat sink and FIG. 11B schematically illustrates another example heat sink in accordance with certain embodiments described herein.
Figure 11B:
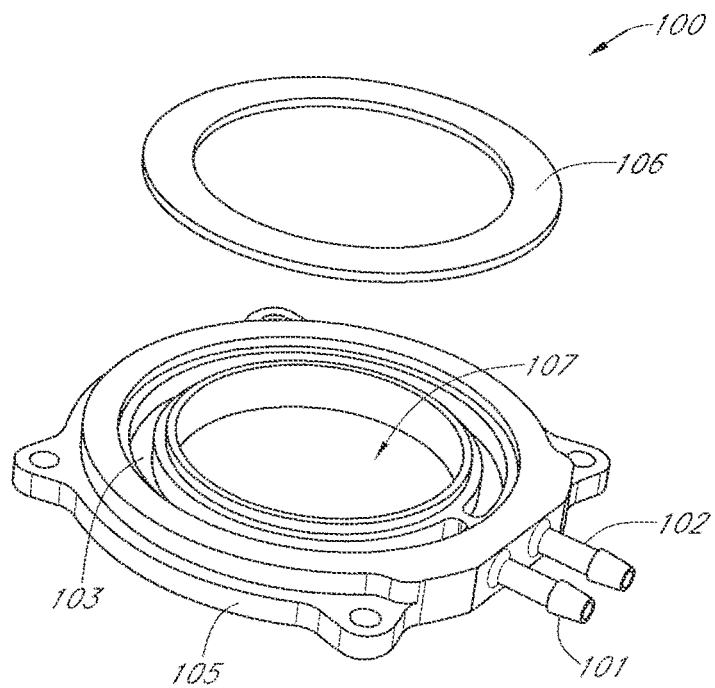

FIG. 11A schematically illustrates a cross-sectional view of an example heat sink 100 and FIG. 11B schematically illustrates another example heat sink 100 in accordance with certain embodiments described herein. The heat sink 100 comprises an inlet 101, an outlet 102, and a fluid conduit 103 in fluid communication with the inlet 101 and the outlet 102. The inlet 101 and the outlet 102 of certain embodiments comprise stainless steel barbs configured to be connected to tubes (e.g., using nylon or stainless steel hose barb locks, clamps, or crimps) which provide a coolant (e.g., water, air, glycerol) to flow through the fluid conduit 103 and to remove heat from the fluid conduit 103. In certain embodiments, the coolant is provided by a chiller or other heat transfer device which cools the coolant prior to its being supplied to the heat sink 100.

The example heat sink 100 of FIG. 11A is machined from an aluminum block and has a recess 104 in which the thermoelectric assembly 90 is placed to provide thermal communication between the heat sink 100 and the second surface 94 of the thermoelectric assembly 90. The example heat sink 100 of FIG. 11B comprises a first portion 105 and a second portion 106 which fit together to form the coolant conduit 103. In certain embodiments, a thermally conductive adhesive (e.g., EP1200 thermal adhesive available from Resinlab, LLC of Germantown, Wisconsin, with a 0.005-inch stainless steel wire to set the bondline) is used to bond the thermoelectric assembly 90 and the heat sink 100 together in thermal communication with one another.

The output optical assembly 20 comprises a thermally conductive thermal conduit 25 having at least one surface 26 configured to be in thermal communication with the first surface of the thermoelectric assembly 90. As shown in FIGS. 2A and 2B, the thermal conduit 25 generally surrounds a second region 28. During operation of the apparatus 10, the light propagates through the first region 97, the second region 28, and the optical element 23. In certain embodiments, the heat sink 100 generally surrounds a third region 107, as schematically illustrated by FIG. 11B. During operation of the apparatus 10 in certain such embodiments, the light propagates through the third region 107, the first region 97, the second region 28, and the optical element 23.

Figure 12A:
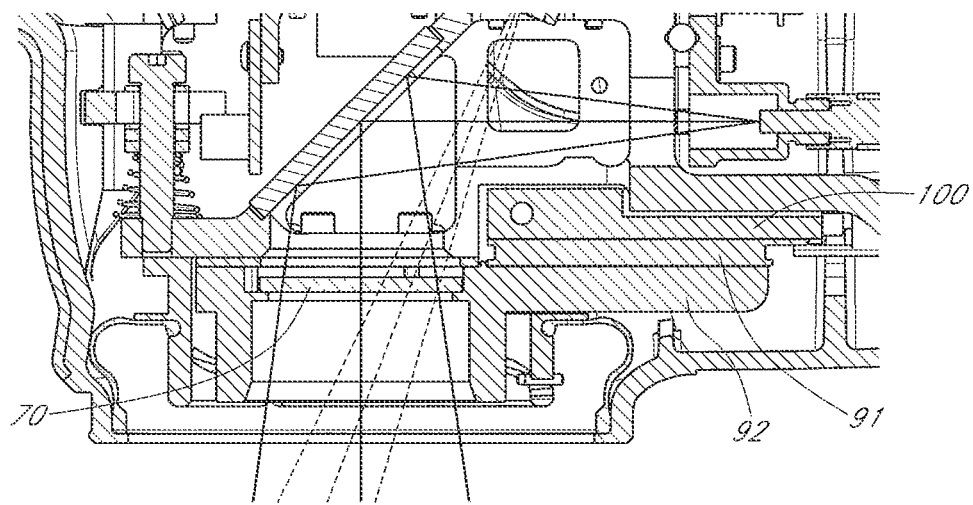
FIGS. 12A and 12B schematically illustrate two example configurations of the window with the thermoelectric assembly.
Figure 12B:
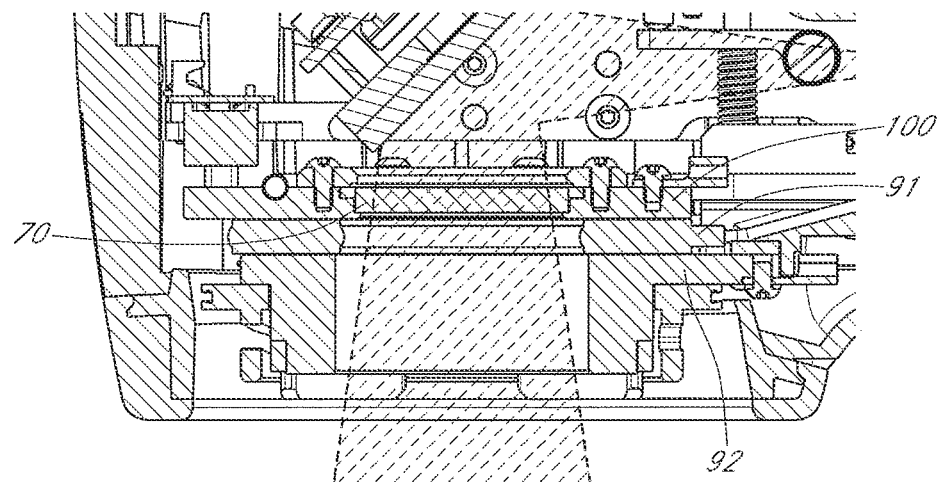

FIGS. 12A and 12B schematically illustrate two example configurations of the window 70 with the thermoelectric assembly 90. In certain embodiments, the window 70 is in thermal communication with at least a portion of the thermoelectric assembly 90 (e.g., bonded to a recess in the thermal conduit 92, as shown in FIG. 12A, using OP-29 adhesive available from Dymax Corp. of Torrington, Connecticut). In certain embodiments, the window 70 is in thermal communication with at least a portion of the heat sink 100 (e.g., retained by an o-ring in the heat sink 100), as shown in FIG. 12B. In certain embodiments, the window 70 is not in thermal communication with either the thermoelectric assembly 90 or the heat sink 100.

Figure 13A:
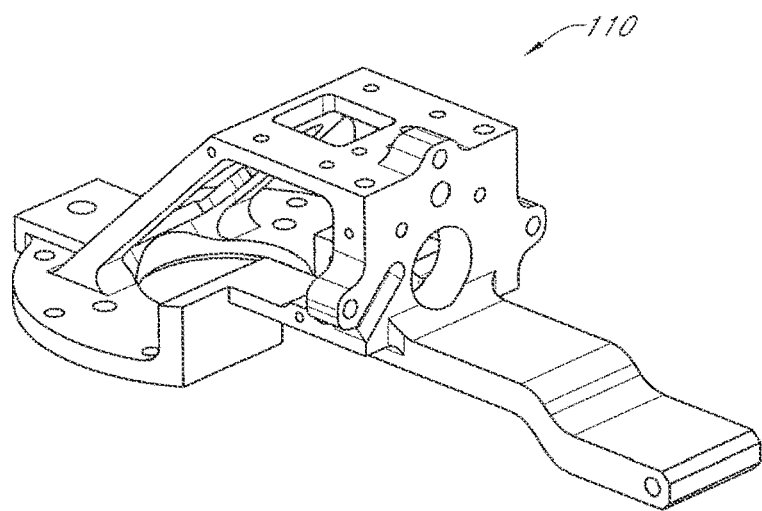
FIG. 13A schematically illustrates an example chassis for supporting the various components of the beam delivery apparatus within the housing in accordance with certain embodiments described herein.
Figure 13B:
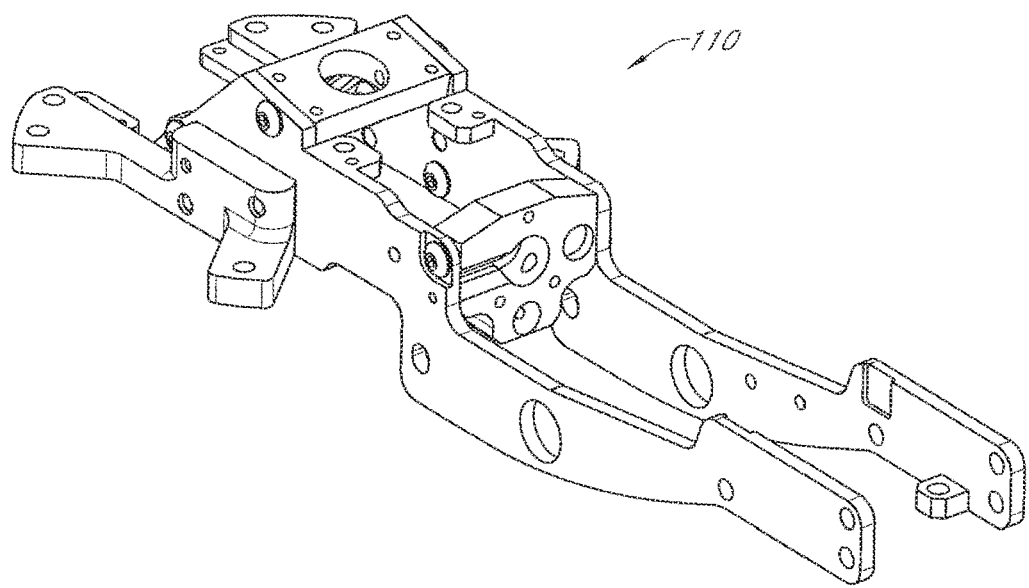
FIG. 13B schematically illustrates another example chassis in accordance with certain embodiments described herein.

FIG. 13A schematically illustrates an example chassis 110 for supporting the various components of the beam delivery apparatus 10 within the housing 12 in accordance with certain embodiments described herein. The chassis 110 of FIG. 13A comprises a single unitary or monolithic piece which is machined to provide various surfaces and holes used to mount the various components of the beam delivery apparatus 10. FIG. 13B schematically illustrates another example chassis 110 in accordance with certain embodiments described herein. The chassis 110 of FIG. 13B comprises a plurality of portions which are bolted or pinned together.

Figure 14A:
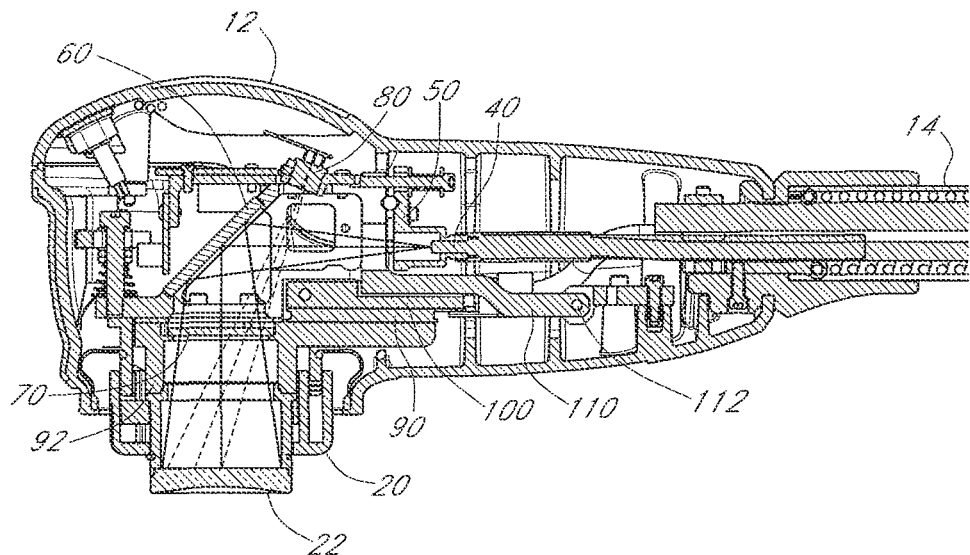
FIG. 14A schematically illustrates a cross-sectional view of an example configuration of the chassis and the housing in accordance with certain embodiments described herein.

FIG. 14A schematically illustrates a cross-sectional view of an example configuration of the chassis 110 and the housing 12 in accordance with certain embodiments described herein. The chassis 110 of certain embodiments is electrically connected to ground, while in certain other embodiments, the chassis 110 is electrically insulated from ground (e.g., floating). In certain embodiments, the chassis 110 is configured to move relative to the housing 12. For example, the chassis 110 and the housing 12 are mechanically coupled together by a pivot 112, as schematically illustrated by FIG. 14A. The optical fiber 40, fiber adjustment apparatus 50, mirror 60, window 70, sensor 80, and heat sink 100 are each mechanically coupled to the chassis 110. The output optical assembly 20 is also mechanically coupled to the chassis 110 via the thermoelectric assembly 90 and the heat sink 100.

For the configuration of FIG. 14A, the emission surface 22 of the output optical assembly 20 is placed in thermal communication (e.g., in contact) with the patient's scalp by a user pressing the housing 12 towards the scalp. The pivot 112 allows the chassis 110 to rotate about the pivot 112 relative to the housing 12 (e.g., by an angle between 1 and 2 degrees, or about 1.75 degrees) such that the emission surface 22 moves towards the housing 12 (e.g., by a distance of 0.05-0.3 inch, or about 0.1 inch). In certain such embodiments, this movement of the chassis 110, as well as of the fiber adjustment apparatus 50 and the optical fiber 40, results in a flexing of a portion of the optical fiber 40 (e.g., in proximity to the coupling between the housing 12 and the conduit 14).

Figure 14B:
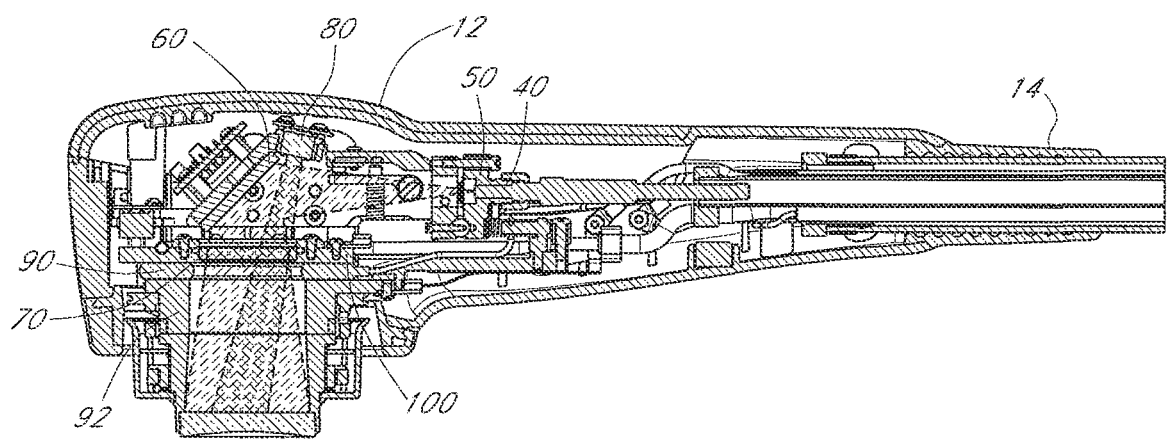
FIGS. 14B and 14C schematically illustrate another example configuration of the chassis and the housing in accordance with certain embodiments described herein.
Figure 14C:
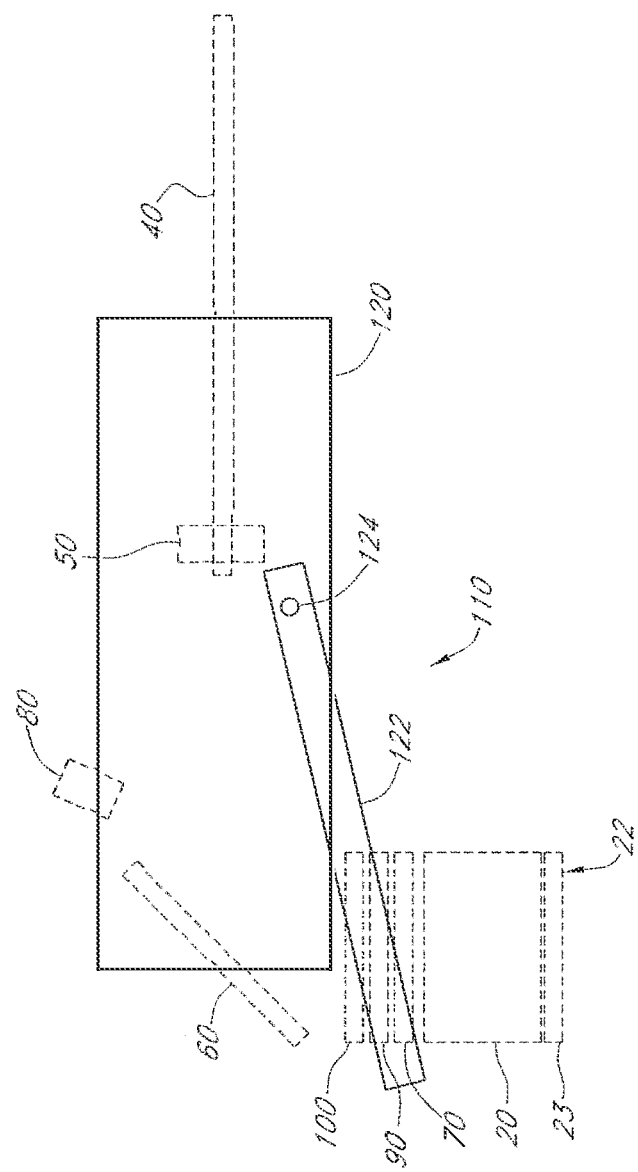

This flexing of the optical fiber 40 can be undesirable in certain circumstances, such as when the optical fiber 40 or its connection to the fiber adjustment apparatus 50 is fragile and prone to breakage or failure due to repeated flexing. FIGS. 14B and 14C schematically illustrate another example configuration of the chassis 110 and the housing 12 in accordance with certain embodiments described herein. The chassis 110 comprises a first chassis element 120 and a second chassis element 122 mechanically coupled to the first chassis element 120 such that the first chassis element 120 and the second chassis element 122 can move relative to one another. For example, in certain embodiments, the apparatus 10 further comprises a hinge 124 (e.g., a pivot or flexible portion) about which the first chassis element 120 and the second chassis element 122 are configured to deflect relative to one another.

In certain embodiments, the first chassis element 120 is mechanically coupled to the housing 12, and the optical fiber 40, fiber adjustment apparatus 50, mirror 60, and sensor 80 (each shown in dotted lines in FIG. 14C) are mechanically coupled to the first chassis element 120. The second chassis element 122 is mechanically coupled to the window 70, thermoelectric assembly 90, and the heat sink 100 (each shown in dotted lines in FIG. 14C). The output optical assembly 20 is also mechanically coupled to the second chassis element 122 via the thermoelectric assembly 90 and the heat sink 100. Thus, in certain such embodiments, a first portion of the apparatus 10 comprises the housing 12, first chassis element 120, optical fiber 40, fiber adjustment apparatus 50, mirror 60, and sensor 80, and a second portion of the apparatus 10 comprises the second chassis element 122, window 70, thermoelectric assembly 90, heat sink 100, and output optical assembly 20. The second portion is mechanically coupled to the first portion and is in optical communication with the first portion. The second portion is configured to be placed in thermal communication with the patient's skin such that the light from the first portion propagates through the second portion during operation of the apparatus 10. The first portion and the second portion are configured to move relative to one another in response to the second portion being placed in thermal communication with the patient's skin.

In certain embodiments, the second portion comprises the output optical assembly 20 and the first portion and the second portion are configured to deflect relative to one another by a non-zero angle. In certain embodiments, this deflection occurs upon the output optical assembly 20 applying a pressure to a portion of the patient's scalp sufficient to at least partially blanch the portion of the patient's scalp. In certain embodiments, this deflection occurs upon the output optical assembly 20 being placed in thermal communication with the patient's skin. In certain embodiments, the apparatus 10 further comprises a spring mechanically coupled to the first portion and the second portion. The spring provides a restoring force in response to movement of the first portion and the second portion relative to one another.

For the configuration of FIGS. 14B and 14C, the emission surface 22 of the output optical assembly 20 is placed in thermal communication (e.g., in contact) with the patient's scalp by a user pressing the housing 12 towards the scalp. The hinge 124 allows the second portion (e.g., including the second chassis element 122) to rotate about the hinge 124 relative to the first portion (e.g., including the first chassis element 120). This rotation can be by an angle between 1 and 3 degrees, or about 2.3 degrees such that the emission surface 22 moves towards the housing 12 (e.g., by a distance of 0.05-0.3 inch, or about 0.08 inch). In certain such embodiments in which the first portion comprises the optical fiber 40, deflection of the first portion and the second portion relative to one another controls, inhibits, prevents, minimizes, or reduces flexing or movement of the optical fiber 40 (e.g., to control, inhibit, prevent, minimize, or reduce damage to the optical fiber 40). Thus, by virtue of the movement of the first and second portions relative to one another, the flexing, movement, or damage of the optical fiber 40 is lower than it would otherwise be if the first and second portions did not move relative to one another.

In certain embodiments, the relative movement of the output optical assembly 20 and the mirror 60 can result in the light beam 30 being at least partially occluded or "clipped" by the thermal conduit 25 of the output optical assembly 20. For example, for a light beam diameter of 30 millimeters, the light beam 30 is not clipped by the thermal conduit 25. For larger light beam diameters, the light beam 30 is partially occluded by the thermal conduit 25. For a light beam diameter of 31 millimeters, about 0.02% of the light beam area is occluded, and for 32 millimeters, about 1.56% of the light beam area is occluded, resulting in an estimated power loss of less than about 0.08%.

In certain embodiments, the apparatus 10 further comprises a sensor 130 configured to detect movement of the first portion and the second portion relative to one another (e.g., movement of the first chassis element 120 and the second chassis element 122 relative to one another). The sensor 130 is configured to transmit a signal to a controller configured to receive the signal and to control a light source in response to the signal, where the light source is configured to generate the light used by the apparatus 10 irradiate the patient's scalp. In certain embodiments, the sensor 130 transmits the signal to the controller upon detecting that the movement between the first portion and the second portion is larger than a predetermined threshold value. In this way, the sensor 130 serves as a trigger switch which is used to trigger the apparatus 10 (e.g., providing the apparatus 10 with light upon the sensor 130 detecting the predetermined amount of movement between the first portion and the second portion indicative of the apparatus 10 being in a condition for use). The trigger switch of certain embodiments is actuated by pressing the output optical assembly 20 against a surface. The light source providing light to the apparatus 10 is responsive to the trigger switch by emitting light only when the trigger switch is actuated. Therefore, in certain such embodiments, to utilize the apparatus 10, the output optical assembly 20 is pressed against the patient's skin, such as described above.

Figure 15A:
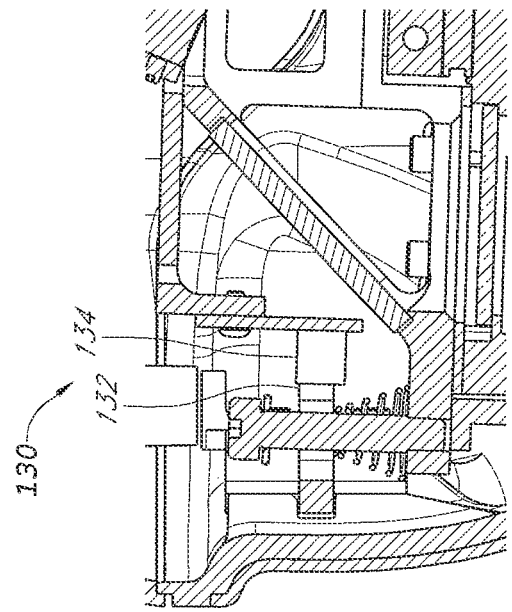
FIGS. 15A and 15B schematically illustrate two states of an example sensor in accordance with certain embodiments described herein.
Figure 15B:
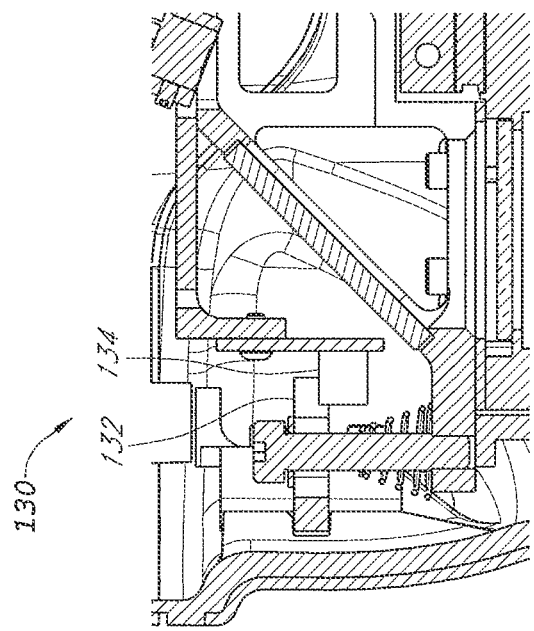

FIGS. 15A and 15B schematically illustrate two states of an example sensor 130 in accordance with certain embodiments described herein. The sensor 130 comprises at least one trigger flag 132 mechanically coupled to the first portion (e.g., the housing 12) and at least one optical switch 134 mechanically coupled to the second portion (e.g., the second chassis element 122). For example, the at least one optical switch 134 of certain embodiments comprises one, two, or more EE-SX-1035 optical switches available from Omron Electronics Components LLC of Schaumburg, Illinois. In a first state, the trigger flag 132 is displaced away from a sensor light beam which is detected by the optical switch 134. Upon pressing the output optical assembly 20 in thermal communication with the patient's scalp, the optical switch 134 moves relative to the trigger flag 132 (e.g., by a distance of about 0.07 inch) such that the trigger flag 132 intercepts the sensor light beam such that it is no longer detected by the optical switch 134. In response to this second state, the sensor 130 generates a corresponding signal. In certain other embodiments, the trigger flag 132 can be positioned to intercept the sensor light beam in the first state and to not intercept the sensor light beam in the second state.

Figure 15D:
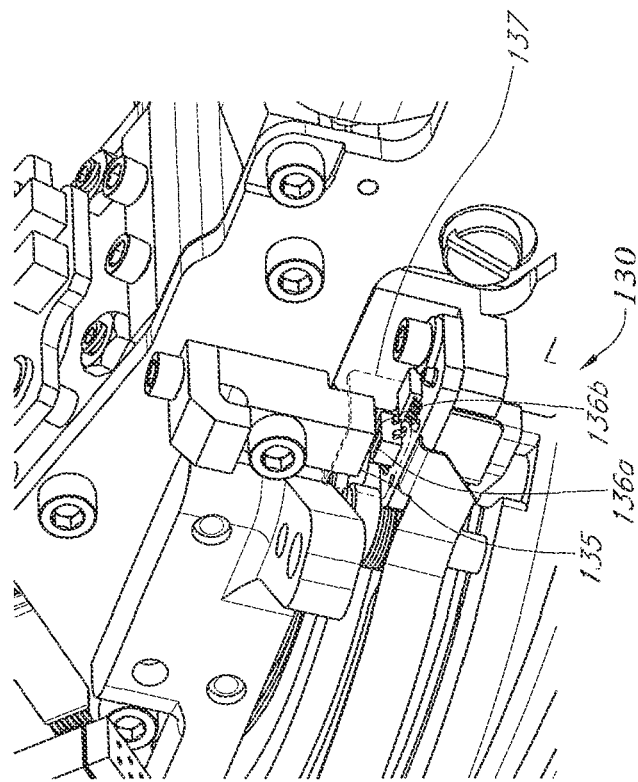
FIGS. 15C and 15D schematically illustrate two states of another example sensor in accordance with certain embodiments described herein.
Figure 15C:
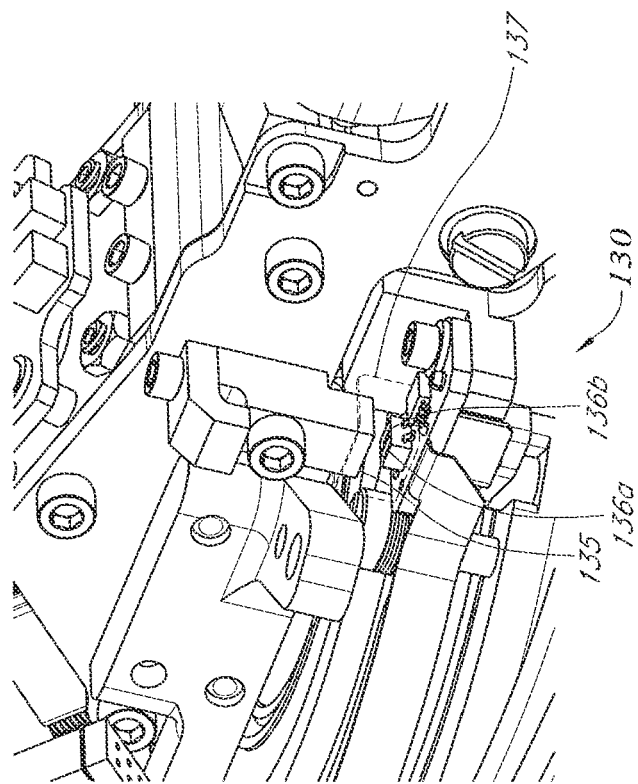

FIGS. 15C and 15D schematically illustrate two states of another example sensor 130 in accordance with certain embodiments described herein. The sensor 130 comprises a reflective element 135 mechanically coupled to the first portion (e.g., the first chassis element 120) and at least one light source/detector pair 136 mechanically coupled to the second portion (e.g., the second chassis element 122). For example, the at least one light source/detector pair 136a, 136b of certain embodiments comprises one, two, or more QRE1113GR reflective sensors available from Fairchild Semiconductor Corp. of San Jose, California. In a first state, the reflective surface 135 is a first distance away from the light source/detector pair 136a, 136b such that a sensor light beam from the source 136a is reflected from the surface 135 but is not detected by the detector 136b. Upon pressing the output optical assembly 20 in thermal communication with the patient's scalp, the reflective surface 135 moves (e.g., by a distance of about 0.04 inch) to be a second distance away from the light source/detector pair 136a, 136b such that the sensor light beam from the source 136a is reflected from the surface 135 and is detected by the detector 136b. In response to this second state, the sensor 130 generates a corresponding signal. In certain embodiments, the sensor 130 further comprises a shroud 137 configured to protect the detector 136b from stray light. In certain other embodiments, the reflective surface 135 can be positioned to reflect the sensor light beam to the detector 136b in the first state and to not reflect the sensor light beam to the detector 136b in the second state.

In certain embodiments, the apparatus 10 further comprises an adjustment mechanism configured to set the predetermined threshold value, to change the predetermined threshold value, or both. In certain such embodiments, the adjustment mechanism comprises a set screw which changes the relative positions of the two portions of the sensor 130 which move relative to one another. Certain embodiments further comprise a stop configured to limit a range of movement of the first portion and the second portion relative to one another.

Figure 16A:
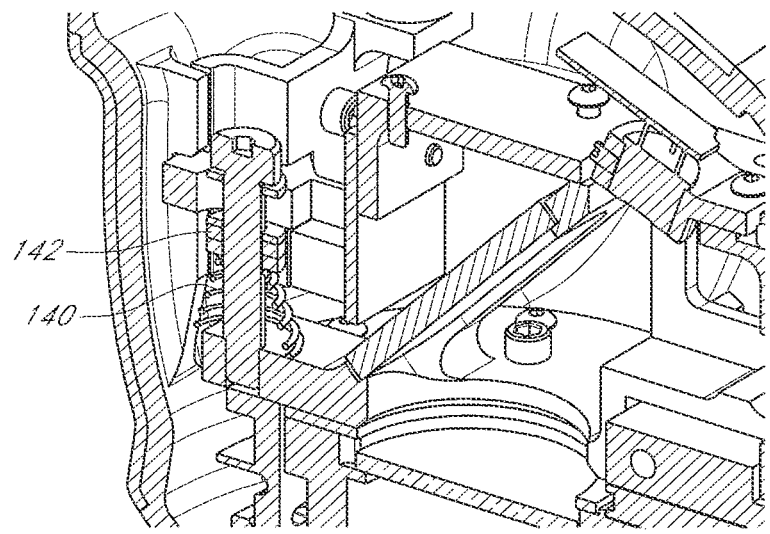
FIGS. 16A and 16B schematically illustrate two example configurations of the trigger force spring and trigger force adjustment mechanism in accordance with certain embodiments described herein.
Figure 16B:
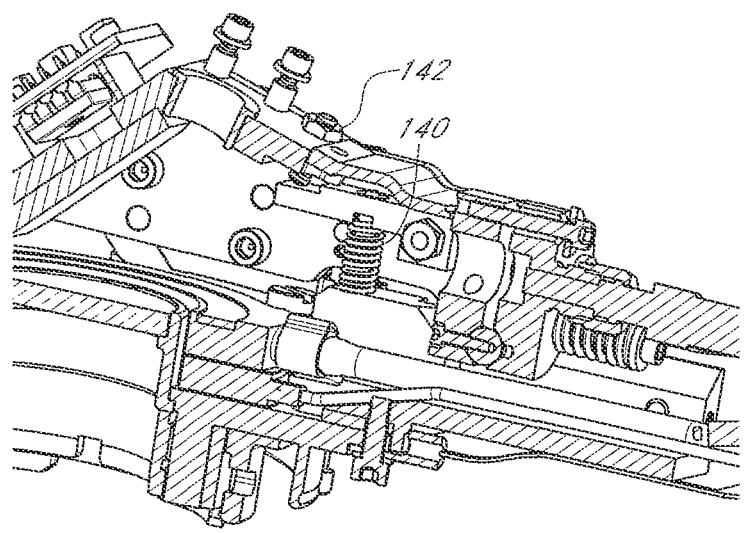

In certain embodiments, the apparatus 10 comprises a trigger force spring 140 and a trigger force adjustment mechanism 142. FIGS. 16A and 16B schematically illustrate two example configurations of the trigger force spring 140 and trigger force adjustment mechanism 142 in accordance with certain embodiments described herein. The trigger force spring 140 is mechanically coupled to the first portion (e.g., the first chassis element 120) and the second portion (e.g., the second chassis element 122) and provides a restoring force when the first portion and the second portion are moved relative to one another. The trigger force adjustment mechanism 142 of FIG. 16A comprises one or more shims (e.g., each shim providing about 100 grams of adjustment) placed between the spring 140 and at least one of the first portion and the second portion. The trigger force adjustment mechanism 142 of FIG. 16B comprises one, two, or more adjustment set screws. In either configuration, the trigger force adjustment mechanism 142 compresses the spring 140 to adjust the amount of force which will move the first and second portions relative to one another by a sufficient amount to trigger the apparatus 10. In certain embodiments, the trigger force adjustment mechanism 142 is set such that the apparatus 10 is triggered by a pressure applied to the emission surface 22 towards the housing 12 of at least 0.1 pound per square inch, at least one pound per square inch, or at least about two pounds per square inch.

Figure 17:
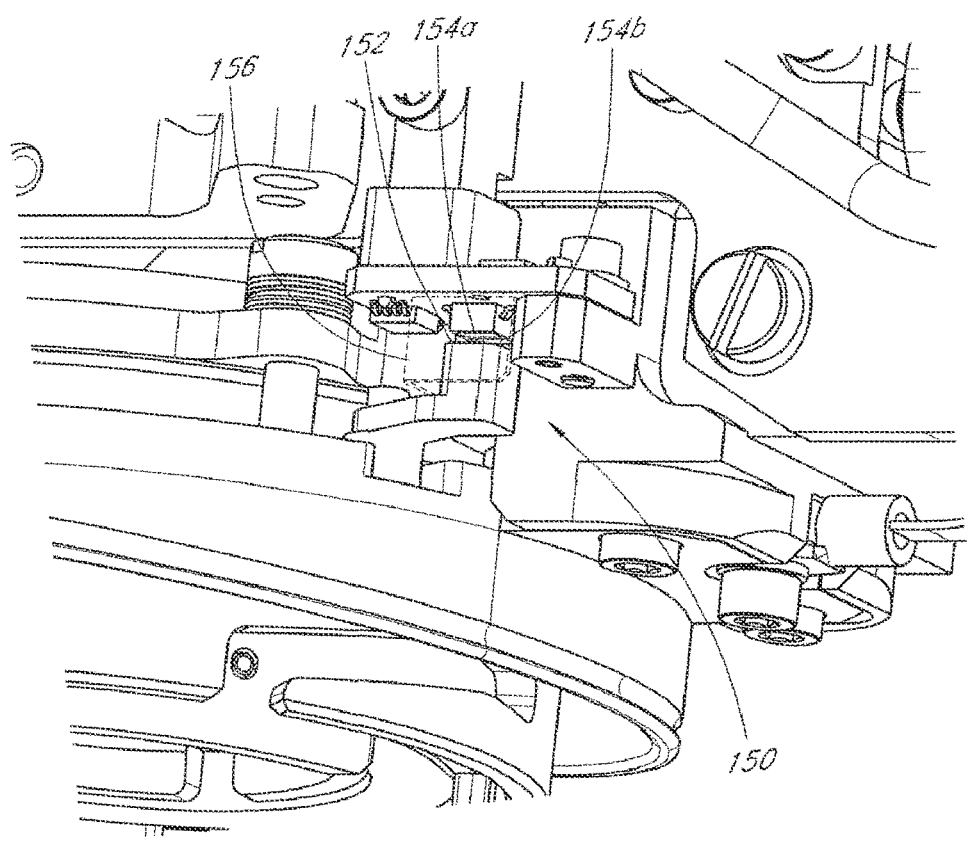
FIG. 17 schematically illustrates an example lens assembly sensor in accordance with certain embodiments described herein.

In certain embodiments, the apparatus 10 further comprises a lens assembly sensor 150 configured to detect the presence of the output optical assembly 20 mounted on the apparatus 10. FIG. 17 schematically illustrates an example lens assembly sensor 150 in accordance with certain embodiments described herein. For example, the lens assembly sensor 150 of certain embodiments comprises at least one reflective surface 152 and at least one light source/detector pair 154a, 154b (e.g., one, two, or more QRE1113GR reflective sensors available from Fairchild Semiconductor Corp. of San Jose, California). The reflective surface 152 moves relative to the light source/detector pair 154a, 154b upon mounting the output optical assembly 20 to be in thermal communication with the thermal conduit 92. For example, when the output optical assembly 20 is mounted, the bayonet is pulled downward. In response to this movement, the sensor 150 generates a corresponding signal. In certain embodiments, the sensor 150 further comprises a shroud 156 configured to protect the detector 154b from stray light.

Control Circuit

Figure 18:
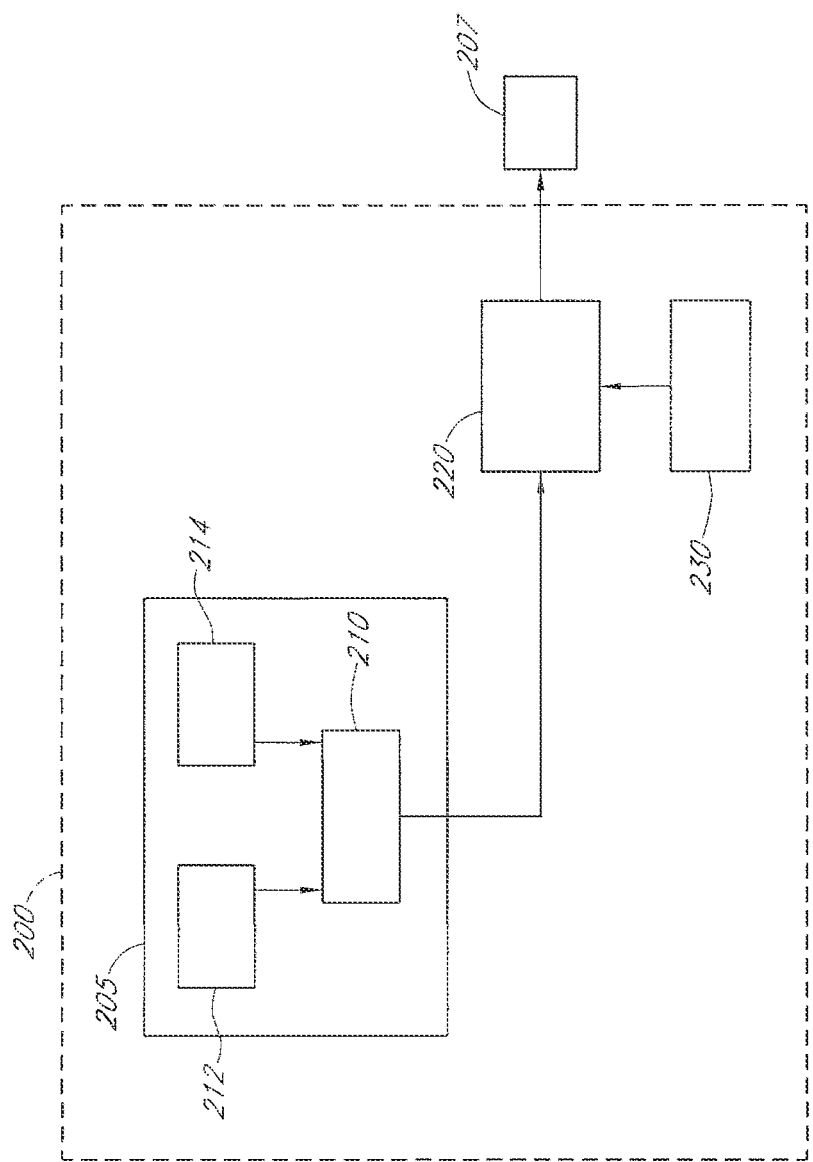
FIG. 18 is a block diagram of a control circuit comprising a programmable controller for controlling a light source according to embodiments described herein.

FIG. 18 is a block diagram of a control circuit 200 comprising a programmable controller 205 for controlling a light source 207 according to embodiments described herein. The control circuit 200 is configured to adjust the power of the light energy generated by the light source 207 such that the light emitted from the emission surface 22 generates a predetermined surface irradiance at the scalp corresponding to a predetermined energy delivery profile, such as a predetermined subsurface irradiance, to the target area of the brain.

In certain embodiments, the programmable controller 205 comprises a logic circuit 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the applied light. Examples of timing intervals include, but are not limited to, total treatment times, pulsewidth times for pulses of applied light, and time intervals between pulses of applied light. In certain embodiments, the light source 207 can be selectively turned on and off to reduce the thermal load on the scalp and to deliver a selected irradiance to particular areas of the brain.

The interface 214 of certain embodiments provides signals to the logic circuit 210 which the logic circuit 210 uses to control the applied light. The interface 214 can comprise a user interface or an interface to a sensor monitoring at least one parameter of the treatment. In certain such embodiments, the programmable controller 126 is responsive to signals from the sensor to preferably adjust the treatment parameters to optimize the measured response. The programmable controller 126 can thus provide closed-loop monitoring and adjustment of various treatment parameters to optimize the phototherapy. The signals provided by the interface 214 from a user are indicative of parameters that may include, but are not limited to, patient characteristics (e.g., skin type, fat percentage), selected applied irradiances, target time intervals, and irradiance/timing profiles for the applied light.

In certain embodiments, the logic circuit 210 is coupled to a light source driver 220. The light source driver 220 is coupled to a power supply 230, which in certain embodiments comprises a battery and in other embodiments comprises an alternating current source. The light source driver 220 is also coupled to the light source 207. The logic circuit 210 is responsive to the signal from the clock 212 and to user input from the user interface 214 to transmit a control signal to the light source driver 220. In response to the control signal from the logic circuit 210, the light source driver 220 adjust and controls the power applied to the light source. Other control circuits besides the control circuit 200 of FIG. 18 are compatible with embodiments described herein.

In certain embodiments, the logic circuit 110 is responsive to signals from a sensor monitoring at least one parameter of the treatment to control the applied light. For example, certain embodiments comprise a temperature sensor in thermal communication with the scalp to provide information regarding the temperature of the scalp to the logic circuit 210. In such embodiments, the logic circuit 210 is responsive to the information from the temperature sensor to transmit a control signal to the light source driver 220 so as to adjust the parameters of the applied light to maintain the scalp temperature below a predetermined level. Other embodiments include example biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit 210. In certain such embodiments, the logic circuit 110 is responsive to signals from the sensors to preferably adjust the parameters of the applied light to optimize the measured response. The logic circuit 110 can thus provide closed-loop monitoring and adjustment of various parameters of the applied light to optimize the phototherapy.

Light Parameters

The various parameters of the light beam emitted from the emission surface 22 are advantageously selected to provide treatment while controlling, inhibiting, preventing, minimizing, or reducing injury or discomfort to the patient due to heating of the scalp by the light. While discussed separately, these various parameters below can be combined with one another within the disclosed values in accordance with embodiments described herein.

Wavelength

In certain embodiments, light in the visible to near-infrared wavelength range is used to irradiate the patient's scalp. In certain embodiments, the light is substantially monochromatic (i.e., light having one wavelength, or light having a narrow band of wavelengths). So that the amount of light transmitted to the brain is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In certain other embodiments, the light comprises one or more wavelengths between about 630 nanometers and about 1064 nanometers, between about 780 nanometers and about 840 nanometers, between about 805 nanometers and about 820 nanometers, or includes wavelengths of about 785, 790, 795, 800, 805, 810, 815, 820, 825, or 830 nanometers. An intermediate wavelength in a range between approximately 730 nanometers and approximately 750 nanometers (e.g., about 739 nanometers) appears to be suitable for penetrating the skull, although other wavelengths are also suitable and may be used. In other embodiments, a plurality of wavelengths is used. In certain embodiments, the light has a wavelength distribution peaked at a peak wavelength and has a linewidth less than ±10 nanometers from the peak wavelength. In certain such embodiments, the light has a linewidth less than 4 nanometers, full width at 90% of energy. In certain embodiments, the center wavelength is (808±10) nanometers with a spectral linewidth les than 4 nanometers, full width at 90% of energy.

In certain embodiments, the light is generated by a light source comprising one or more laser diodes, which each provide coherent light. In embodiments in which the light from the light source is coherent, the emitted light may produce "speckling" due to coherent interference of the light. This speckling comprises intensity spikes which are created by wavefront interference effects and can occur in proximity to the target tissue being treated. For example, while the average irradiance or power density may be approximately 10 mW/cm², the power density of one such intensity spike in proximity to the brain tissue to be treated may be approximately 300 mW/cm². In certain embodiments, this increased power density due to speckling can improve the efficacy of treatments using coherent light over those using incoherent light for illumination of deeper tissues.

In certain embodiments, the light source includes at least one continuously emitting GaAlAs laser diode having a wavelength of about 830 nanometers. In another embodiment, the light source comprises a laser source having a wavelength of about 808 nanometers. In still other embodiments, the light source includes at least one vertical cavity surface-emitting laser (VCSEL) diode. Other light sources compatible with embodiments described herein include, but are not limited to, light-emitting diodes (LEDs) and filtered lamps.

In certain embodiments, the one or more wavelengths are selected so as to work with one or more chromophores within the target tissue. Without being bound by theory or by a specific mechanism, it is believed that irradiation of chromophores increases the production of ATP in the target tissue and/or controls, inhibits, prevents, minimizes, or reduces apoptosis of the injured tissues, thereby producing beneficial effects, as described more fully below.

Some chromophores, such as water or hemoglobin, are ubiquitous and absorb light to such a degree that little or no penetration of light energy into a tissue occurs. For example, water absorbs light above approximately 1300 nanometers. Thus energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers.

Based on these broad assumptions, one can define an "IR window" into the body. Within the window, there are certain wavelengths that are more or less likely to penetrate. This discussion does not include wavelength dependent scattering effects of intervening tissues.

Figure 19A:
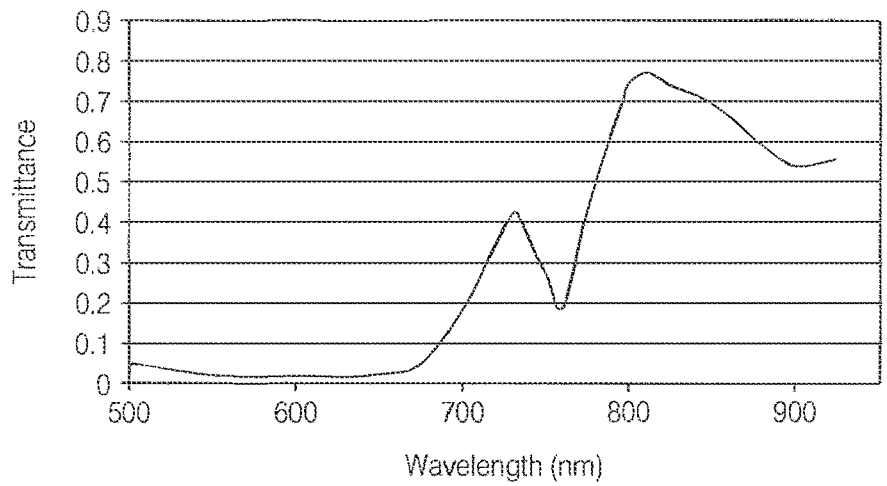
FIG. 19A is a graph of the transmittance of light through blood (in arbitrary units) as a function of wavelength.

The absorption/transmittance of various tissues have been directly measured to determine the utility of various wavelengths. FIG. 19A is a graph of the transmittance of light through blood (in arbitrary units) as a function of wavelength. Blood absorbs less in the region above 700 nanometers, and is particularly transparent at wavelengths above 780 nanometers. Wavelengths below 700 nanometers are heavily absorbed, and are not likely to be useful therapeutically (except for topical indications).

Figure 19B:
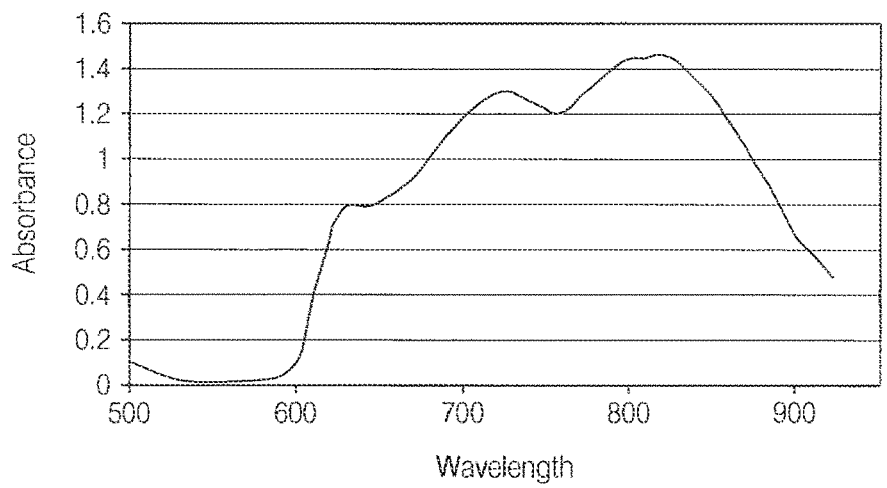
FIG. 19B is a graph of the absorption of light by brain tissue.

FIG. 19B is a graph of the absorption of light by brain tissue. Absorption in the brain is strong for wavelengths between 620 and 980 nanometers. This range is also where the copper centers in mitochondria absorb. The brain is particularly rich in mitochondria as it is a very active tissue metabolically (the brain accounts for 20% of blood flow and oxygen consumption). As such, the absorption of light in the 620 to 980 nanometer range is expected if a photostimulative effect is to take place.

Figure 19C:
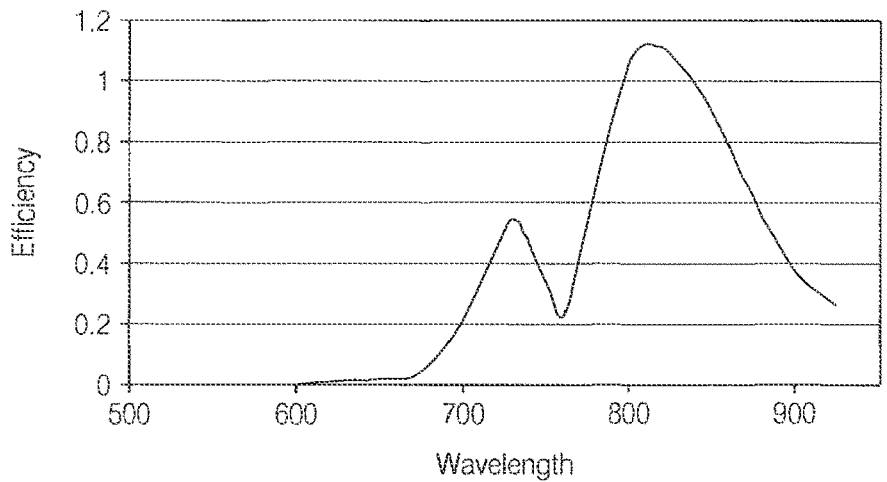
FIG. 19C shows the efficiency of energy delivery as a function of wavelength.

By combining FIGS. 19A and 19B, the efficiency of energy delivery as a function of wavelength can be calculated, as shown in FIG. 19C. Wavelengths between 780 and 880 nanometers are preferable (efficiency of 0.6 or greater) for targeting the brain. The peak efficiency is about 800 to 830 nanometers (efficiency of 1.0 or greater). These wavelengths are not absorbed by water or hemoglobin, and are likely to penetrate to the brain. Once these wavelengths reach the brain, they will be absorbed by the brain and converted to useful energy.

Figure 20:
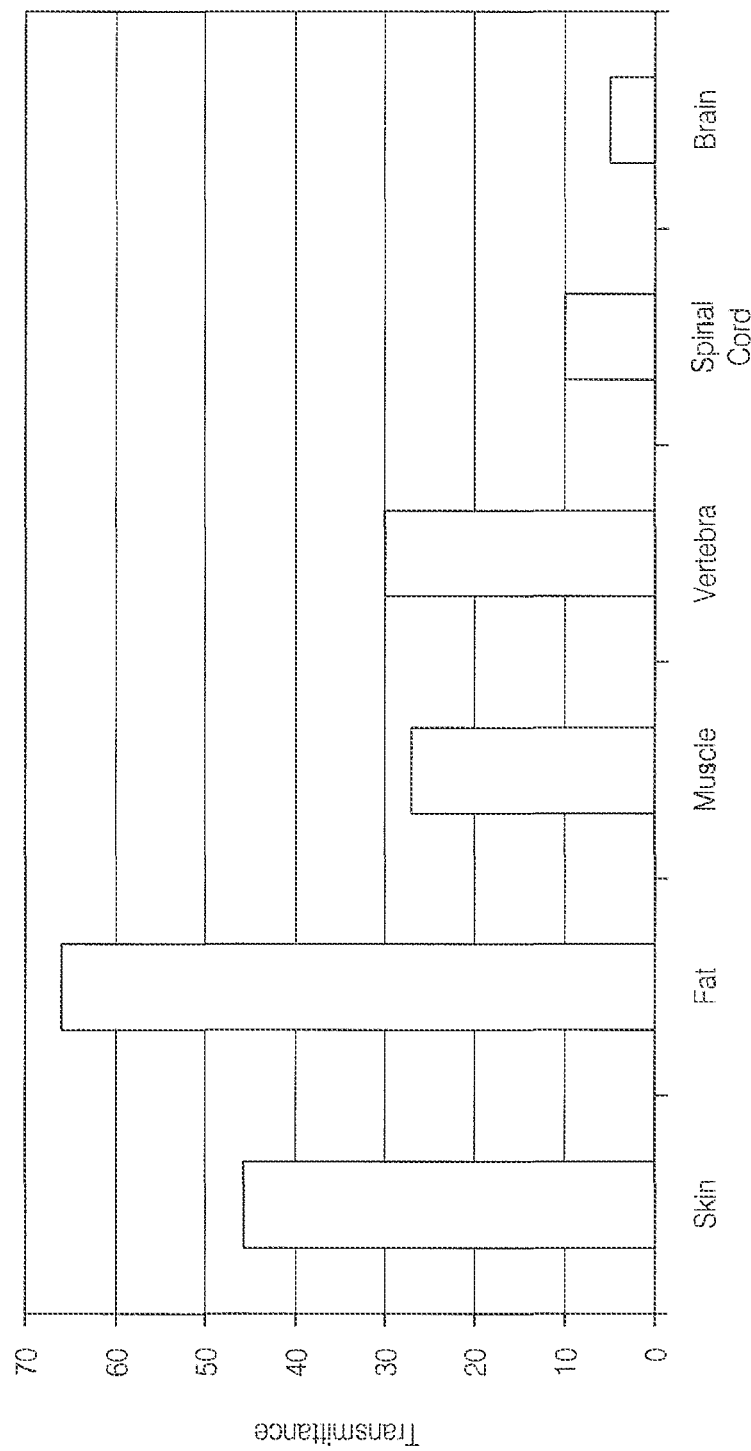
FIG. 20 shows measured absorption of 808 nanometer light through various rat tissues.

These effects have been directly demonstrated in rat tissues. The absorption of 808 nanometer light was measured through various rat tissues, as shown in FIG. 20. Soft tissues such as skin and fat absorb little light. Muscle, richer in mitochondria, absorbs more light. Even bone is fairly transparent. However, as noted above, brain tissue, as well as spinal cord tissue, absorb 808 nanometer light well.

Irradiance or Power Density

In certain embodiments, the light beam has a time-averaged irradiance or power density at the emission surface 22 of the output optical assembly 20 between about 10 mW/cm² to about 10 W/cm², between about 100 mW/cm² to about 1000 mW/cm², between about 500 mW/cm² to about 1 W/cm², or between about 650 mW/cm² to about 750 mW/cm² across the cross-sectional area of the light beam. The cross-sectional area of the light beam of certain embodiments (e.g., multimode beams) can be approximated using an approximation of the beam intensity distribution. For example, as described more fully below, measurements of the beam intensity distribution can be approximated by a Gaussian ($1/e^2$ measurements) or by a "top hat" distribution and a selected perimeter of the beam intensity distribution can be used to define a bound of the area of the light beam. In certain embodiments, the irradiance at the emission surface 22 is selected to provide the desired irradiances at the subdermal target tissue. The irradiance of the light beam is preferably controllably variable so that the emitted light energy can be adjusted to provide a selected irradiance at the subdermal tissue being treated. In certain embodiments, the light beam emitted from the emission surface 22 is continuous with a total radiant power in a range of about 4 Watts to about 6 Watts. In certain embodiments, the radiant power of the light beam is 5 Watts±20% (CW).

In certain embodiments, the irradiance at the subdermal target tissue (e.g., at a depth of approximately 2 centimeters below the dura) is at least about 0.01 mW/cm² and up to about 1 W/cm² at the level of the tissue. In various embodiments, the subsurface irradiance at the target tissue is at least about 0.01, 0.05, 0.1, 0.5, 1, 5, 10, 15, 20, 30, 40, 50, 60, 70, 80, or 90 mW/cm², depending on the desired clinical performance. In certain embodiments, the subsurface irradiance at the target tissue is about 0.01 mW/cm² to about 100 mW/cm², about 0.01 mW/cm² to about 50 mW/cm², about 2 mW/cm² to about 20 mW/cm², or about 5 mW/cm² to about 25 mW/cm².

In certain embodiments, the irradiance of the light beam is selected to provide a predetermined irradiance at the subdermal target tissue (e.g., at a depth of approximately 2 centimeters from the dura). The selection of the appropriate irradiance of the light beam emitted from the emission surface to use to achieve a desired subdermal irradiance preferably includes consideration of scattering by intervening tissue. Further information regarding the scattering of light by tissue is provided by U.S. Pat. No. 7,303,578, which is incorporated in its entirety by reference herein, and V. Tuchin in "Tissue Optics: Light Scattering Methods and Instruments for Medical Diagnosis," SPIE Press (2000), Bellingham, WA, pp. 3-11, which is incorporated in its entirety by reference herein.

Phototherapy for the treatment of stroke is based in part on the discovery that irradiance or power density (i.e., power per unit area or number of photons per unit area per unit time) and energy density (i.e., energy per unit area or number of photons per unit area) of the light energy applied to tissue appear to be significant factors in determining the relative efficacy of low level phototherapy. This discovery is particularly applicable with respect to treating and saving surviving but endangered neurons in a zone of danger surrounding the primary infarct after a stroke or cerebrovascular accident (CVA). Preferred methods described herein are based at least in part on the finding that, given a selected wavelength of light energy, it is the irradiance and/or the energy density of the light delivered to tissue (as opposed to the total power or total energy delivered to the tissue) that appears to be important factors in determining the relative efficacy of phototherapy.

Without being bound by theory or by a specific mechanism, it is believed that light energy delivered within a certain range of irradiances and energy densities provides the desired biostimulative effect on the intracellular environment, such that proper function is returned to previously nonfunctioning or poorly functioning mitochondria in at-risk neurons. The biostimulative effect may include interactions with chromophores within the target tissue, which facilitate production of ATP and/or controls, inhibits, prevents, minimizes, or reduces apoptosis of the injured cells which have experienced decreased blood flow due to the stroke. Because strokes correspond to blockages or other interruptions of blood flow to portions of the brain, it is thought that any effects of increasing blood flow by phototherapy are of less importance in the efficacy of phototherapy for stroke victims. Further information regarding the role of irradiance and exposure time is described by Hans H. F. I. van Breugel and P. R. Dop Bär in "Power Density and Exposure Time of He—Ne Laser Irradiation Are More Important Than Total Energy Dose in Photo-Biomodulation of Human Fibroblasts In Vitro," Lasers in Surgery and Medicine, Volume 12, pp. 528-537 (1992), which is incorporated in its entirety by reference herein.

In certain embodiments, delivering the neuroprotective amount of light energy includes selecting a surface irradiance of the light energy at the scalp corresponding to the predetermined irradiance at the target area of the brain. As described above, light propagating through tissue is scattered and absorbed by the tissue. Calculations of the irradiance to be applied to the scalp so as to deliver a predetermined irradiance to the selected target area of the brain preferably take into account the attenuation of the light energy as it propagates through the skin and other tissues, such as bone and brain tissue. Factors known to affect the attenuation of light propagating to the brain from the scalp include, but are not limited to, skin pigmentation, the presence, type, and color of hair over the area to be treated, amount of fat tissue, the presence of bruised tissue, skull thickness, patient's age and gender, and the location of the target area of the brain, particularly the depth of the area relative to the surface of the scalp. (For a general discussion of the absorption of light by melanins in the body, see, e.g., "Optical Absorption Spectra of Melanins—a Comparison of Theoretical and Experimental Results," accelrys.com/references/case-studies/melanins_partII.pdf.) The higher the level of skin pigmentation, the higher the irradiance applied to the scalp to deliver a predetermined irradiance of light energy to a subsurface site of the brain. The target area of the patient's brain can be previously identified such as by using standard medical imaging techniques.

The irradiance selected to be applied to the target area of the patient's brain depends on a number of factors, including, but not limited to, the wavelength of the applied light, the type of CVA (ischemic or hemorrhagic), and the patient's clinical condition, including the extent of the affected brain area. The irradiance power density of light energy to be delivered to the target area of the patient's brain may also be adjusted to be combined with any other therapeutic agent or agents, especially pharmaceutical neuroprotective agents, to achieve the desired biological effect. In such embodiments, the selected irradiance can also depend on the additional therapeutic agent or agents chosen.

Beam Size and Beam Profile

In certain embodiments, the light beam emitted from the output optical assembly 20 has a nominal diameter in a range of about 10 millimeters to about 40 millimeters, in a range of about 20 millimeters to about 35 millimeters, or equal to about 30 millimeters. In certain embodiments, the cross-sectional area is generally circular with a radius in a range of about 1 centimeter to about 2 centimeters. In certain embodiments, the light beam emitted from the emission surface 22 has a cross-sectional area greater than about 2 cm$^2$ or in a range of about 2 cm$^2$ to about 20 cm$^2$ at the emission surface 22 of the optical element 23. In certain embodiments, the output optical element 23 has an aperture diameter of less than 33 millimeters.

The perimeter of the light beam used to determine the diameter of the beam is defined in certain embodiments to be those points at which the intensity of the light beam is $1/e^2$ of the maximum intensity of the light beam. The maximum-useful diameter of certain embodiments is limited by the size of the patient's head and by the heating of the patient's head by the irradiation. The minimum-useful diameter of certain embodiments is limited by heating and by the total number of treatment sites that could be practically implemented. For example, to cover the patient's skull with a beam having a small beam diameter would correspondingly use a large number of treatment sites. In certain embodiments, the time of irradiation per treatment site can be adjusted accordingly to achieve a desired exposure dose.

Specifying the total flux inside a circular aperture with a specified radius centered on the exit aperture ("encircled energy") is a method of specifying the power (irradiance) distribution over the light beam emitted from the emission surface 22. The "encircled energy" can be used to ensure that the light beam is not too concentrated, too large, or too small. In certain embodiments, the light beam emitted from the emission surface has a total radiant power, and the light beam has a total flux inside a 20-millimeter diameter cross-sectional circle centered on the light beam at the emission surface 22 which is no more than 75% of the total radiant power. In certain such embodiments, the light beam has a total flux inside a 26-millimeter diameter cross-sectional circle centered on the light beam at the emission surface 22 which is no less than 50% of the total radiant power.

In certain embodiments, the beam intensity profile has a semi-Gaussian profile, while in certain other embodiments, the beam intensity profile has a "top hat" profile. In certain embodiments, the light beam is substantially without high flux regions or "hot spots" in the beam intensity profile in which the local flux, averaged over a 3 millimeter by 3 millimeter area, is more than 10% larger than the average flux. Certain embodiments of the apparatus 10 advantageously generate a light beam substantially without hot spots, thereby avoiding large temperature gradients at the patient's skin which would otherwise cause discomfort to the patient.

Divergence

In certain embodiments, the beam divergence emitted from the emission surface 22 is significantly less than the scattering angle of light inside the body tissue being irradiated, which is typically several degrees. In certain embodiments, the light beam has a divergence angle greater than zero and less than 35 degrees.

As the distance between a light source and an observer increases, the diameter of the source becomes less relevant to considerations of the beam divergence. For example, an end of the optical fiber 40 providing the light has a diameter of about 1 millimeter. At a close distance, observing from a specific location, light rays from the edges of the optical fiber end can arrive at the observation point with significantly different angles. However, as the observation point moves away from the light source, this angular discrepancy is reduced and the source appears more like a point source.

In certain embodiments, with the output optical assembly 20 mounted onto the apparatus 10, the optical distance between the emission surface 22 and the end of the optical fiber 40 is about 82.7 millimeters. The beam divergence dictated by the numerical aperture of the optical fiber 40 and the exit aperture of the optical element 23 is about 23 degrees. In certain embodiments, with the output optical assembly 20 not mounted onto the apparatus 10, the optical distance between the window 70 and the end of the optical fiber is about 57.5 millimeters, and the beam divergence dictated by the numerical aperture of the optical fiber 40 and the exit aperture of the window 70 is about 16 degrees. With a source diameter of about 1 millimeter, the angular ambiguity in the beam divergence is about +0.35 degree. Thus, the angular ambiguity is much less than the beam divergence angle regardless of whether the output optical assembly 20 is mounted or not onto the apparatus 10, so the optical fiber 40 can be treated as a point source. In certain such embodiments, the beam divergence or radiant intensity (e.g., measured in Watts/steradian) can be calculated directly from the beam profile or from the irradiance.

Treatment Time

In certain embodiments, the treatment per treatment site proceeds continuously for a period of about 10 seconds to about 2 hours, for a period of about 1 to about 10 minutes, or for a period of about 1 to 5 minutes. For example, the treatment time per treatment site in certain embodiments is about two minutes. In other embodiments, the light energy is delivered for at least one treatment period of at least about five minutes, or for at least one treatment period of at least ten minutes. The minimum treatment time of certain embodiments is limited by the biological response time (which is on the order of microseconds). The maximum treatment time of certain embodiments is limited by heating and by practical treatment times (e.g., completing treatment within about 24 hours of stroke onset). The light energy can be pulsed during the treatment period or the light energy can be continuously applied during the treatment period. If the light is pulsed, the pulses can be 2 milliseconds long and occur at a frequency of 100 Hz, although longer pulselengths and lower frequencies can be used, or at least about 10 nanosecond long and occur at a frequency of up to about 100 kHz.

In certain embodiments, the treatment may be terminated after one treatment period, while in other embodiments, the treatment may be repeated for at least two treatment periods. The time between subsequent treatment periods can be at least about five minutes, at least two in a 24-hour period, at least about 1 to 2 days, or at least about one week. The length of treatment time and frequency of treatment periods can depend on several factors, including the functional recovery of the patient and the results of imaging analysis of the infarct. In certain embodiments, one or more treatment parameters can be adjusted in response to a feedback signal from a device (e.g., magnetic resonance imaging) monitoring the patient.

Cooling Parameters

In certain embodiments, the apparatus 10 comprises an output optical element 23 in optical communication with a source of light. The output optical element 23 comprises an emission surface 22 configured to emit a light beam in accordance with the light parameters disclosed above. In certain embodiments the apparatus 10 further comprises a thermally conductive portion configured to be placed in thermal communication with the irradiated portion of the patient's scalp and to remove heat from the irradiated portion of the patient's scalp. In certain embodiments, the thermally conductive portion comprises the output optical element 23. The thermally conductive portion of certain embodiments is releasably coupled to the output optical element 23.

In certain embodiments, the thermally conductive portion removes heat from the irradiated portion of the patient's scalp. This cooling of the scalp can to improve the comfort of the patient, by controlling, inhibiting, preventing, minimizing, or reducing temperature increases at the scalp due to the irradiation. Thus, by virtue of the cooling of the portion of the patient's scalp being irradiated, the temperature of the irradiated portion of the patient's scalp is lower than it would otherwise be if the irradiated portion of the scalp were not cooled. For example, by cooling the irradiated portion of the patient's scalp, the temperature of the irradiated portion of the patient's scalp can be higher than the temperature of the portion of the patient's scalp if it were not irradiated, but lower than the temperature of the portion of the patient's scalp if it were irradiated but not cooled. In addition, this cooling of the scalp can be to perform double-blind studies of the efficacy of the phototherapy treatment by masking any heating of the scalp due to the irradiation. (See, e.g., B. Catanzaro et al., "Managing Tissue Heating in Laser Therapy to Enable Double-Blind Clinical Study," Mechanisms for Low-Light Therapy, Proc. of the SPIE, Vol. 6140, pp. 199-208 (2006).)

In certain embodiments, heat is removed from the irradiated portion of the patient's scalp by the thermally conductive portion at a rate in a range of about 0.1 Watt to about 5 Watts or in a range of about 1 Watt to about 3 Watts. In certain embodiments, the thermally conductive portion is configured to maintain the temperature of the irradiated portion of the patient's scalp to be less than 42 degrees Celsius. The thermally conductive portion of certain embodiments is in thermal communication with the emission surface 22 and is configured to maintain the temperature of the emission surface to be in a range of 18 degrees Celsius to 25 degrees Celsius under a heat load of 2 Watts. For a general description of cooling of the scalp, see, e.g., F. E. M. Janssen et al., "Modeling of temperature and perfusion during scalp cooling," Phys. Med. Biol., Vol. 50, pp. 4065-4073 (2005). In certain embodiments in which pulsed light is used, the rate of heat removal can be less, or cooling may not be utilized for certain ranges of pulsed dosimetries and timing.

Pressure Parameters

In certain embodiments, the apparatus 10 is configured to have the thermally conductive portion move relative to a second portion of the apparatus 10 upon a pressure being applied to the thermally conductive portion above a predetermined threshold pressure in a direction of movement of the thermally conductive portion relative to the second portion of the apparatus 10. The predetermined threshold pressure is sufficient to have the thermally conductive portion in thermal communication with the portion of the patient's scalp. In certain such embodiments, the apparatus 10 comprises a sensor configured to be responsive to the movement of the thermally conductive portion relative to the second portion by generating a signal (e.g., binary, analog, or digital) indicative of the movement.

In certain such embodiments, the sensor 130 in conjunction with the trigger force spring 140 and the trigger force adjustment mechanism 142 provides a mechanism for detecting whether the apparatus 10 is being applied to the patient's scalp with a pressure above the predetermined threshold pressure. In certain such embodiments, the sensor 130 detects movement between the first portion of the apparatus 10 and the second portion of the apparatus 10 upon placing the emission surface 22 in thermal communication with the patient's scalp with sufficient pressure to overcome the restoring force of the trigger force spring 140. Upon applying the threshold pressure to the emission surface 22 move the first and second portions relative to one another, the sensor 130 detects the movement and generates a corresponding signal. In certain embodiments, the apparatus 10 further comprises a controller operatively coupled to the light source and to the sensor 130. The controller is configured to receive the signal from the sensor 130 and to turn on the light source in response to the signal being indicative of the pressure being above the predetermined threshold pressure.

In certain embodiments, the threshold pressure is set to be a pressure which results in blanching of the portion of the patient's scalp to be irradiated. In certain embodiments, the threshold pressure is 0.1 pound per square inch, while in certain other embodiments, the threshold pressure is one pound per square inch or about two pounds per square inch. In certain embodiments in which pulsed light is used, the amount of blanching can be less, or blanching may not be utilized for certain ranges of pulsed dosimetries and timing.

Irradiating Multiple Portions of the Scalp

Figure 21A:
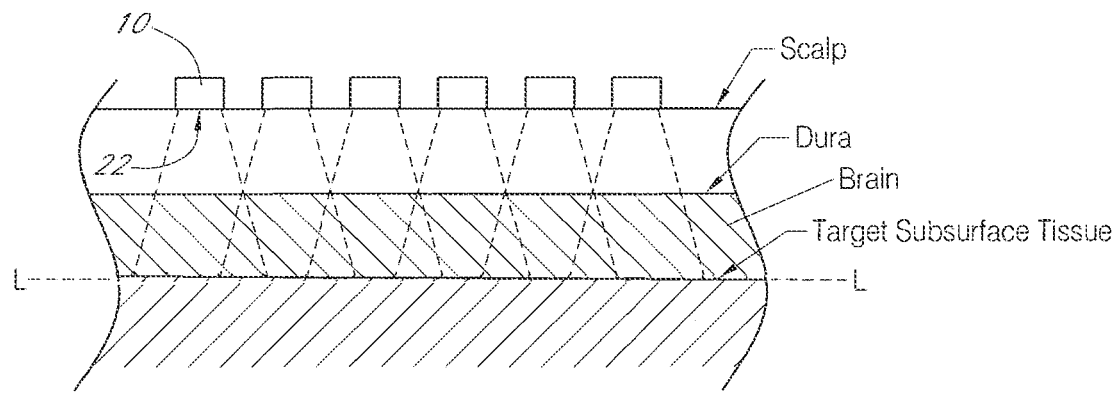
FIGS. 21A-21C schematically illustrate an embodiment in which the apparatus is placed in thermal communication sequentially with a plurality of treatment sites corresponding to portions of the patient's scalp.
Figure 21B:
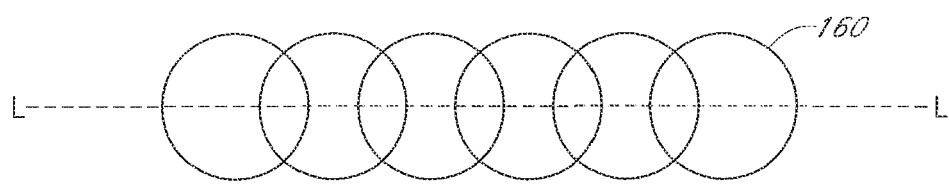
Figure 21C:
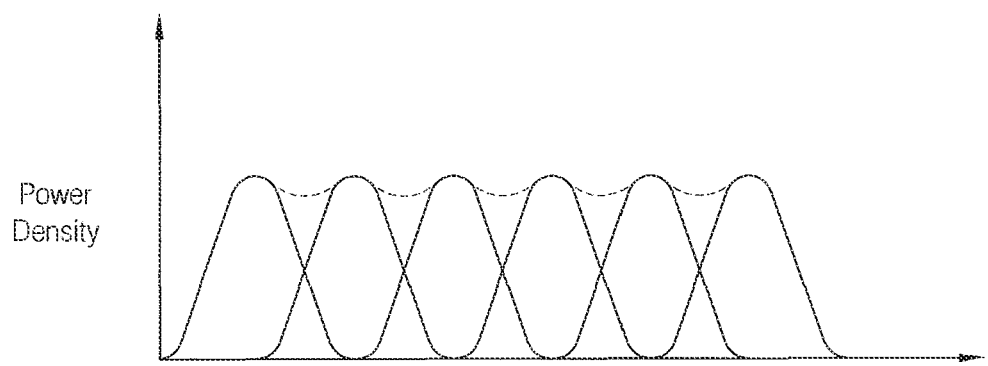

FIGS. 21A-21C schematically illustrate an embodiment in which the apparatus 10 is placed in thermal communication sequentially with a plurality of treatment sites corresponding to portions of the patient's scalp. In certain such embodiments, the light emitted from the emission surface 22 propagates through the scalp to the brain and disperses in a direction generally parallel to the scalp, as shown in FIG. 21A. In certain embodiments, the treatment sites of the patient's scalp do not overlap one another. The treatment sites (e.g., twenty treatment sites) are preferably spaced sufficiently far apart from one another such that the light emitted from the emission surface 22 to irradiate a treatment site of the patient's scalp is transmitted through intervening tissue to irradiate an area of the patient's brain which overlaps one or more areas of the target tissue of the patient's brain irradiated by the light emitted from the emission surface 22 when a neighboring treatment site of the patient's scalp is irradiated. FIG. 21B schematically illustrates this overlap as the overlap of circular spots 160 across the target tissue at a reference depth at or below the surface of the brain. FIG. 21C schematically illustrates this overlap as a graph of the irradiance at the reference depth of the brain along the line L-L of FIGS. 21A and 21B. Summing the irradiances from the neighboring treatment sites (shown as a dashed line in FIG. 21C) serves to provide a more uniform light distribution at the target tissue to be treated. In such embodiments, the summed irradiance is preferably less than a damage threshold of the brain and above an efficacy threshold. In certain embodiments, portions of the brain irradiated by irradiating the treatment sites at the scalp do not overlap one another. In certain such embodiments, the treatment sites at the scalp are positioned so as to irradiate as much of the cortex as possible.

Example Wearable Apparatus

Figure 22:
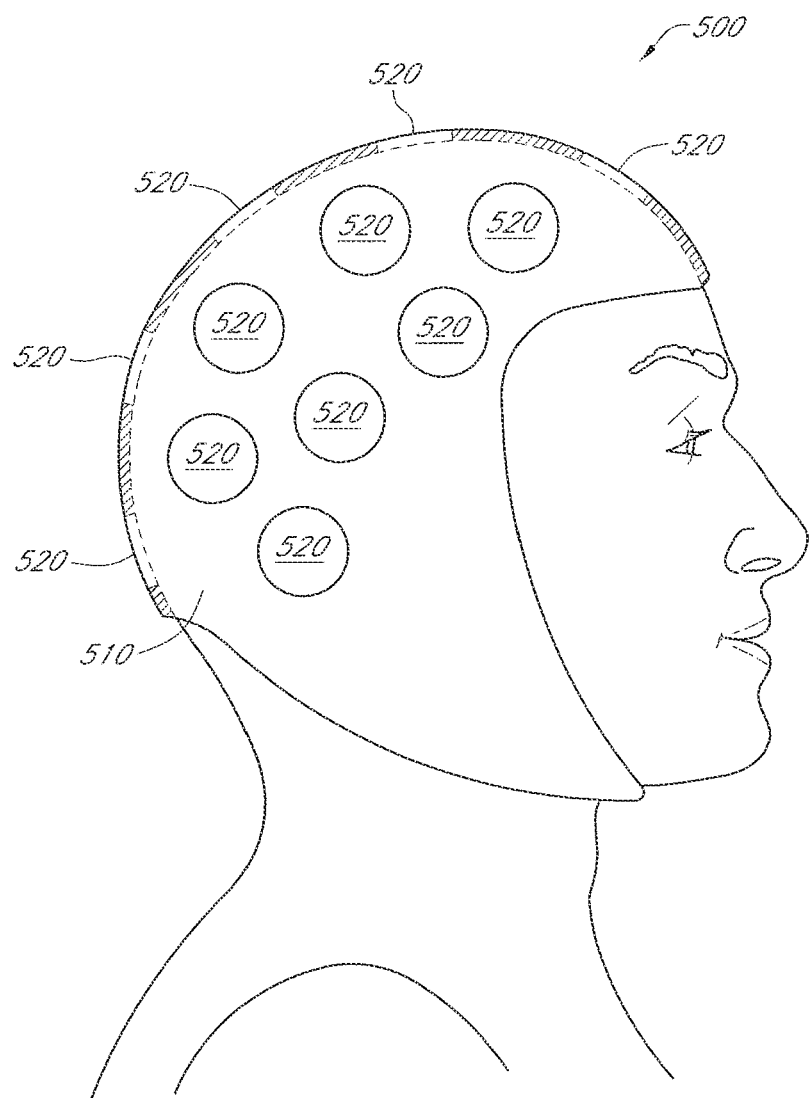
FIG. 22 schematically illustrates an example apparatus which is wearable by a patient for treating the patient's brain.

FIG. 22 schematically illustrates an example apparatus 500 which is wearable by a patient for treating the patient's brain. The apparatus 500 comprises a body 510 and a plurality of indicators 520. The body 510 is adapted to be worn over at least a portion of the patient's scalp when the apparatus 500 is worn by the patient. The plurality of indicators 520 correspond to a plurality of treatment site location at the patient's scalp where light is to be applied to irradiate at least a portion of the patient's brain. At least one indicator 520 comprises a portion of the body which is substantially transmissive (e.g., substantially transparent or substantially translucent) to light emitted from the emission surface 22 to irradiate at least a portion of the patient's brain.

In certain embodiments, at least one of the indicators 520 denotes a position within an area of the patient's scalp corresponding to a treatment site location. In certain such embodiments, the position is the center of the area of the patient's scalp. The adjacent treatment sites of certain embodiments have areas which do not overlap one another or have perimeters which are spaced from one another. In certain such embodiments, the perimeters are spaced from one another by at least 10 millimeters or at least 25 millimeters.

In certain embodiments, each indicator 520 comprises an opening or aperture through the body 510 at which the beam delivery apparatus 10 can be placed to irradiate the portion of the patient's scalp exposed by the hole or aperture. In certain embodiments, the aperture has a substantially circular perimeter and a diameter in a range between 20 millimeters and 50 millimeters or in a range between 25 millimeters and 35 millimeters. In certain embodiments, the aperture has a substantially elliptical perimeter with a minor axis greater than 20 millimeters and a major axis less than 50 millimeters. Other shapes of the aperture are also compatible with certain embodiments described herein.

In certain embodiments, the plurality of indicators 520 comprises at least about 10 indicators 520 distributed across the patient's scalp, while in certain other embodiments, the plurality of indicators 520 comprises 20 indicators 520. In certain other embodiments, the plurality of indicators 520 comprises between 15 and 25 indicators 520. In certain embodiments, the optically transmissive portion of each indicator 520 has an area of at least 1 cm$^2$, in a range between 1 cm$^2$ and 20 cm$^2$, or in a range between 5 cm$^2$ and 10 cm$^2$.

In certain embodiments, the body 510 comprises a hood, while in other embodiments, the body 510 comprises a cap or has another configuration which is wearable on the patient's head and serves as a support for orienting the indicators 520 on the patient's head. In certain embodiments, the body 510 comprises a stretchable or pliant material which generally conforms to the patient's scalp. In certain embodiments, the body 510 comprises nylon-backed polychloroprene or Tyvek®. In certain embodiments, the body 510 is available in different sizes (e.g., small, medium, large) to accommodate different sizes of heads. In certain embodiments, the body 510 is disposable after a single use to advantageously avoid spreading infection or disease between subsequent patients.

The indicators 520 of certain embodiments are configured to guide an operator to irradiate the patient's scalp at the corresponding treatment site locations sequentially one at a time in a predetermined order. In certain embodiments, the wearable apparatus 500 further comprises a plurality of labels 522 with each label in proximity to a corresponding indicator. The labels 522 advantageously provide one or more numbers, letters, or symbols (e.g., bar codes) to each of the indicators 520 to distinguish the various indicators 520 from one another. In certain such embodiments, the labels 522 are mechanically coupled to the corresponding indicators so as to be visible to users of the beam delivery apparatus 10.

Figure 23A:
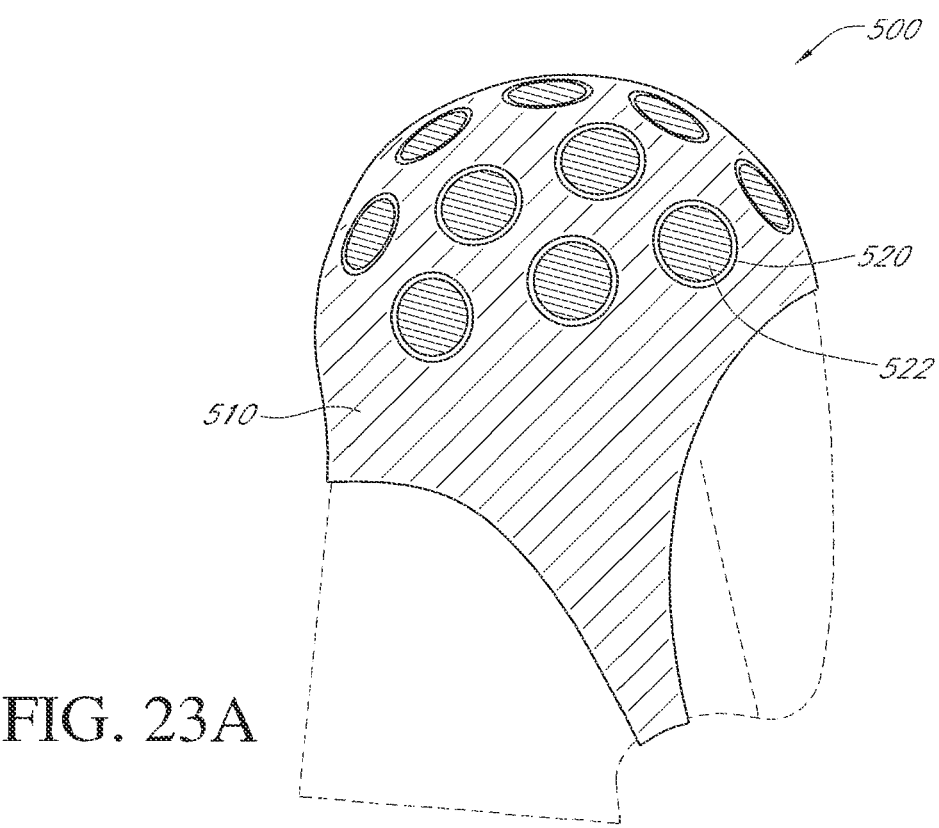
FIGS. 23A and 23B schematically illustrate the left-side and right-side of an example apparatus, respectively, with labels substantially covering the indicators corresponding to the treatment sites.
Figure 23B:
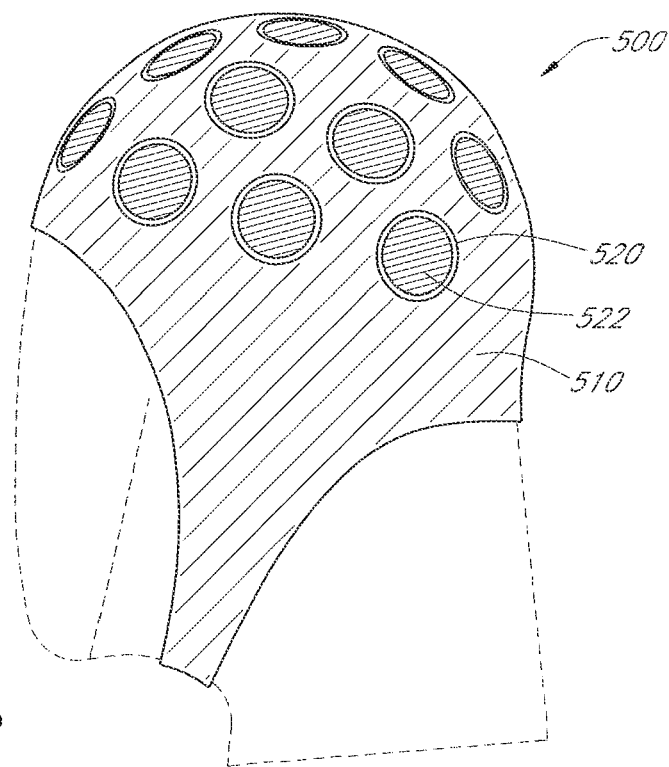

FIGS. 23A and 23B schematically illustrate the left-side and right-side of an example apparatus 500, respectively, with labels 522 substantially covering the indicators 520 corresponding to the treatment sites. In certain embodiments, the labels 522 are advantageously used to keep track of which treatment sites have been irradiated and which treatment sites are yet to be irradiated. In certain such embodiments, at least a portion of each label 522 comprises a portion of the body (e.g., a pull-off tab or flap) which is configured to be removed from the apparatus 500 when the treatment site corresponding to the indicator 520 has been irradiated. In certain embodiments, the labels 522 comprise removable portions of the body 510 which cover the corresponding indicator 520. In certain such embodiments, prior to irradiating the treatment site location corresponding to the indicator 520, the corresponding label 522 can be removed to allow access to the underlying portion of the patient's scalp.

In certain embodiments, the label 522 has a code sequence which the operator enters into the controller prior to irradiation so as to inform the controller of which treatment site is next to be irradiated. In certain other embodiments, each label 522 comprises a bar code or a radio-frequency identification device (RFID) which is readable by a sensor electrically coupled to the controller. The controller of such embodiments keeps track of which treatment sites have been irradiated, and in certain such embodiments, the controller only actuates the light source when the beam delivery apparatus 10 is in optical and thermal communication with the proper treatment site of the patient's scalp.

Figure 23C:
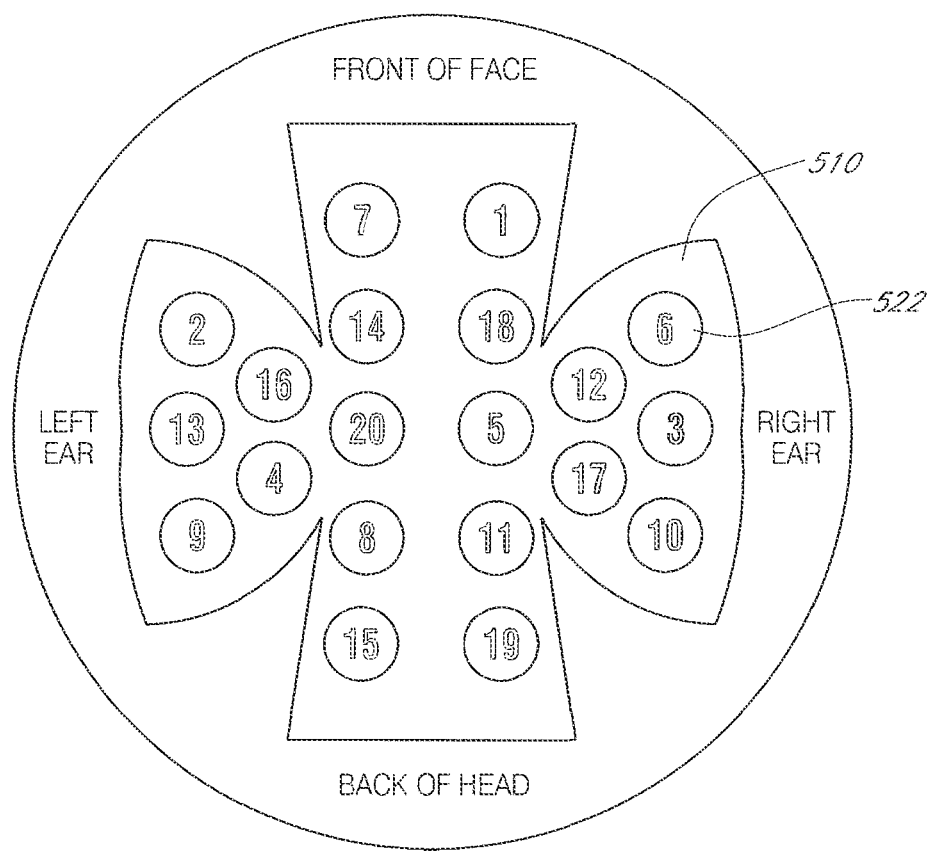
FIG. 23C schematically illustrates an example labeling configuration from above a flattened view of the apparatus 500 of FIGS. 23A and 23B.

FIG. 23C schematically illustrates an example labeling configuration from above a flattened view of the apparatus 500 of FIGS. 23A and 23B. The labeling convention of FIG. 23C is compatible with irradiation of both halves or hemispheres of the patient's brain. Other labeling conventions are also compatible with embodiments described herein.

In certain embodiments, the labels 522 are advantageously used to guide an operator to irradiate the patient's brain at the various treatment sites sequentially at each of the treatment sites one at a time through the indicators 520 in a predetermined order by optically and thermally coupling the beam delivery apparatus 10 to sequential treatment sites corresponding to the indicators 520. For example, for the labeling configuration of FIG. 23C, the operator can first irradiate treatment site "1," followed by treatment sites "2," "3," "4," etc. to sequentially irradiate each of the twenty treatment sites one at a time. In certain such embodiments, the predetermined order of the treatment sites is selected to advantageously reduce temperature increases which would result from sequentially irradiating treatment sites in proximity to one another.

In certain embodiments, the predetermined order comprises irradiation of a first treatment site location on a first side of the patient's scalp (e.g., site "2" of FIG. 23C), then irradiation of a second treatment site location on a second side of the patient's scalp (e.g., site "3" of FIG. 23C), then irradiation of a third treatment site location on the first side of the patient's scalp (e.g., site "4" of FIG. 23C). In certain such embodiments, the predetermined order further comprises irradiation of a fourth treatment site location on the second side of the patient's scalp after irradiation of the third treatment site location. In certain embodiments, two sequentially irradiated treatment site locations are separated from one another by at least 25 millimeters.

In certain embodiments, the apparatus 500 serves as a template for marking the patient's scalp to indicate the treatment site locations. The apertures of the apparatus 500 can be used to guide a user place marks on the patient's scalp, and the apparatus 500 can then be removed from the patient's scalp before the beam delivery apparatus 10 is applied to the scalp for irradiating the patient's brain. The marks remain on the patient's scalp to guide the operator while the patient's brain is irradiated.

Methods of Light Delivery

FIGS. 24-27 are flow diagrams of example methods for irradiating a surface with light. As described more fully below, the methods are described by referring to the beam delivery apparatus 10 and components thereof, as described herein. Other configurations of a beam delivery apparatus are also compatible with the methods in accordance with embodiments described herein.

Figure 24:
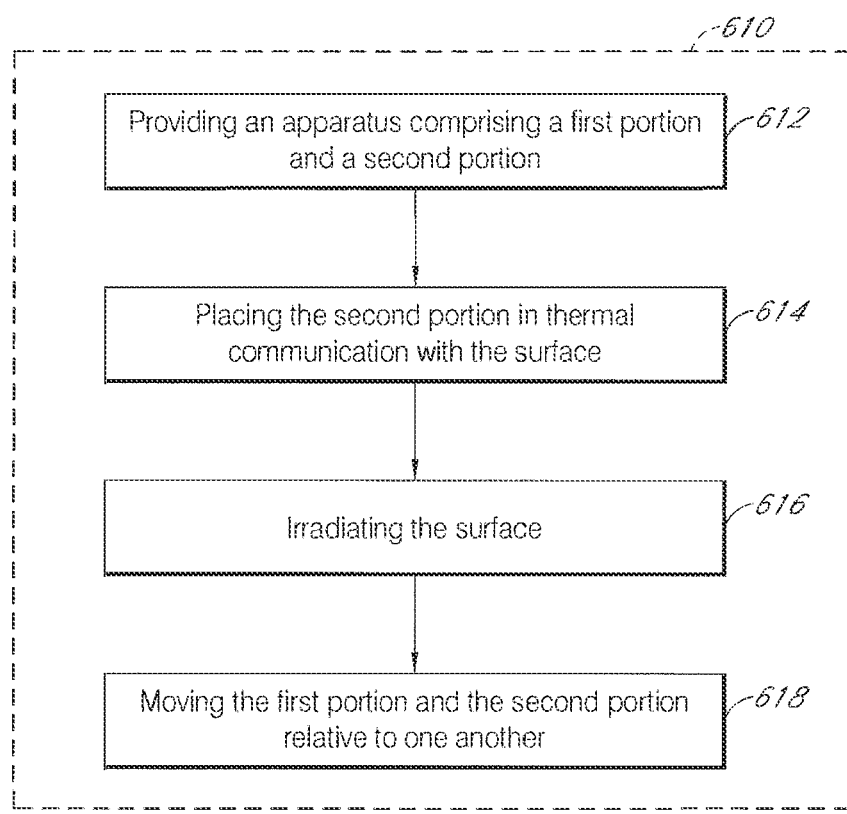
FIGS. 24-27 are flow diagrams of example methods for irradiating a surface with light.

The method 610 of FIG. 24 comprises providing a beam delivery apparatus 10 in an operational block 612. The beam delivery apparatus 10 comprises a first portion and a second portion mechanically coupled to the first portion and in optical communication with the first portion, wherein the first portion and the second portion are configured to move relative to one another, as described more fully above. The method 610 further comprises placing the second portion in thermal communication with the surface in an operational block 614 (e.g., releasably operatively coupling the second portion to the surface). The method 610 further comprises irradiating the surface such that the light from the first portion propagates through the second portion in an operational block 616. The method 610 further comprises moving the first portion and the second portion relative to one another in response to the second portion being placed in thermal communication with the surface in an operational block 618.

Figure 25:
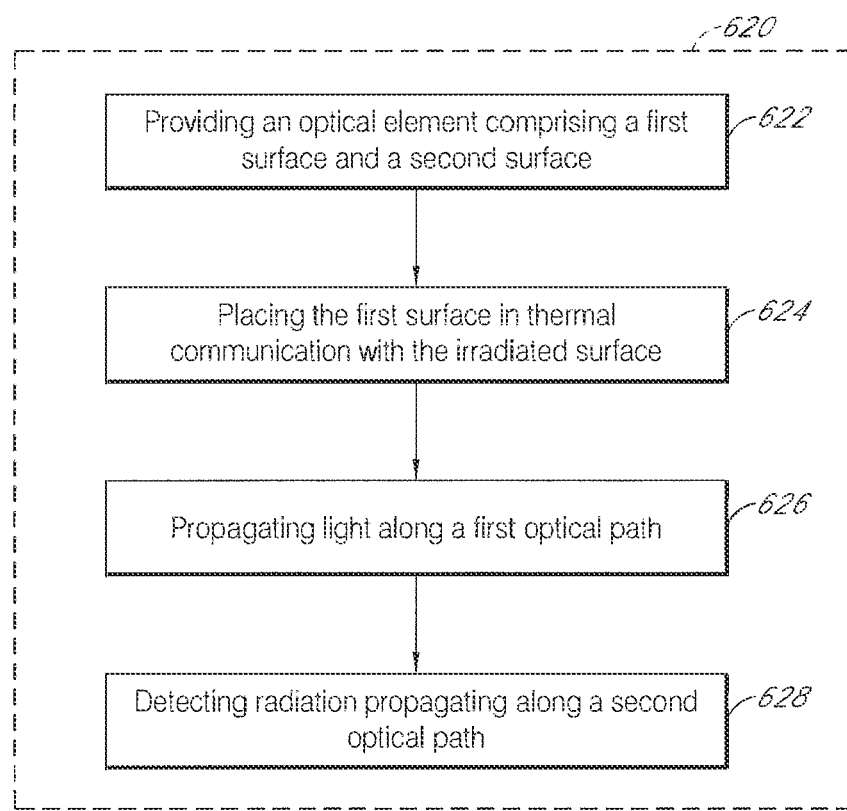

The method 620 of FIG. 25 comprises providing an optical element 23 in an operational block 622. The optical element 23 comprises a substantially optically transmissive and substantially thermally conductive material, and the optical element 23 has a first surface 22 and a second surface 24, as described more fully above. The method 620 further comprises placing the first surface 22 in thermal communication with the irradiated surface in an operational block 624 (e.g., releasably operatively coupling the first surface 22 to the irradiated surface). The method 620 further comprises propagating the light along a first optical path 32 through the second surface 24 and through the first surface 22 to the irradiated surface in an operational block 626. The method 620 further comprises detecting radiation propagating along a second optical path 82 from at least a portion of the second surface 24, wherein the first optical path 32 and the second optical path 82 have a non-zero angle therebetween in an operational block 628. In certain embodiments, the first surface 22 and the second surface 24 face in generally opposite directions, and the first surface 22 is not along the second optical path 82.

Figure 26:
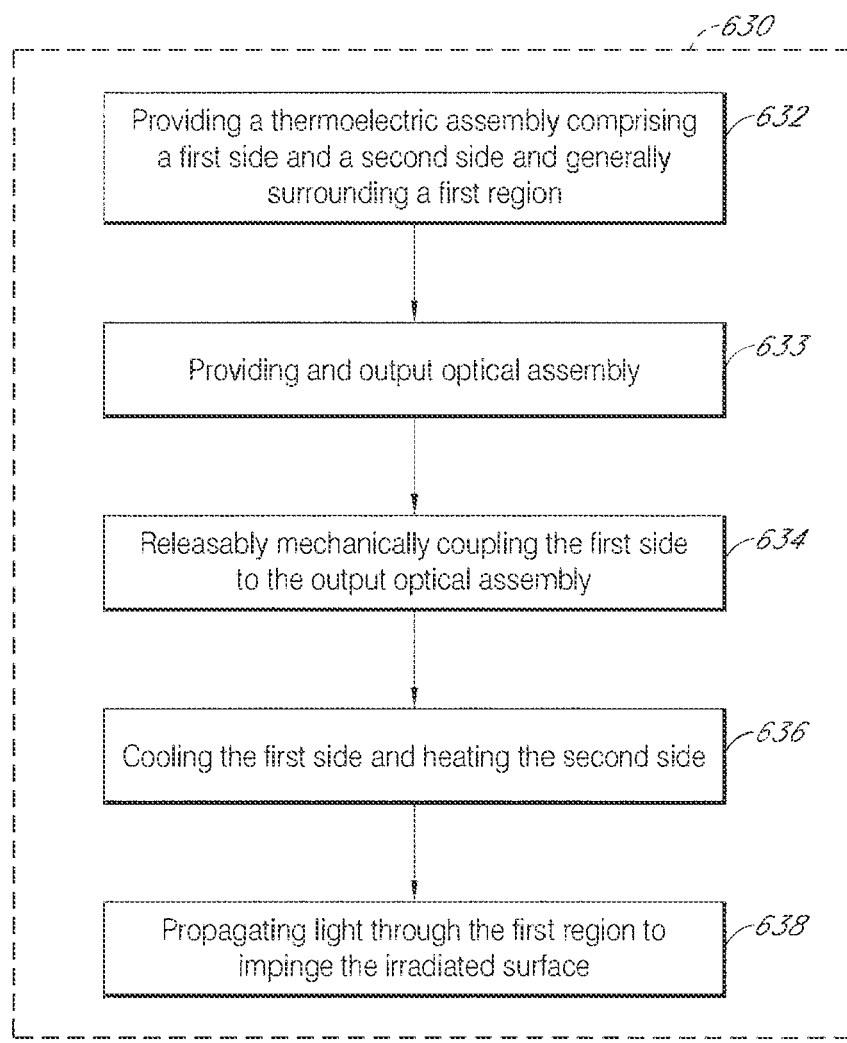

The method 630 of FIG. 26 comprises providing a thermoelectric assembly 90 in an operational block 632. The thermoelectric assembly 90 comprises a first surface 93 and a second surface 94, and the thermoelectric assembly 90 generally surrounds a first region 97, as described more fully above. The method 630 further comprises providing an output optical assembly 20 in an operational block 633. The method 630 further comprises releasably mechanically coupling the first surface 93 of the thermoelectric assembly 90 to the output optical assembly 20 so that the first surface 93 is in thermal communication with the output optical assembly 20 in an operational block 634. The method 630 further comprises cooling the first surface 93 and heating the second surface 94 in an operational block 636. The method 630 further comprises propagating light through the first region 97 to impinge the irradiated surface in an operational block 638. In certain embodiments, the first surface 22 and the second surface 24 face in generally opposite directions, and the first surface 22 is not along the second optical path 82.

In certain embodiments, the output optical assembly 20 comprises an optical element 23 and a thermally conductive portion generally surrounding a second region 28. The thermally conductive portion is in thermal communication with the optical element 23. In certain such embodiments, releasably mechanically coupling the first surface 93 to the output optical assembly 20 comprises releasably mechanically coupling the first surface 93 to the thermally conductive portion. In certain such embodiments, the method 630 further comprises placing the optical element 23 in thermal communication with the irradiated surface and propagating the light comprises transmitting the light through the first region 97, the second region 28, and the optical element 23 to impinge the irradiated surface. In certain embodiments, the method 630 further comprises providing a heat sink 100 in thermal communication with the second surface 94 of the thermoelectric assembly 90. The heat sink 100 generally surrounds a third region 107, and propagating the light comprises transmitting the light through the third region 107, the first region 97, the second region 28, and the optical element 23.

Figure 27:
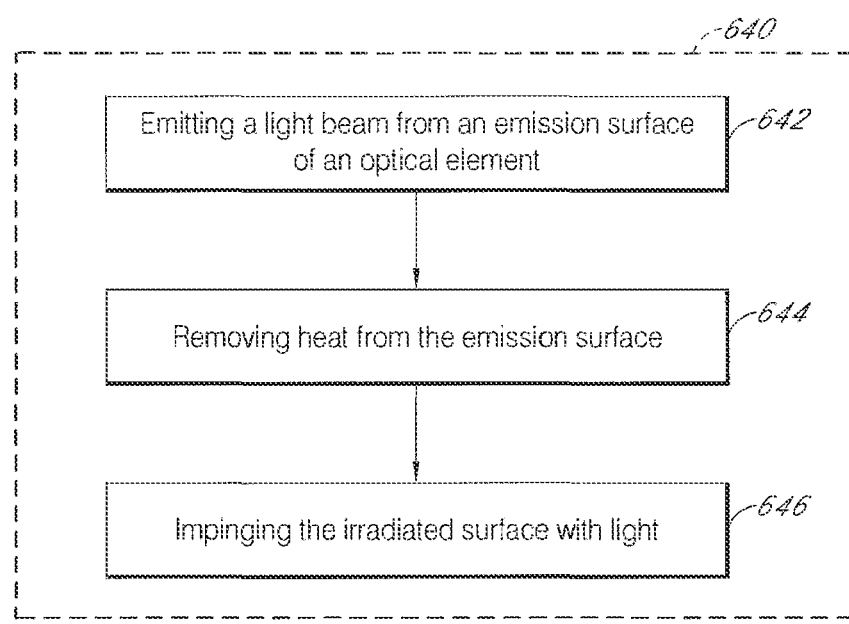

The method 640 of FIG. 27 comprises emitting a light beam from an emission surface 22 of an optical element 23 in an operational block 642. The light beam at the emission surface 22 has one or more wavelengths in a range of about 630 nanometers to about 1064 nanometers, a cross-sectional area greater than about 2 cm$^2$, and a time-averaged irradiance in a range of about 10 mW/cm$^2$ to about 10 W/cm$^2$ across the cross-sectional area, as described more fully above. The method 640 further comprises removing heat from the emission surface 22 at a rate in a range of about 0.1 Watt to about 5 Watts in an operational block 644. The method 640 further comprises impinging the irradiated surface with the light beam in an operational block 646.

The method 640 of certain embodiments further comprises placing the emission surface 22 in thermal communication with the irradiated surface (e.g., using the emission surface 22 to apply pressure to the irradiated surface by applying a force to the emission surface 22 in a direction generally towards the irradiated surface, the pressure greater than about 0.1 pound per square inch or about equal to 2 pounds per square inch).

In certain embodiments, impinging the irradiated surface with the light beam is performed for a time period of 10 seconds to two hours, for a time period of 60 seconds to 600 seconds, or for a time period of about 120 seconds. In certain embodiments, the steps of the operational blocks 642, 644, and 646 are performed concurrently. The method 640 of certain embodiments further comprises moving the emission surface 22 from a first position at which a first portion of the irradiated surface is impinged by the light beam to a second position, and repeating the steps of the operational blocks 642, 644, and 646 so as to impinge a second portion of the irradiated surface by light emitted from the emission surface 22. The first portion and the second portion do not overlap one another in certain embodiments. This method can be repeated so as to impinge twenty portions of the irradiated surface by light emitted from the emission surface 22. In certain such embodiments, the twenty portions of the irradiated surface do not overlap one another. However, the portions of the patient's brain irradiated by impinging these twenty portions of the patient's scalp do overlap one another in certain embodiments.

The irradiated surface of certain embodiments of the methods described above in reference to FIGS. 24-27 comprises a portion of the patient's scalp. In certain other embodiments, the surface irradiated by the light comprises a portion of a light-detection system configured to measure one or more parameters of light irradiating the surface (e.g., irradiance, total power, beam size, beam profile, beam uniformity). In certain such embodiments, the method further comprises measuring the one or more parameters of the light from the apparatus 10 impinging the surface. For example, the light-detection system can comprise a portion of the apparatus 10 configured to test the light beam emitted from the emission surface 22 immediately prior to treatment of the patient. In this way, the light-detection system can be used to ensure that the light beam applied to the patient's scalp has the desired treatment parameters.

In certain embodiments, a patient is treated by identifying a plurality of treatment sites (e.g., at least about 10) on the patient's scalp, directing a light beam to each of the treatment sites, and irradiating each treatment site with the light beam. As described more fully below, in certain embodiments, the treatment sites are identified using an apparatus comprising a plurality of indicators, each of which corresponds to a treatment site location. In certain such embodiments, the treatment sites are sequentially irradiated by a light beam from the emission surface. In certain other embodiments, the treatment sites are instead identified by other indicia. For example, each of the treatment sites can be identified by markings made on the scalp, or by structures placed in proximity to the scalp. Each of the treatment sites can then be irradiated. In certain embodiments, each of the treatment sites is irradiated by a light beam from the emission surface while the emission surface is in contact with the scalp or in contact with an intervening optically transmissive element which contacts the scalp. In certain other embodiments, the scalp is not contacted by either the emission surface or an intervening element. In certain embodiments, each of the treatment sites is irradiated using a single beam delivery apparatus which is sequentially moved from one treatment site to another. In certain other embodiments, a plurality of beam delivery apparatuses are used to irradiate multiple treatment sites concurrently. In certain such embodiments, the number of beam delivery apparatuses is fewer than the number of treatments sites, and the plurality of beam delivery apparatuses are sequentially moved to sequentially irradiate the treatment sites.

Figure 28:
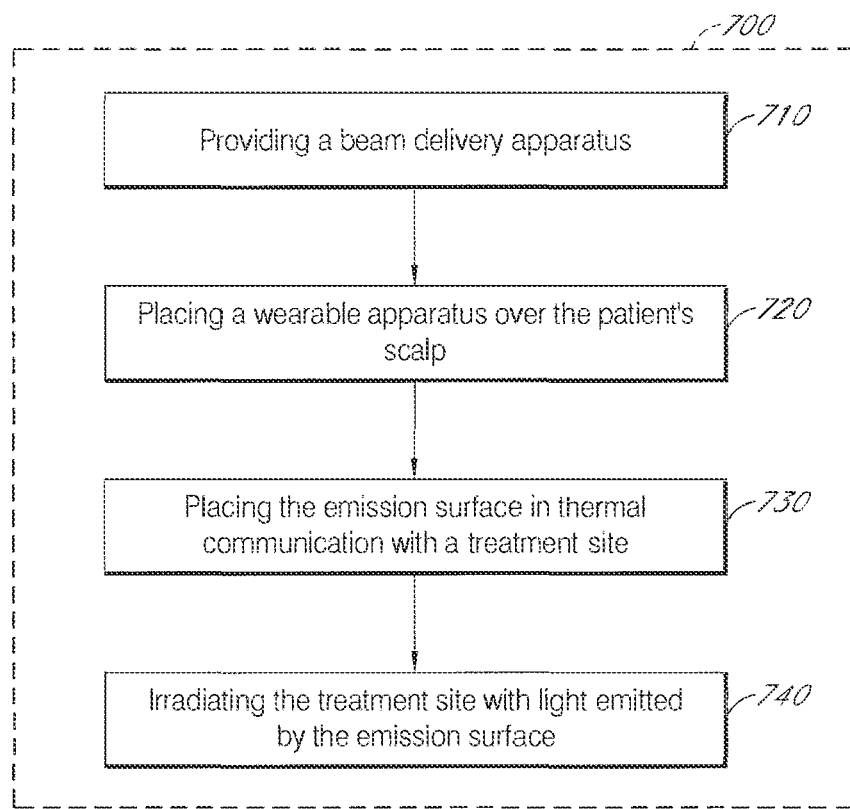
FIG. 28 is a flow diagram of an example method for controllably exposing at least one predetermined area of a patient's scalp to laser light to irradiate the patient's brain.

FIG. 28 is a flow diagram of an example method 700 for controllably exposing at least one predetermined area of a patient's scalp to laser light to irradiate the patient's brain. As described more fully below, the method 700 is described by referring to the wearable apparatus 500 and the beam delivery apparatus 10 described herein. Other configurations of a wearable apparatus 500 and a beam delivery apparatus 10 are also compatible with the method 700 in accordance with embodiments described herein.

The method 700 comprises providing a beam delivery apparatus 10 in an operational block 710. In certain embodiments, the beam delivery apparatus 10 comprises an emission surface 22 configured to emit a light beam. Other configurations of the beam delivery apparatus 10 besides those described above are also compatible with certain embodiments described herein.

The method 700 further comprises placing a wearable apparatus 500 over the patient's scalp in an operational block 720. The apparatus 500 comprises a body 510 and a plurality of indicators 520. In certain embodiments, each indicator 520 is substantially transmissive to the light beam emitted from the emission surface 22. Other configurations of the wearable apparatus 500 besides those described above are also compatible with certain embodiments described herein.

The method 700 further comprises placing the emission surface 22 in thermal communication with a treatment site of the patient's scalp to be irradiated in an operational block 730. The method 700 further comprises irradiating the treatment site with light emitted by the emission surface 22 in an operational block 740. In certain embodiments, the light beam is transmitted through the indicator 520.

In certain embodiments, providing the light emitting apparatus 600 in the operational block 710 comprises preparing the beam delivery apparatus 10 for use to treat the patient. In certain embodiments, preparing the beam delivery apparatus 10 comprises cleaning the portion of the beam delivery apparatus 10 through which laser light is outputted. In certain embodiments, preparing the beam delivery apparatus 10 comprises verifying a power calibration of laser light outputted from the beam delivery apparatus 10. Such verification can comprise measuring the light intensity output from the beam delivery apparatus 10 and comparing the measured intensity to an expected intensity level.

In certain embodiments, placing the wearable apparatus 500 over the patient's scalp in the operational block 720 comprises preparing the patient's scalp for treatment. For example, in certain embodiments, preparing the patient's scalp for treatment comprises removing hair from the predetermined areas of the patient's scalp to be irradiated. Removing the hair (e.g., by shaving) advantageously reduces heating of the patient's scalp by hair which absorbs laser light from the beam delivery apparatus 10. In certain embodiments, placing the wearable apparatus 500 over the patient's scalp in the operational block 720 comprises positioning the wearable apparatus 500 so that each indicator 520 is in position to indicate a corresponding portion of the patient's scalp to be irradiated.

In certain embodiments, placing the emission surface 22 in thermal communication with the treatment site in the operational block 730 comprises pressing the emission surface 22 to the treatment site. In certain embodiments, by pressing the emission surface 22 against the treatment site in this way, pressure is applied to the portion of the patient's scalp of the treatment site so as to advantageously blanch the portion of the patient's scalp to be irradiated.

In certain embodiments, irradiating the treatment site of the patient's scalp in the operational block 740 comprises triggering the emission of light from the emission surface 22 by pressing the emission surface 22 against the treatment site with a predetermined level of pressure. In certain embodiments, the emission of light from the emission surface 22 continues only if a predetermined level of pressure is maintained by pressing the emission surface 22 against the treatment site. In certain embodiments, light is emitted from the emission surface 22 to the treatment site for a predetermined period of time.

In certain embodiments, the method further comprises irradiating additional treatment sites of the patient's scalp during a treatment process. For example, after irradiating a first treatment site corresponding to a first indicator, as described above, the emission surface 22 can be placed in contact with a second indicator corresponding to a second treatment site and irradiating the second treatment site with light emitted by the emission surface 22. The various treatment sites of the patient's scalp can be irradiated sequentially to one another in a predetermined sequence. In certain embodiments, the predetermined sequence is represented by the indicators of the wearable apparatus 500. In certain such embodiments, the beam delivery apparatus 10 comprises an interlock system which interfaces with the indicators of the wearable apparatus 500 to prevent the various treatment sites from being irradiated out of the predetermined sequence.

Figure 29:
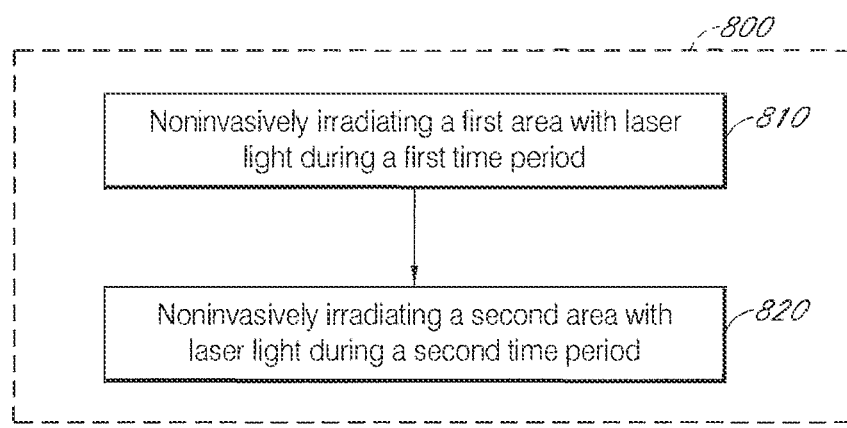
FIG. 29 is a flow diagram of another example method for treating a patient's brain.

FIG. 29 is a flow diagram of another example method 800 for treating a patient's brain. The method 800 is described below by referring to the wearable apparatus 500 and the beam delivery apparatus 10 described herein. Other configurations of a wearable apparatus 500 and a beam delivery apparatus 10 are also compatible with the method 700 in accordance with embodiments described herein.

The method 800 comprises noninvasively irradiating a first area of at least 1 cm$^2$ of the patient's scalp with laser light during a first time period in an operational block 810. The method 800 further comprises noninvasively irradiating a second area of at least 1 cm$^2$ of the patient's scalp with laser light during a second time period in an operational block 820. The first area and the second area do not overlap one another, and the first time period and the second time period do not overlap one another. In certain embodiments, the first area and the second area are spaced from one another by at least 10 millimeters. In certain embodiments, the first area is over a first hemisphere of the brain, and the second area is over a second hemisphere of the brain.

In certain embodiments, the method 800 further comprises identifying the first area and the second area by placing a template over the patient's scalp. The template comprises a first indicator of the first area and a second indicator of the second area. For example, the first indicator can comprise a first opening in the template and the second indicator can comprise a second opening in the template. In certain embodiments, the method 800 further comprises placing a laser light source at a first position to noninvasively irradiate the first area and moving the laser light source to a second position to noninvasively irradiate the second area.

In certain embodiments, the method 800 further comprises increasing the transmissivity of the first area to the laser light and increasing the transmissivity of the second area to the laser light. Increasing the transmissivity of the first area can comprise applying pressure to the first area to at least partially blanch the first area, removing hair from the first area prior to noninvasively irradiating the first area, applying an index-matching material to the first area, or a combination of two or more of these measures. Increasing the transmissivity of the second area can comprise applying pressure to the second area to at least partially blanch the second area, removing hair from the second area prior to noninvasively irradiating the second area, applying an index-matching material to the second area, or a combination of two or more of these measures.

Neurologic Function Scales

Neurologic function scales can be used to quantify or otherwise characterize the efficacy of various embodiments described herein. Neurologic function scales generally use a number of levels or points, each point corresponding to an aspect of the patient's condition. The number of points for a patient can be used to quantify the patient's condition, and improvements in the patient's condition can be expressed by changes of the number of points. One example neurologic function scale is the National Institute of Health Stroke Scale (NIHSS) which can be used for short-term measurements of efficacy (e.g., at 24 hours). The NIHSS is a comprehensive and objective scale which utilizes a seven-minute physical exam, a 13 item scale, and 42 points. Zero points corresponds to a normal exam, 42 points (the maximum) corresponds to basically comatose, and over 15-20 points indicates that the effects of the stroke are particularly severe. The NIHSS has previously been used for tPA trials in the treatment of ischemic stroke, with a 4-point change over 24 hours and an overall score of 0 or 1 at three months indicative of a favorable outcome. Other neurologic function scales include, but are not limited to, modified Rankin Scale (mRS), Barthel Index (BI), Glasgow Outcome, Glasgow Coma Scale, Canadian Neurologic Scale, and stroke impact scales such as SIS-3 and SIS-16. In some scales, an improvement in the patient's condition is indicated by a reduction in the number of points. For example, the mRS has six points total, with zero corresponding to normal functioning, and six corresponding to death. In other scales, an improvement in the patient's condition is indicated by an increase in the number of points. For example, in the Glasgow Outcome which has five points, zero corresponds to death and five corresponds to full recovery. In certain embodiments, two or more of the neurologic function scales can be used in combination with one another, and can provide longer-term measurements of efficacy (e.g., at three months).

For stroke, the U.S. Food and Drug Administration (FDA) and the neurologic community have expressed interest in clinical patient outcomes at 90 days post stroke. Two of the most common and accepted instruments for measuring efficacy are the NIHSS and mRS. The FDA is flexible in the way that neurologic function scales can be used. For example, it is acceptable to use the mRS (i) in dichotomized fashion with success at score of 0-1 or (ii) it can be analyzed looking at shifts in the scale showing improvement of patients along the five-point scale.

In certain embodiments described herein, a patient exhibiting symptoms of an ischemic stroke is treated by irradiating a plurality of treatment sites on the patient's scalp. The irradiation is performed utilizing irradiation parameters (e.g., wavelength, irradiance, time period of irradiation, etc.) which, when applied to members of a treated group of patients, produce at least a 2% average difference between the treated group and a placebo group on at least one neurologic function scale analyzed in dichotomized or any other fashion and selected from the group consisting of: NIHSS, mRS, BI, Glasgow Outcome, Glasgow Coma Scale, Canadian Neurologic Scale, SIS-3, and SIS-16. Certain other embodiments produce at least a 4% average difference, at least a 6% average difference, or at least a 10% average difference between treated and placebo groups on at least one of the neurologic function scales analyzed in dichotomized or any other fashion and selected from the group consisting of: NIHSS, mRS, BI, Glasgow Outcome, Glasgow Coma Scale, Canadian Neurologic Scale, SIS-3, and SIS-16. In certain embodiments, the irradiation of the patient's scalp produces a change in the patient's condition. In certain such embodiments, the change in the patient's condition corresponds to a change in the number of points indicative of the patient's condition. In certain such embodiments, the irradiation produces a change of one point, a change of two points, a change of three points, or a change of more than three points on a neurologic function scale.

Transmission in Human Brain

Power density (PD) measurements have been made to determine the transmission of laser light having a wavelength of approximately 808 nanometers through successive layers of human brain tissue. Laser light having a wavelength of (808±5) nanometers with a maximum output of approximately 35 Watts was applied to the surface of the cortex using a beam delivery system which approximated the beam profile after the laser light passes through the human skull. Peak power density measurements were taken through sections of human brain tissue using an Ocean Optics spectrophotometer Model USB 2000, Serial No. G1965 and beam diameter after scattering was approximated using a Sony Model DCR-IP220, Serial No. 132289.

A fresh human brain and spinal cord specimen (obtained within six hours after death) was collected and placed in physiologic Dakins solution. The pia layer, arachnoid layer, and vasculature were intact. The brain was sectioned in the midline sagittaly and the section was placed in a container and measurements taken at thicknesses of 4.0 centimeters (f 0.5 centimeter), 2.5 centimeters (f 0.3 centimeter), and 1.5 centimeters (±0.2 centimeter). The PD measurements are shown in Table 1:

TABLE 1

| Thickness | PD at cortex | Average PD at thickness |
|---|---|---|
| 4.0 cm | 20 mW/cm$^2$ | 4.9 μW/cm$^2$ |
| 2.5 cm | 20 mW/cm$^2$ | 20 μW/cm$^2$ |
| 1.5 cm | 10 mW/cm$^2$ | 148 μW/cm$^2$ |

Figure 30:
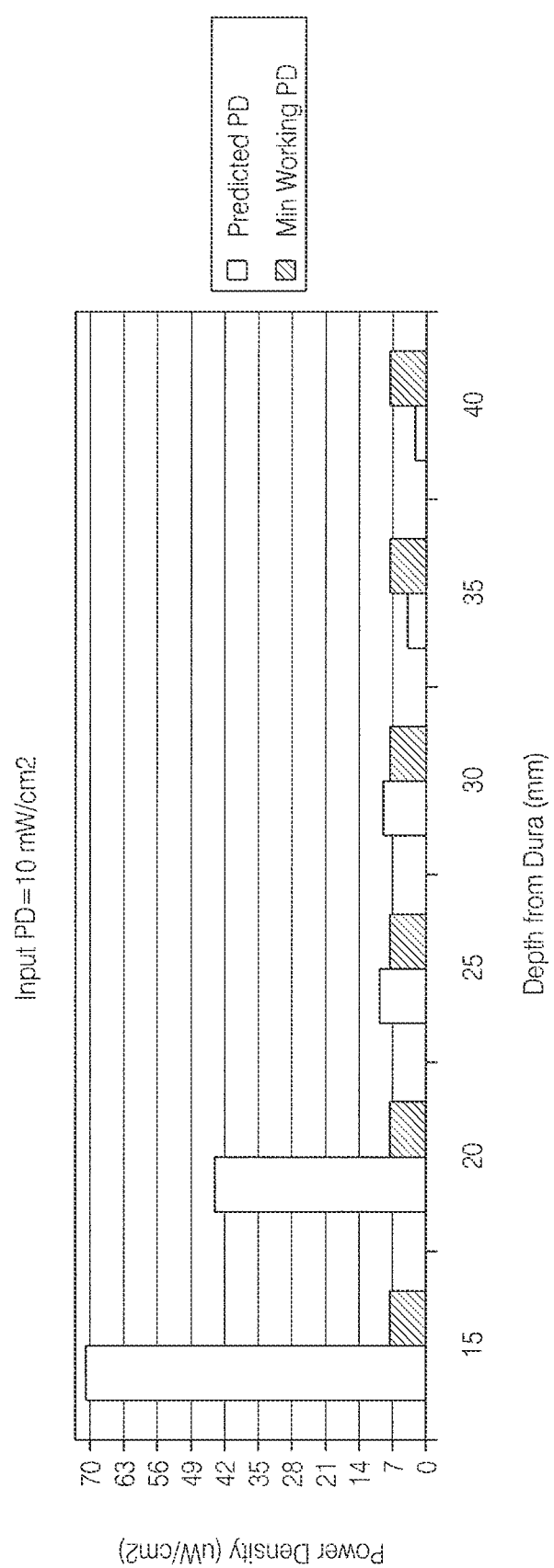
FIG. 30 is a graph of the power density versus the depth from the dura for an input power density of 10 mW/cm$^2$ with the light bars corresponding to predicted values of the power density and dark bars corresponding to an estimated minimum working PD of is 7.5 µW/cm$^2$, as described below.

FIG. 30 is a graph of the PD versus the depth from the dura for an input PD of 10 mW/cm$^2$ with the light bars corresponding to predicted values of the PD and dark bars corresponding to an estimated minimum working PD of is 7.5 μW/cm$^2$, as described below.

Based upon prior animal experimentation, a conservative estimation of the minimum known PD within the tissue of the brain which is able to show efficacy in stroke animal models is 7.5 μW/cm$^2$. This estimated minimum working PD is drawn from an experiment in which 10 mW was applied to the rat brain surface, and 7.5 μW/cm$^2$ PD was directly measured 1.8 centimeters from the surface. This stroke model consistently produced significant efficacy, including for strokes 1.8 centimeters from the laser probe. Note that this 7.5 μW/cm$^2$ is a conservative estimate; the same irradiance or power density at the brain surface also consistently produces significant efficacy in a 3-centimeter rabbit clot shower model. Note also that the power density measurements in the human brain experiment do not factor in the effect from the CNS-filled sulci, through which the laser energy should be readily transmitted. However, even conservatively assuming 7.5 µW/cm² as the minimum power density hurdle and ignoring expected transmission benefits from the sulci, the experiment described above confirms that approximately 10-15 mW/cm² transmitted upon the cortex (as per an example dosimetry in man) will be effective to at least 3.0 centimeters from the surface of the brain.

In Vivo Thermal Measurements

In vivo thermal measurements were made to determine the heating effect in living tissue of laser light having a wavelength of approximately 808 nanometers. A GaAlAs laser source of 808-nanometer light was placed in direct contact with the skin of the heads of live rabbits and rats. The laser source had an approximately Gaussian beam profile with a beam diameter of 2.54.0 millimeters (1/e²). Thermocouple probes (Model Bat-12 from Physitemp Instruments Inc. of Clifton, New Jersey) were placed in the subcutaneous tissue and below the dura and measurements were recorded at various irradiances or power densities. The results of these measurements are shown in Table 2:

TABLE 2

| Animal | Probe location | Dose | Exposure time | Temperature increase |
|---|---|---|---|---|
| Rat | Subcutaneous | 15 µW/cm² | 4 minutes | approximately 3° C. |
| Rat | Subdural | 15 µW/cm² | 4 minutes | approximately 1° C. |
| Rat | Subcutaneous | 75 µW/cm² | 4 minutes | approximately 7° C. |
| Rat | Subdural | 75 µW/cm² | 4 minutes | approximately 7° C. |
| Rabbit | Subcutaneous | 7.5 µW/cm² | 5 minutes | less than 0.5° C. |
| Rabbit | Subdural | 7.5 µW/cm² | 5 minutes | less than 0.5° C. |
| Rabbit | Subcutaneous | 37.5 µW/cm² | 5 minutes | approximately 5.5° C. |
| Rabbit | Subdural | 37.5 µW/cm² | 5 minutes | less than 0.5° C. |

There is minimal heating (e.g., less than 0.5° C.) in the subdural region at four times the therapeutic energy density. The "heat sink" effect of living tissue that minimizes possible heating in the cortex is significantly larger in humans than in rats or rabbits, due to the larger heat sink and blood flow volume, which further limits the undesirable effects of heating in the region of stroke. Therefore, in certain embodiments described herein, a therapeutic dosage of energy is delivered to the area of a stroke without undesirable heating of the dura.

Phototherapy Example 1

One example of phototherapy (Lampl Y, Zivin J A, Fisher M, Lew R. Welin L, Dahlof B, Borenstein P, Andersson B, Perez 1, Caparo C, Ilic S, Oron U. Infrared laser therapy for ischemic stroke: a new treatment strategy: Results of the NeuroThera Effectiveness and Safety Trial-1 (NEST-1). Stroke. 2007; 38:1843-1849, incorporated in its entirety by reference herein, suggested the safety and efficacy of transcranial light therapy (TLT) for treatment of humans 40 to 85 years of age with ischemic stroke within 24 hours of stroke onset in a small randomized, controlled trial. The NeuroThera Laser System therapeutic approach involves use of infrared laser technology and has shown significant and sustained beneficial effects in animal models of ischemic stroke.

The NeuroThera Laser System (NTS) used in this NEST-1 study utilized an infrared laser technology that involves photobiostimulation. A large and growing body of scientific literature is available documenting the photobiostimulation effects of infrared laser therapy both in vitro and in vivo. The biological effects of infrared laser therapy are wavelength-specific and are not attributable to thermal effects. Energy in this region of the electromagnetic spectrum is nonionizing and, therefore, poses none of the hazards associated with UV light. It has been demonstrated that irradiation of specific infrared wavelengths is able to penetrate deeply into the brain. This form of therapy is distinguished from photodynamic therapy, which involves using light energy to penetrate the body and to activate a photosensitive drug.

Photobiostimulation involves increased adenosine triphosphate (ATP) formation after energy absorption inside mitochondria. A compound that absorbs energy in the spectral region of interest is known as a chromophore. There is evidence that suggests that a primary mitochondrial chromophore for photobiostimulation is cytochrome c oxidase. This enzyme complex contains 2 copper centers, $Cu_A$ and $Cu_B$. The primary chromophore for the NTS wavelength is in the $Cu_A$ center which has a broad absorption peak around 830 nm in its oxidized form. The NTS delivers energy at 808 nm, which is within this absorption peak, and is able to penetrate into the brain noninvasively. Cytochrome c oxidase is a terminal enzyme in the cellular respiratory chain and is located in the inner mitochondrial membrane. It plays a central role in the bioenergetics of eukaryotic cells by delivering protons across the inner membrane, and thereby driving the formation of ATP by oxidative phosphorylation. In addition to leading to increased ATP formation, photobiostimulation may also initiate secondary cell-signaling pathways. The overall result is improved energy metabolism, enhanced cell viability, and may also involve prevention of apoptosis in the ischemic penumbra and enhancement of neurorecovery mechanisms.

In vivo studies have suggested that infrared laser therapy could be beneficial for the treatment of acute myocardial infarction, acute ischemic stroke, injured peripheral nerves and spinal cord injury. Previous studies have shown in 2 different animal models a positive impact of infrared laser therapy on the experimental, ischemic stroke treatment outcomes in New Zealand rabbits (rabbit small clot embolic stroke model [RSCEM]) and Sprague-Dawley rats (permanent middle cerebral artery occlusion). Lapchak has shown that laser treatment at 6 hours poststroke onset in RSCEM improved behavioral performance and produced a durable effect that was measurable 21 days after embolization. De Taboada and Oron have also shown that laser treatment up to 24 hours poststroke onset in permanent middle cerebral artery occlusion showed significant improvement in neurological deficits which was evident at 14, 21 and 28 days poststroke when compared with the sham control group. Currently, the putative mechanism for infrared laser therapy in stroke involves the stimulation of mitochondria, which then leads to preservation of tissue in the ischemic penumbra and enhanced neurorecovery. The exact mechanistic pathways remain to be elucidated.

Study Design

NEST-1 was a prospective, multicenter, international, double-blind, randomized, sham (placebo) controlled trial conducted at 6 medical centers in 3 countries: Israel, Peru, and Sweden. The study examined initial safety and effectiveness of infrared wavelength laser therapy for treatment of patients within 24 hours of ischemic stroke onset.

This study was conducted in accordance with the FDA/ICH Good Clinical Practice guidelines and applicable local regulatory requirements. Investigators were required to ensure that this study was conducted in full conformity with the 1983 revision of the Declaration of Helsinki or with the laws and current regulations in biomedical research involving human patients of the country in which the study was conducted, whichever afforded greater protection to the patients. The protocol and information for patients and healthcare providers was approved by each center's ethics committee or Institutional Review Board. Country-specific independent data monitoring committees conducted safety reviews throughout the study.

Eligible patients were required to be between 40 to 85 years of age, have a clinical diagnosis (within 24 hours of stroke onset) of ischemic stroke causing a measurable neurological deficit (total NIHSS score ranging from 7 to 22 at admittance to the medical center), and to have NTS treatment initiated within 24 hours from stroke onset. The patient or parent legal representative gave written informed consent before enrollment into the study.

Ineligibility Criteria

Patients were excluded if: there was evidence on a CT scan of an intracranial, subdural or subarachnoid hemorrhage, or clinical presentation suggestive of subarachnoid hemorrhage, even if the initial CT scan was normal; the patient was a candidate for intravenous or intra-arterial administration of tissue-type plasminogen activator or other thrombolytic therapy for treatment of the acute ischemic stroke, and tissue plasminogen activator or other thrombolytic therapy was administered; the patient had a seizure at stroke onset; serum blood glucose was >400 mg/dL (22 mmol/L) or <40 mg/dL (2.2 mmol/L); the patient had sustained hypertension (defined during the baseline period by 2 readings occurring 30 minutes apart with systolic blood pressure>185 mmHg or diastolic blood pressure>110 mmHg) at time of treatment or need for aggressive treatment for blood pressure reduction; there was sustained hypotension (defined as systolic blood pressure<80 mmHg, or diastolic blood pressure<50 mmHg); there was presumed septic embolus; the patient had known hereditary or acquired hemorrhagic diathesis, e.g., activated partial thromboplastin time or prothrombin time greater than normal, unsupported coagulation factor deficiency, or oral anticoagulant therapy with the prothrombin time greater than normal; the patient had a skin condition (i.e., hemangioma, scleroderma, psoriasis, rash, or open wound) at the site chosen for infrared energy application; the patient was previously enrolled in or had participated in another investigational drug or device trial within the preceding 4 weeks; if a new medication was started within 14 days before the screening visit; the participant had severe mental deficit, severe neurological deficit or disorder (dementia, multi-infarct dementia, advanced multiple sclerosis) which would interfere with the assessment of the patient's ability for independent functioning; there was evidence of any disorder other than stroke that, in the opinion of the investigator, could be considered serious or life threatening such as active serious infections, pneumonia, pulmonary emboli, or gastrointestinal bleeding; the patient had unstable cardiac arrhythmias or other cardiac illness that, in the opinion of the investigator, was life threatening; the patient was of child bearing potential; the patient was comatose or moribund level of consciousness; or the patient was otherwise determined by the investigator to be medically unsuitable for participation in this study.

Study Groups, Evaluation Measures, and Baseline Factors

All patients received standard medical management therapy for acute ischemic stroke. In addition, they all underwent an identical NTS procedure. A randomization code that was preprogrammed within the NeuroThera Laser System determined whether the treatment was active or sham (placebo). Both patients and clinicians were blinded regarding treatment arm. The National Institutes of Health Stroke Scale (NIHSS) was assessed at the time of screening for entry into the study and again immediately before randomization to treatment group. Outcome measures (NIHSS, modified Rankin Scale [mRS], Barthel Index, and Glasgow Outcome Scale) were determined at 30, 60, and 90 days. Neurological scores and clinical data were collected on standard case report forms at each visit by trained investigators.

Baseline factors including patient demographics, time to treatment, medical history, vital signs, and routine laboratory values were collected. Factors also included age, sex, time from stroke onset to arrival at hospital, time from stroke onset to treatment, and a complete medical history.

After completion of the NTS procedure, patients entered the study follow-up phase until one of the following occurred: the patient decided to stop participation in the study; the sponsor or ethics committee/applicable regulatory body terminated the study; the investigator decided to discontinue the patient or site participation in the study; or the patient had participated in the study for 90±10 days.

The NTS Treatment Device

The NTS used in the NEST-1 study was an investigational device intended to provide noninvasive, transcranial laser treatment to patients diagnosed with acute ischemic stroke. The laser wavelength of 808 nm is in the near-infrared portion of the electromagnetic spectrum, and is invisible to the naked eye. Energy in the near-infrared spectrum is nonionizing and is not associated with the risks of ionizing radiation. The NTS device used in the NEST-1 study included a class IV laser system and delivers energy via a fiber optic cable to a handheld probe that is placed on the shaved head of the patient by a trained operator. The device is portable and is similar in size to portable ultrasound equipment.

The NTS is manufactured by PhotoThera, Inc. A complete treatment regimen as defined for the NEST-1 study included removing hair from the patient's scalp, followed by NTS application (active treatment or sham/control treatment) on 20 predetermined locations on the scalp for 2 minutes at each site. The predetermined sites are identified by a cap which is placed on the patients head. The system is designed to deliver about 1 Joule/cm$^2$ of energy over the entire surface of the cortex regardless of stroke location. The sham procedure is identical to the active procedure with the exception that no laser energy is delivered to the patient from the device.

Based on current knowledge of the technology and risk assessment analysis, the most significant known hazard with NTS treatment is potential retinal damage if the beam enters through the lens of the eye and onto the retina. Other potential hazards include skin burns and cuts to the scalp from shaving the head. Skin burns could occur if the device is not used as intended (eg, repeated treatments at the same location).

Statistical Methods

Effectiveness outcomes were reported on an intention-to-treat basis and include all 120 patients randomized to both arms. Safety outcomes were based on the same 120 patients, who also comprised all patients who received any treatment.

Patients were evaluated at baseline, 30, 60, and 90 days after baseline. Analysis focused largely on the 90-day evaluations. The NIHSS was the prospectively identified primary outcome, and the mRS, Glasgow Outcome Scale and Barthel Index scores were secondary outcomes.

Categories of baseline values of the NIHSS score and of time from stroke onset to treatment were entered into the analyses as strata or covariates. The three NIHSS strata were 7 to 10, 11 to 15, and 16 to 22. The categories for time from stroke onset to treatment were "less than 12 hours" and "12 to 24 hours." The NIHSS scale is not an interval scale. Therefore, categories of the NIHSS score were used to reduce potential heterogeneity.

NIHSS outcome was collapsed into a binary outcome, bNIH, where 'success' could occur in either of 2 ways: as a 90-day NIHSS score 0 to 1 or as a decrease in score (change) of 9 or more points from baseline to 90 days.

The mRS 90-day outcome took 2 forms. The 7-category ordinal variable form, analyzed across the whole distribution of scores on the 0 to 6 mRS scale (full mRS), and a binary mRS that makes scores of 0 to 2 as positive (success) and scores of 3 to 6 as negative (failure).

The full mRS ("shift in Rankin"), binary mRS and bNIH outcomes were tested using a stratified Cochran-Mantel-Haentzel (CMH) test: namely, the van Elteren test. The test uses the modified ridit score and thereby is a direct extension of the 2-sample Wilcoxon test. For the bNIH and the binary mRS outcomes, logistic regression analyses were used to explore the effects of covariates and the random effect of site: in particular, to assess how adding these factors altered the estimate of treatment effect.

The analyses were carried out in SAS version 9 using PROC FREQ to obtain the results for the van Elteren CMH test, and using PROC GENMOD and PROC LOGISIC to obtain results for logistic regression analyses with and without medical center as a random effect. Prevalence odds ratios were obtained from PROC GENMOD.

This study was an exploratory trial rather than a confirmatory trial, in the sense of FDA/ICH E8 Guidance on General Considerations for Clinical Trials and FDA/ICH E9 Guidance on Statistical Principles for Clinical Trials. Primary safety and effectiveness outcome measures and their analysis were identified prospectively. Multiple secondary and exploratory analyses were defined in the protocol or were designed and performed after study completion and unblinding. No corrections were made for multiple comparisons.

Figure 31:
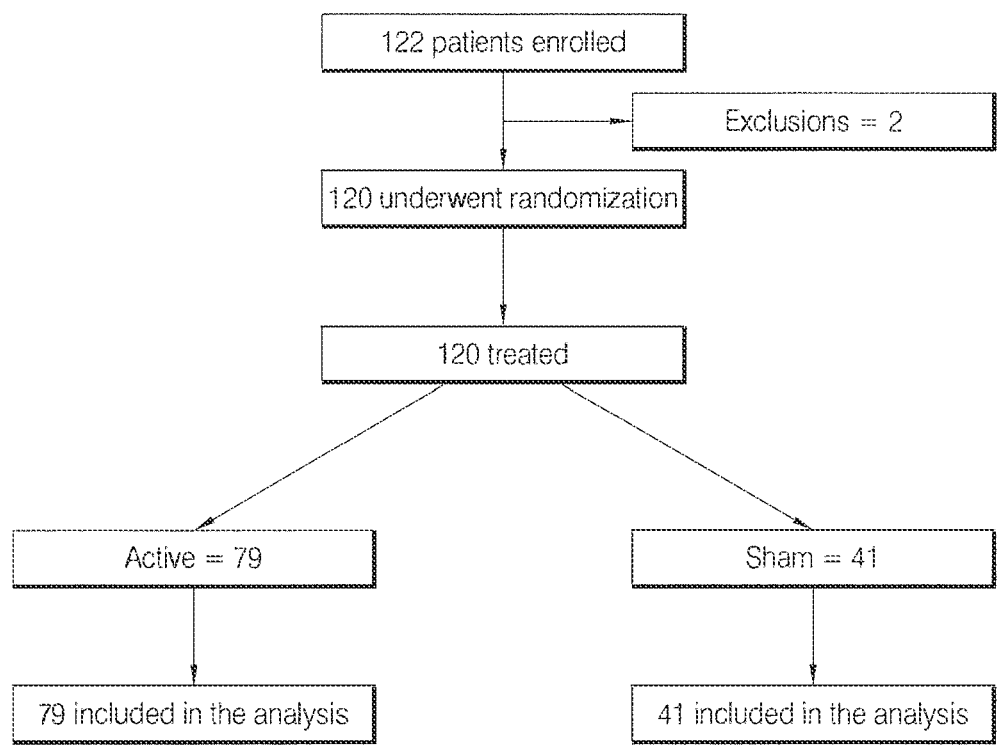
FIG. 31 shows the disposition of patients in the NEST-1 study.

The study enrolled 122 eligible adult patients, between ages 40 and 85 of any ethnic background diagnosed with acute ischemic stroke within 24 hours of onset who provided their written informed consent. Two patients withdrew before randomization and are not included in any analyses, leaving 120 patients in the effectiveness analysis. Of the 120 patients, 79 were randomized to the active treatment group and 41 were randomized to the sham control group. FIG. 31 shows the disposition of patients in the study. There was only 1 patient lost to follow-up (0.8%). No significant differences in baseline characteristics were observed (see Table 3; baseline demographics and other baseline characteristics). Study data were reviewed by independent data monitoring committees in each country; there were no serious device-related adverse effects reported.

TABLE 3

| Characteristic | Active Treatment (NTS), n = 79 | Placebo (sham control), n = 41 |
|---|---|---|
| Mean age, y | 70.2 | 68.5 |
| Female, No. (%) | 36 (45.6%) | 15 (36.6%) |
| Ethnicity, No. (%) | | |
| White | 29 (36.7%) | 17 (41.5%) |
| Black | 2 (2.5%) | 0 (0.0%) |
| Hispanic | 4 (5.1%) | 2 (4.9%) |
| Other (largely Mestizo and Native American Indians) | 44 (55.7%) | 22 (53.7%) |
| Median time to treatment, h | 18 | 17 |
| Mean time to treatment, hr:min | 16:56 | 16:20 |
| Mimimum, hr:min | 02:00 | 04:05 |
| Maximum, hr.min | 23:56 | 23:22 |
| Median NIHSS score at entry | 11 | 10 |
| First quartile | 9 | 9 |
| Third quartile | 15 | 14 |
| History, No. (%) | | |
| Hypertension | 44 (55.7%) | 20 (48.8%) |
| Previous stroke | 17 (21.5%) | 12 (29.3%) |
| Diabetes mellitus | 20 (25.3%) | 9 (22.0%) |

Effectiveness Analysis

The proportion of patients who received active treatment and had a positive bNIH outcome was 70%, which is greater than the proportion who received sham control treatment with a positive bNIH outcome (51%; CMH test P=0.035 stratified by severity and time from stroke onset to treatment; P=0.048 stratified only by severity). The treatment effect remained significant with other choices of strata for the CMH analysis. Logistic regression analyses confirmed that the results held controlling for both fixed covariates (eg, age, sex, time-to-treatment, baseline severity, previous stroke) and the random effects of medical site. Controlling only for baseline severity the logistic regression gave a prevalence odds ratio favoring treatment of 1.40 (95% CI, 1.01 to 1.93). Among the 79 treated patients, 38% achieved both a final NIHSS score of 0 to 1 and improved by 29 points, 20% had only a 29-point improvement, 11% obtained a final score of 0 to 1 without improving by 29, and 30% achieved neither end point. Among the 41 control patients the corresponding proportions were 29%, 7%, 15%, and 49%.

Figure 32:
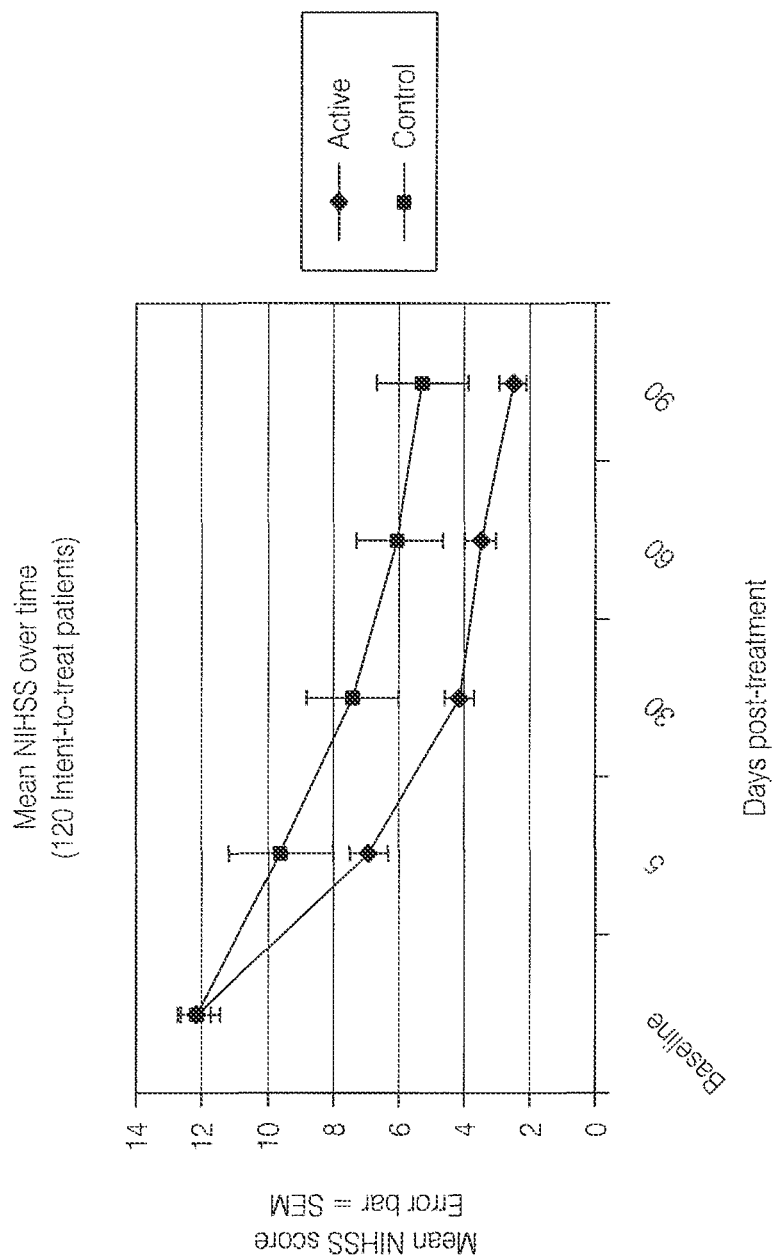
FIG. 32 shows the mean NIHSS over time for each treatment group of the NEST-1 study.

Differences in mean NIHSS scores between the treatment groups appeared soon after treatment and were apparent throughout the 90-day study period. FIG. 32 shows the mean NIHSS over time for each treatment group. Patients in the active treatment group showed greater improvement in the change in NIHSS scores from baseline to day 90, as compared with the sham control group (P=0.021, CMH test stratified by time to treatment).

For the binary mRS outcome (0 to 2 versus 3 to 6), a similar pattern of significance held. The proportion of patients who received active treatment and had a positive binary mRS outcome was 60%, which is greater than the proportion who received sham control treatment with a positive binary mRS outcome (44%; CMH test P=0.034 stratified by severity and time to treatment; P=0.043 stratified only by severity). Only the CMH test without strata was not significant (P<0.11 $\chi^2$ test). The rate of positive results markedly varies across the baseline severity strata. Controlling only for baseline severity, logistic regression gave prevalence odds ratios favoring treatment of 1.38 (95% CI, 1.03 to 1.83) for the binary mRS outcome.

The effect of the NTS when compared with sham treatments with respect to the score on the full mRS at 90 days or the last rating, analyzed across the whole distribution of scores on the 0 to 6 mRS scale was significant, with the use of the Cochran-Mantel-Haentzel nonparametric rank test, stratified by categories of (1) baseline NIHSS score and time to treatment (P=0.020) and (2) baseline NIHSS score only (P=0.026; see Table 4).

TABLE 4

| mRS | 0 | 1 | 2 | 3 | 4 | 5 | 6 | Total |
|---|---|---|---|---|---|---|---|---|
| Control | 5 | 10 | 3 | 8 | 6 | 5 | 4 | 41 |
| % | 12.20 | 24.39 | 7.32 | 19.51 | 14.63 | 12.20 | 9.75 | |
| Active | 12 | 25 | 10 | 11 | 12 | 2 | 7 | 79 |
| % | 15.19 | 31.65 | 12.66 | 13.92 | 15.19 | 2.53 | 8.86 | |
| Total | 17 | 35 | 13 | 19 | 18 | 7 | 11 | 120 |

Figure 33:
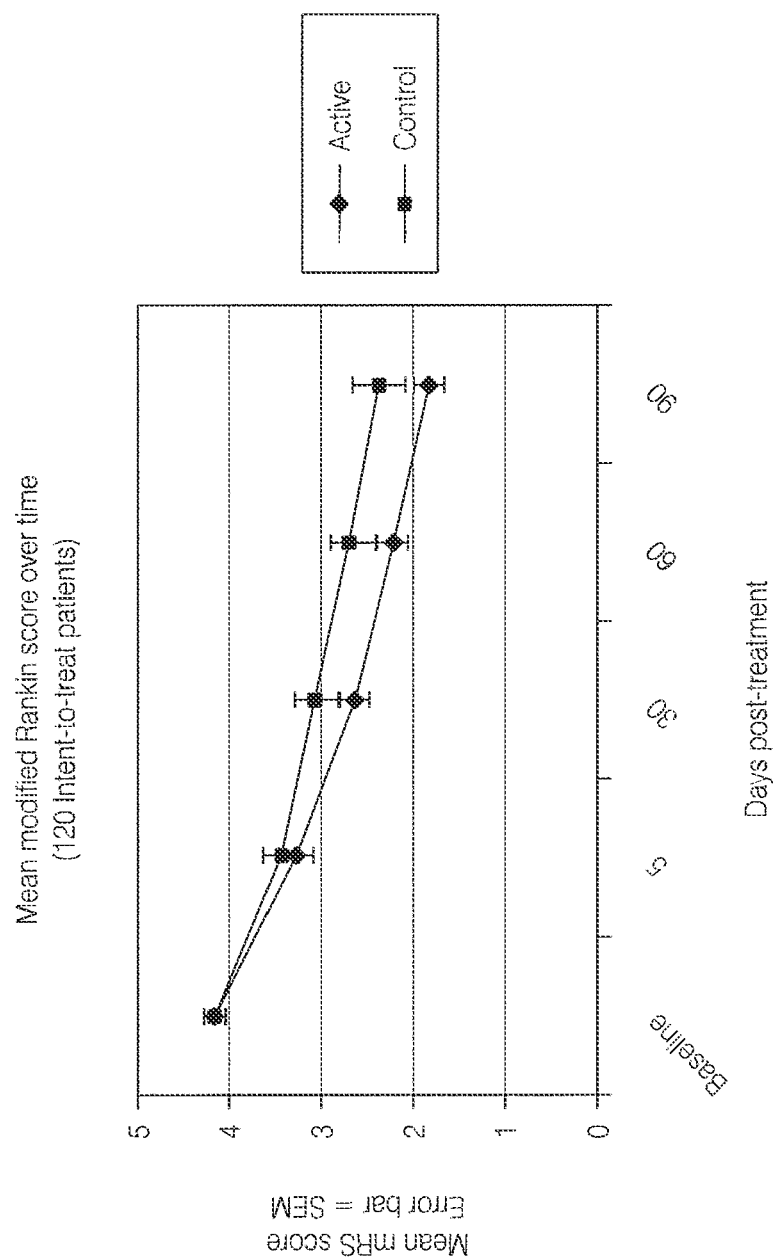
FIG. 33 shows the mean mRS over time for each treatment group of the NEST-1 study.

FIG. 33 shows the mean nRS over time for each treatment group. Stratification by baseline severity gave similar results for the 3 outcomes (bNIH, binary mRS, and full mRS); all 3 outcomes had significance levels<0.05 (see Table 5; 2-sided significance levels for the van Elteren CMH test). When also controlled for time-to-treatment (0 to 12 hours versus 12 to 24 hours) little significance is gained. However, in a trial with a larger sample size, time-to-treatment would be expected to have a stronger association with outcome.

TABLE 5

| Outcome | Stratified by Severity Only | Stratified by Severity and Time-to-Treatment |
|---|---|---|
| Binary_NIH | 0.048 | 0.035 |
| Binary_mRS | 0.043 | 0.034 |
| Full mRS | 0.026 | 0.020 |

Results of analyses using the Glasgow Outcome Scale and Barthel Index are similar to those for the NIHSS and the mRS. Patients who received active treatment had better outcomes than patients who received sham control treatment as measured on the Glasgow Outcome Scale (CMH test P=0.056), and the Barthel Index scale (CMH test P=0.035), stratified by baseline NIHSS score and time to treatment.

The logistic regression analyses indicated the negligible effects of covariate adjustment on the logistic regression coefficient for treatment. The results in Table 6 indicate that treatment effect is stable across 2 binary outcomes and across 3 different nested sets of covariates. In fact, the treatment effect tends to increase as covariates are added. Furthermore, treating hospital site as a repeated measures effect virtually does not alter the logistic regression coefficient for treatment. The 95% CIs are not shown to focus on the consistency of the regression coefficients. In all but one model the probability value for treatment is <5%. In the models with the bNIH outcome, the covariate 'severity' is not significant and time-to-treatment is significant only once with P=0.0496. However with the binary mRS outcome, the covariate 'severity' is significant with P<0.001 in all 3 models. This indicates that the 9-point decrease in the NIHSS score captures the variation of treatment effect across the baseline severity categories. We explored many sets of additional covariates and found that after including the covariates 'gender', 'age', and 'prior stroke' all other covariates had negligible predictive value. Gender was significant in the binary mRS model with P<0.01. Otherwise, these factors did not achieve statistical significance. See Table 6 which shows the results for two sets of nested multivariate models, 1 set of models with outcome bNIH and 1 set of models with outcome binary mRS (time-to-tx indicates time from onset to treatment). The first P value is for simple logistic regression and the second P value is for logistic regression with the factor 'site' included as a repeated measures effect.

TABLE 6

| Covariates in Model | Outcome bNIH TX Coefficient and (P values)* | Outcome Binary mRS TX Coefficient and (P values)* |
|---|---|---|
| Severity | 0.82 (0.046) | 0.92 (0.044) |
| | 0.82 (0.007) | 0.92 (0.095) |
| Severity and time-to-tx | 0.89 (0.034) | 1.03 (0.027) |
| | 0.89 (0.009) | 1.03 (0.032) |
| Severity, time-to-tx, gender, age, prior stroke | 0.99 (0.027) | 1.43 (0.009) |
| | 0.99 (0.010) | 1.44 (0.020) |

Safety Analysis

Table 7 (mortality rates and SAEs) shows the mortality rates and SAES by treatment group and totals. No significant difference in mortality between the active treatment group and the sham control group is evident. Table_7 shows the number of patients with serious adverse events, worsening of underlying disease, cardiovascular SAEs, infection, or central nervous system SAEs, in total and by treatment group. These data indicate that there were no significant differences between the treatment groups with respect to these measures. Where there was a trend toward differences between the treatment groups, such as in rates of infection or rates of central nervous system SAEs, the patients receiving active treatment appear to have had better outcomes than patients receiving sham control treatment.

TABLE 7

| No. of Patients with: | Total, n = 120 | Percent | Active, n = 79 | Percent | Sham, n = 41 | Percent | Fisher Exact, P Value |
|---|---|---|---|---|---|---|---|
| Mortality (all sites) | 11 | 9.2% | 7 | 8.9% | 4 | 9.8 | 0.87 |
| SAEs | 35 | 29.2% | 20 | 25.3% | 15 | 36.6 | 0.211 |
| Worsening of underlying disease | 8 | 6.7% | 3 | 3.8% | 5 | 12.2 | 0.120 |
| CVS | 8 | 6.7% | 5 | 6.3% | 3 | 7.3 | 1.000 |
| Infection | 13 | 10.8% | 5 | 6.3% | 8 | 19.5 | 0.059 |
| CNS | 14 | 11.7% | 6 | 7.6% | 8 | 19.5 | 0.072 |

Discussion

The NEST-1 trial provides initial evidence on the safety and effectiveness of infrared laser therapy for the treatment of ischemic stroke in humans within 24 hours of stroke onset. The outcome variable scales used in the NEST-1 study had excellent correlation. R=0.79 to 0.92. The correlation coefficients for the NEST-1 trial are essentially the same as those reported in the article by Lyden and colleagues reviewing tissue plasminogen activator data. That is, the outcome variables have correlation coefficients with each other of about 0.8 (absolute value) or higher. This concordance with prior studies is evidence that the outcomes are being measured appropriately and consistently.

The results suggest that infrared laser therapy may benefit a broad spectrum of stroke patients without increasing the rate of adverse events. Furthermore, the relatively large magnitude of the effect implies that a phase III trial should not require a substantial number of subjects.

Patients receiving active treatment had a higher proportion of positive NIHSS outcomes than did patients receiving sham control treatment. Results were similar using the other neurological outcome scales. No significant differences between the treatment groups were observed in rates of mortality or SAEs, but the sample size (n=120) gives low power to detect small differences. Where there is a trend toward differences between the treatment groups, patients receiving active treatment appeared to have had fewer SAEs than did patients receiving sham control treatment. The safety profile of the NTS treatment as demonstrated in this study was clear. There were no adverse outcomes that can be attributed to the laser therapeutic procedure.

The bNIH outcome with the 9-point change incorporates variation in baseline severity (from NIHSS score 7 to 22) and suggests a global potential benefit. In contrast, the binary mRS outcome does not account for change from baseline. Thus, once the analysis controlled for baseline severity, the results based on the 2 binary outcomes closely agreed. Controlling for baseline severity, the analyses by the CMH test and by logistic regression gave prevalence odds ratios favoring treatment exceeding 1.40 for the bNIH outcome and exceeding 1.38 for the binary mRS outcome.

This global potential benefit is also demonstrated through the full mRS, analyzed across the entire distribution of Rankin scores, from 0 to 6. The mRS is a simple and reliable outcome measure when consistently implemented by trained clinicians. The full mRS analysis takes into consideration the entire spectrum of the patient outcomes. As a result, the full mRS is increasingly considered as a primary outcome measure for ischemic stroke trials involving neuroprotective technologies.

This exploratory study had a prespecified analytic plan with a primary outcome of bNIH, the binary form of NIHSS that regards a final score of 0 to 1 or a 9-point decrease as a success. But our presentation of several analytic approaches raises the concern of type 1 error. We described several approaches to the same hypothesis: some having an mRS outcome, some having an NIHSS outcome, and some using logistic regression to confirm the nonparametric results. These results showed the substantial concordance among these outcomes and methods. Also, they showed that after control for NIHSS baseline severity, other factors had little or no effect on the magnitude of the treatment effect. Hence, we did not present a multiple comparisons correction such as the Bonferroni correction because, in particular, the Bonferroni correction assumes that the hypotheses are independent of one another. Another reason for the various analyses was to associate an effect size with the results of the primary analysis by the nonparametric CMH test. Simple estimates of effect size were obtained from the other tests and both the simple proportions of success for the binary outcomes and prevalence odds ratios obtained from logistic regression were reported.

An extended treatment window of up to 24 hours after stroke onset will have a number of implications. Thrombolytics have a proven treatment window of 3 hours, although it may be that effectiveness for this form of therapy extends out somewhat further. The first neuroprotective trial to show efficacy was the study of NXY-059. That study had a 6-hour treatment window, but a majority of patients were treated within 4 hours. It is a reasonable contention that the reason the NXY-059 study was successful, whereas all the previous neuroprotective therapies were not, was that the average time to treatment was kept so low. NEST-1 had a 24-hour treatment window and a much longer time to treatment (median 18 hours) than nearly all other clinical trials to date for the treatment of acute ischemic stroke. A major problem for treatment of strokes has been that large numbers of patients present after 6 hours. Therefore, an expanded treatment window of 24 hours would make it possible to treat many more ischemic stroke victims.

Although the mechanism of action of infrared laser therapy for stroke is not completely understood, a number of effects of this type of irradiation have been documented. Infrared laser therapy is a physical process that can produce biochemical changes at the tissue level. The putative mechanism for NTS treatment involves stimulation of ATP formation by mitochondria and may also involve prevention of apoptosis in the ischemic penumbra and enhancement of neurorecovery mechanisms. An example of another physical process that reduces neurological damage is hypothermia. In animal model studies, there are few, if any therapies that have been shown as consistently to reduce stroke-related damage as hypothermia. What is clear is that infrared irradiation is probably delivering its effect independent of restoration of blood flow and the mechanism is probably related to an improved energy metabolism and enhanced cell viability.

Other advantages of this form of therapy are that treatment can be started rapidly, without any need for preliminary laboratory testing, invasive procedures, or extensive training of the clinicians who administer the treatment. Furthermore, it is not necessary to know the location of the vascular occlusion to administer the NTS treatment. Thus, this form of therapy is likely to require much less infrastructure than virtually all other types of devices and medical therapies available to date for acute stroke treatment or clot removal.

Although the NEST-1 study results are encouraging, and may indicate that infrared laser therapy has potential to become a treatment of ischemic stroke in humans when initiated within 24 hours of stroke onset, a larger confirmatory trial to demonstrate safety and effectiveness is warranted.

Phototherapy Example 2

Another example of phototherapy (NeuroThera Effectiveness and Safety Trial-2 (NEST-2) was nearly identical to the trial study discussed above, but was larger and included patients 40 to 90 years of age. NEST-2 was a double blind, placebo (sham) controlled trial in which 660 patients were enrolled at 57 centers in 4 countries. Patients were eligible for inclusion in the study if they were 40 to 90 years of age, had a baseline NIHSS score between 7 to 22, had a clinical diagnosis of ischemic stroke, no evidence of hemorrhagic infarct by CT scan or MRI, and had not received tPA. Initiation of treatment had to occur within 24 hours after stroke onset. The inclusion and exclusion criteria are summarized in Table 8.

TABLE 8

Major Inclusion and Exclusion Criteria

Inclusion 40-90 years of age
Diagnosis of acute ischemic stroke within 24 hours of onset
NIHSS ≥7-≤22
Informed consent
Exclusion Evidence of intracranial, subdural, or subarachnoid hemorrhage
Prestroke ≥3 mRS
Clinical diagnosis of a brain stem or cerebellar stroke
Seizure at onset
Blood glucose >400 or <60
Sustained systolic BP >220 mm Hg, <80 mm Hg or diastolic >140 mm Hg, <50 mm Hg
Suspected septic embolus
CNS tumor (except asymptomatic meningioma)
Dermatologic conditions (eg., psoriasis) of the scalp
Thrombolytic stroke therapy
Head implant (eg, clipped aneurysm, Hakim valve)
Photodynamic therapy within 14 days (eg, Visudyne)
Pregnancy
Severe comorbidities
CNS indicates central nervous system.

Randomization and Treatment

Patients were randomly assigned in a 1:1 ratio to receive either TLT or sham. All patients underwent the identical TLT procedure that involves removal of the patient's scalp hair followed by application of a laser probe to the patient's head. The total procedure time was approximately 2 hours. After consent, an interactive voice randomization system was used, with dynamic randomization at centers to ensure balanced distribution of treatment assignments. All patients received standard of care medical management throughout the course of trial.

Study Management

This study was conducted in accordance with the FDA/ICH Good Clinical Practice (GCP) guidelines and applicable local regulatory requirements. The trial was also conducted in full conformity with the 1983 revision of the Declaration of Helsinki or with the laws and current regulations in biomedical research involving human patients of the country in which the study was conducted, whichever afforded greater protection to the patients. The study was designed and overseen by the steering committee. Each center's ethics committee or Institutional Review Board and an independent data monitoring committee (DMC) conducted safety reviews. The DMC periodically reviewed serious adverse event data between the groups. The patient or legal representative gave written informed consent before enrollment into the study. Data management and statistical analysis was conducted by an independent contract research organization (Parexel, Waltham, Mass), as well as by the study sponsor (PhotoThera, Carlsbad, Calif). After database lock and independent review by the DMC, the steering committee had complete access to the trial data and assumed responsibility for the analysis and interpretation of the results.

Treatment

The NeuroThera Laser System (NTS) included an apparatus with a hand-held housing to apply the light to selected portions of the patient's scalp. The NTS uses energy at a wavelength of 808 nm which is near-infrared, nonionizing, and is invisible to the naked eye. Experiments using cadavers indicated that optimal amounts of laser energy are able to penetrate the brain to a depth of approximately 2 cm. The dosimetry of wavelength and irradiance levels was based on transmission experiments with fresh human cadavers without fixation. Monte Carlo simulations, in vitro experiments, review of the literature using infrared therapy for other indications and the results of preclinical studies in validated stroke animal models. A complete treatment regimen as defined for the NEST-2 study included applying the hand-held probe on 20 predetermined locations on the shaved scalp for 2 minutes at each site. The predetermined sites, which are irrespective of stroke location, are identified by a cap which is placed on the patient's head. The sham procedure is identical to the TLT procedure with the exception that no laser energy is delivered to the patient from the device.

Based on current knowledge of the technology and risk assessment analysis, the most significant known hazard with TLT is potential retinal damage if the beam enters the eye and is focused onto the retina which could result in permanent eye injury. Because of this potential ocular hazard, the procedure must be conducted in a laser safe environment by a trained user.

Clinical Assessments

Patients were assessed by examiners who were unaware of the treatment group. All examiners were trained on the NIHSS and certified on the mRS. The NIHSS is a neurological function scale that ranges from 0 to 42: scores between 7 and 22 are considered to represent moderate to severe neurological impairment. The mRS is a disability index ranging from 0 (no symptoms) to 6 (death). Outcome measures (mRS and NIHSS) were assessed, in addition to baseline, at 5, 30, 60, and 90 days. Baseline data were collected including age, sex, patient demographics, time from stroke onset to arrival at hospital, time to treatment, prestroke mRS, vital signs, and a complete medical history.

Safety Assessments

Vital signs, neurological scores, concomitant medications, adverse events, and serious adverse events were recorded from study entry to day 90. Unresolved serious adverse events were followed for an additional 30 days.

The Data Monitoring Committee examined rates of death, adverse events, and serious adverse events, as well as anticipated and unanticipated device effects during the study. After evaluating the safety data for the first 100 and 400 patients, they did not stop further recruitment into the trial. Because of rapid enrollment, there was no efficacy interim analysis. Neuroimaging assessments were completed at baseline and at 5-day follow-up±2 days.

Statistical Analysis

All analyses are intention-to-treat. Outcomes were obtained from two 90-day scores, the mRS and the NIHSS score. Patients without a day-90 visit had their last observation carried forward. The mRS outcomes were: (1) the entire ordinal scale 0 to 6; and (2) a dichotomous outcome with a favorable outcome (success) defined as a 0 to 2 score and an unfavorable outcome (failure) defined as a 3 to 6 score. The NIHSS outcomes were: (1) the change in score from baseline to 90 days using the entire ordinal scale 0 to 42 (with death scored as 42); and (2) a dichotomous outcome for which success could be achieved in 2 ways, either as a 90-day score of 0 to 1 or as a beneficial change from baseline to 90 days of 9 or more points.

The primary efficacy outcome measure was the dichotomous mRS 90-day end point with success (mRS 0 to 2) and failure (mRS 3 to 6). The null hypothesis that the proportion of successes did not differ by treatment, was tested using multiple logistic regression with 2 prespecified covariates: (1) stroke severity at baseline; and (2) time from stroke onset to time of randomization (TFSO). Baseline stroke severity had 3 levels: NIHSS score 7 to 10 (moderate), 11 to 15 (moderately severe), and 16 to 22 (severe). TFSO had 2 levels: 0 to 12 hours and 12 to 24 hours. The randomization procedure was balanced on (but not stratified by) these factors.

Secondary analyses determined the sensitivity of results to the choice of covariates, of test procedure, and of analytic outcome. The logistic model was run on the primary outcome measure with additional covariates: age, sex, history of CAD, history of diabetes, and history of stroke. To vary the test procedure of logistic regression with a dichotomous outcome, we used the nonparametric 'shift' test with the same dichotomous outcome. Explicitly, the shift test is the Cochran-Mantel-Haenszel (CMH) test with ridit scores to rank outcomes (the van Elteren test, Stokes M E, Davis C S, Koch G C. Categorical Data Analysis Using the SAS System II Cary, NC: SAS Institute, Inc; 2000). In the stroke literature, the shift test has often only been applied to the full range of the mRS scale, but we applied it to all dichotomous and ordinal outcomes. Logistic regression as run using only dichotomous outcomes. All tests were adjusted for baseline severity and TFSO. Odds ratios were calculated only for tests with dichotomous outcomes.

The safety end points included mortality and all adverse events including procedure and device related adverse events. Safety end points were summarized with descriptive statistics and tables. The analyses were carried out in SAS version 9.1.

Results

Baseline Characteristics

Figure 34:
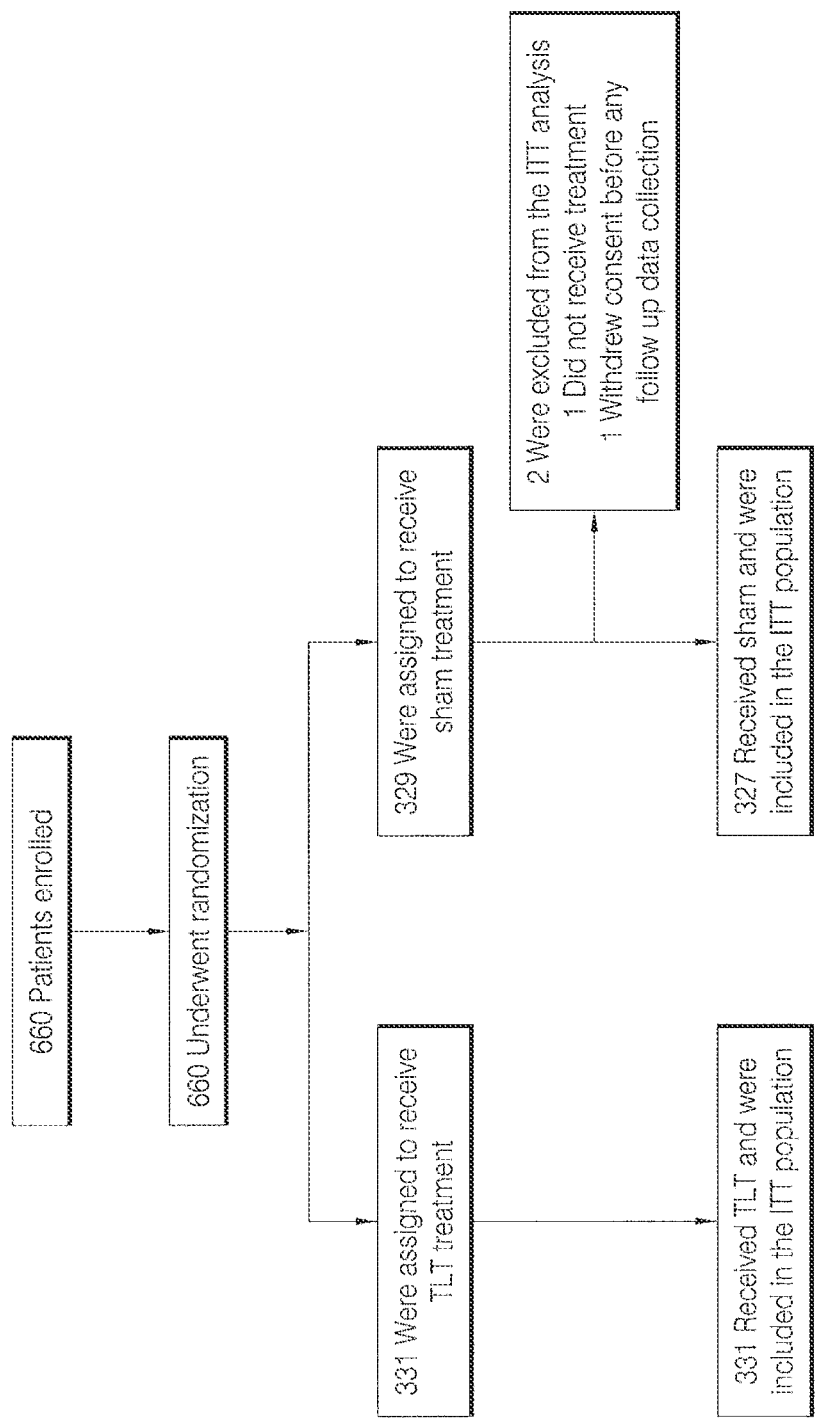
FIG. 34 shows the disposition of patients for the NEST-2 study.

The patients were enrolled between January 2007 and April 2008. A total 660 patients were randomized (331 TLT and 327 sham), as shown in FIG. 34. There were 7 (1.1%) patients lost to follow-up. The groups were balanced with respect to baseline characteristics (see Table 9). Mean time from stroke onset was 14.6±5.9 hours (range 2.7 to 23.9) for the TLT group and 14.7±6.1 hours (range 2.5 to 23.9) for the sham group; median times were 15 hours and 16 hours for the TLT group and sham group, respectively. Baseline NIHSS means scores were 13.1 (range 7 to 22) for TLT and 13.2 (range 7 to 23) for sham. Median NIHSS scores were 12 for TLT and 13 for sham.

TABLE 9

Demographic and Baseline Characteristics

|  | TLT (n = 331) | Sham (n = 327) |
|---|---|---|
| Age (y) | 70.4 ± 12.6 | 70.0 ± 11.9 |
| Male (%) | 55.3 | 57.8 |
| Ethnicity (No., %) | | |
| White | 256 (77%) | 254 (77%) |
| Black | 37 (11%) | 38 (12%) |
| Hispanic | 7 (2%) | 8 (2%) |
| Other (Largely Mestizo and Native American Indians) | 31 (10%) | 29 (9%) |
| Time | | |
| Median time to treatment (h) | 15 | 16 |
| Mean time to treatment (h:min) | 14.38 ± 5:55 | 14:43 ± 6:12 |
| Min (h:min) | 2:42 | 2:30 |
| Max (h:min) | 23:54 | 23:54 |
| Range (h) | 3-24 | 3-24 |
| Time to treatment strata (%) | | |
| <12 h | 35.6 | 35.6 |
| 12-24 h | 64.4 | 64.4 |
| NIHSS score | | |
| Mean | 13.1 ± 4.7 | 13.2 ± 3.6 |
| NIHSS score strata (%) | | |
| Median | 12 | 13 |
| Mean 7-10 | 39.0 | 38.9 |
| 11-15 | 26.6 | 27.1 |
| 16-22 | 34.4 | 34.0 |
| History (%) | | |
| Diabetes | 31.4 | 33.4 |
| Hypertension | 82.2 | 83.9 |
| Atrial fibrillation | 38.7 | 35.6 |
| Current smoker | 20.2 | 19.1 |

Clinical Outcomes

Figure 35:
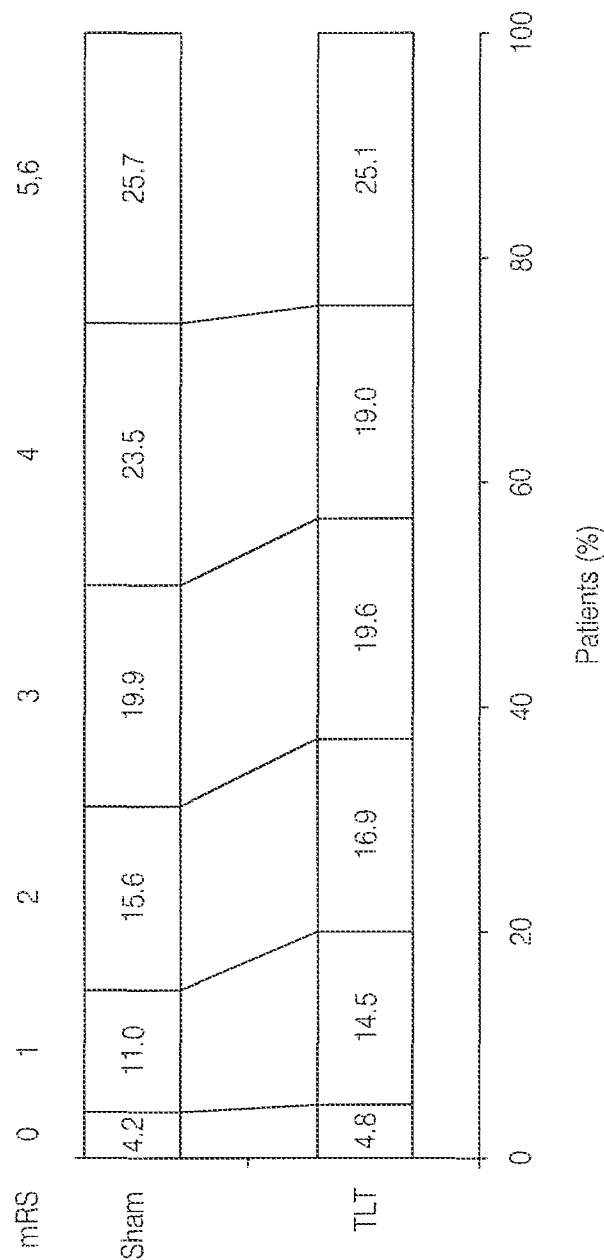
FIG. 35 shows the distribution of scores on the mRS for the NEST-2 study.

Of the 660 patients: 331 received TLT and 327 received sham; 120 (36.3%) in the TLT group achieved successful outcome versus 101 (30.9%), in the sham group (P=0.094). OR 1.38 (95% CI, 0.95 to 2.00) as shown in FIG. 35, which shows the distribution of scores on the mRS. The scores on the mRS indicate the following: 0, no symptoms at all; 1, no significant disability despite symptoms; 2, slight; 3, moderate; 4, moderately severe; 5, severe disability; 6, death.

Figure 36:
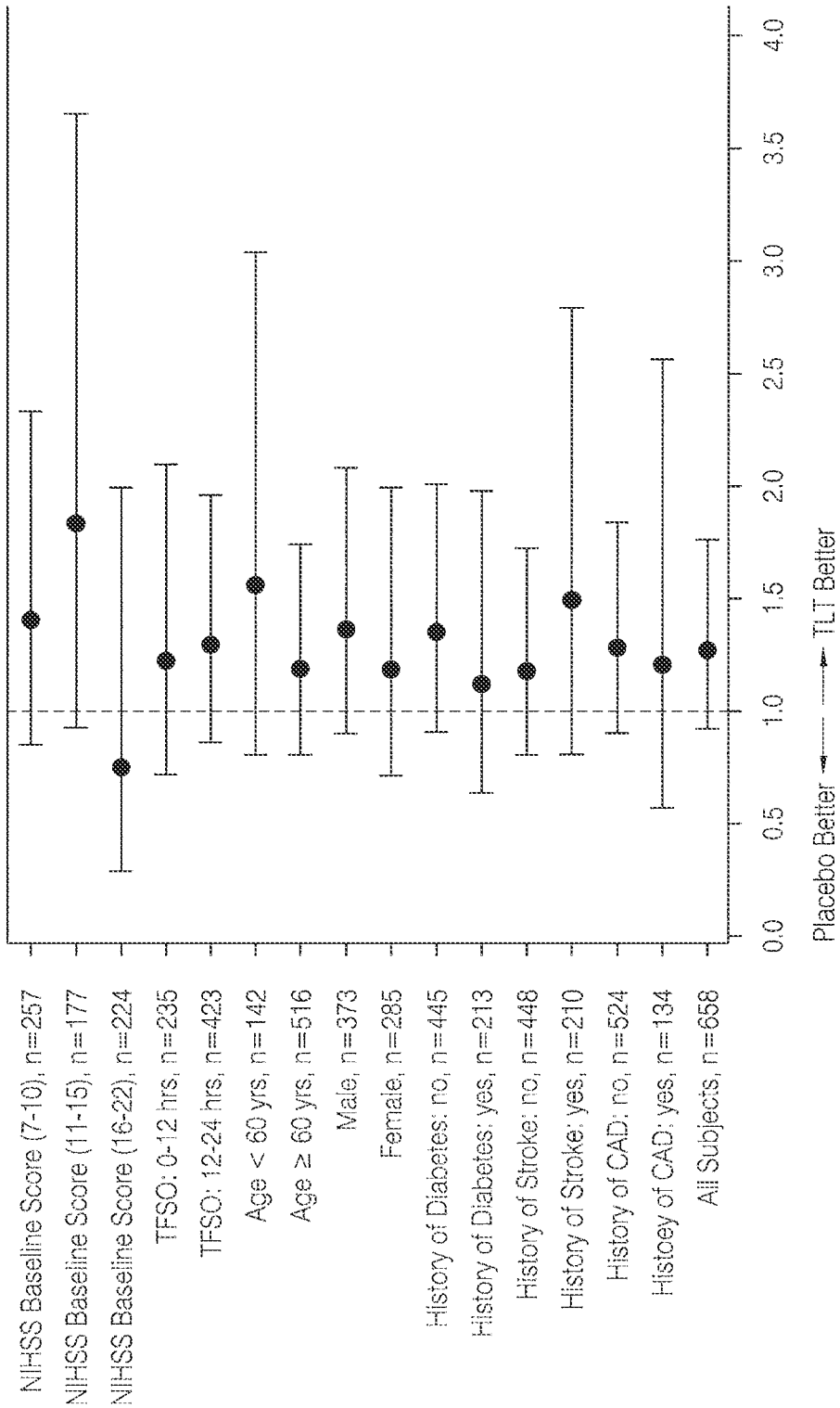
FIG. 36 shows the effects of TLT on the primary end point, on subsets of the data defined by categories of selected baseline characteristics for the NEST-2 study.

The results of secondary analyses on the prespecified outcomes were consistent with those of the primary analysis. The logistic regression analysis of the primary outcome measure with additional covariates yielded a treatment OR-1.34 (95% CI, 0.94 to 2.03). All covariates except sex and history of stroke were significant. With success defined as a mRS score of 0 to 2, the shift test, stratified for the baseline severity and TFSO, showed a nonsignificant trend toward better outcomes with TLT having a probability value of 0.091 and had an OR 1.38 (95% CI, 0.95 to 2.01). For the ordinal mRS, scores 0 to 6, the shift test trended in favor of TLT with a probability value of 0.113. The odds ratios for all subsets on the primary outcome measure showed a nonsignificant trend favoring TLT treatment except for those patients with severe strokes at baseline. FIG. 36 shows the effects of TLT on the primary end point, on subsets of the data defined by categories of selected baseline characteristics. The simple unadjusted odds ratios for TLT as compared to sham for the 90-day outcome of success defined as mRS score 0 to 2. The horizontal lines indicate 95% CIs. Also shown are the probability values for the test of an interaction between the primary end point and the categories within each subgroup. CAD indicates coronary artery disease; TFSO, time from stroke onset to randomization.

For the dichotomous NIHSS score outcome for which success had 2 components, the shift test trended in favor of TLT with an OR of 1.23 (95% CI, 0.88 to 1.73) and a probability value of 0.23. Logistic regression analysis results for the dichotomous NIHSS outcome were very similar. An extension of the logistic regression analysis separated the 2 components of success, a 90-day NIHSS score of 0 to 1 and change from baseline≥9 points, and treated them as correlated outcomes: the OR was 1.30 (95% CI, 0.96 to 1.75) in favor of TLT with a probability value of 0.086. For the ordinal outcome of change in NIHSS score from baseline to 90 days, controlling for baseline severity and TFSO, the shift test indicated the TLT group and had a probability value of 0.65. In patients with deep infarcts, there was no difference in response between the active and sham groups.

Safety Analysis

Mortality rates, serious adverse event (SAE) rates, and adverse event (AE) rates were virtually the same. The TLT and sham groups, respectively, had 58 (17.5%) and 57 (17.4%) deaths, 125 (37.8%) and 137 (41.8%) SAEs; and 92.7% and 93.6% of subjects, respectively, had at least 1 adverse event. No SAEs were directly attributable to TLT. The proportion of patients in the TLT group showing hemorrhagic transformation at day 5 was 49 (14.8%) in the TLT group and 56 (17.1%) in the sham group. There was no difference in the safety outcomes between the 2 groups.

Discussion

The NEST-2 trial results presented here provide evidence of the safety of TLT. The effective size of TLT for the treatment of ischemic stroke in humans within 24 hours of stroke onset was inadequate to meet conventional levels of statistical significance for efficacy, even when the corrections were made for the baseline imbalances in stroke severity and time to treatment, but showed a consistent signal toward better outcomes associated with TLT.

Baseline severity was prespecified into 3 categories: NIHSS=7 to 10, 11 to 15, and 16 to 22. Patients with baseline NIHSS 16 to 22 had a combined dichotomous mRS success rate of 8% (n=224; TLT 7.0%, sham 9.1%). When restricted to the 434 patients with moderate and moderately severe stroke (baseline NIHSS score 7 to 15), a post hoc analysis found a significant beneficial effect (P=0.044). For these 434 patients, the dichotomous mRS success rate of TLT showed an absolute improvement rate of 9.7% (TLT 51.6%, sham 41.9%). A similar beneficial effect was also found in the NEST-1 trial on the dichotomous mRS.

The failure to initially find the optimal treatment population is reminiscent of the tPA development program. When tPA therapy was administered between 0 and 6 hours, the treated groups improved compared to the placebo ones on all measures, but the final results did not achieve statistical significance. Again, there was a strong signal of efficacy, but it was not until several trials were completed and the proper inclusion and exclusion criteria were established that the clinical benefit of tPA was unequivocally established. TLT may take additional trial(s) to find the treatment groups that are indisputably helped by the therapy. In contrast to tPA, however, TLT has no untoward side effects, so the barrier to treatment should be much lower.

There are potential weaknesses in the study that should be noted. There was insufficient previous human experience with TLT to be able to correctly power the study. The trial could have excluded patients with severe strokes at baseline and a prestroke mRS≥2. Also, it is possible that TLT does not have nay effect on stroke recovery. However, substantial preclinical studies, the NEST-1 study, and the trends in the current trial argue against this unfavorable interpretation.

A new feature of this form of therapy is that that electromagnetic energy, in the past, has been used almost exclusively for its destructive actions, such as burning out parts of solid tumors with a gamma knife, various types of radiation therapy, and both skin lesion removal and assorted ophthalmologic uses. Preclinical studies have demonstrated that infrared energy produces potential beneficial action by alteration of biochemical pathways, and that these changes are not due to thermal effects. Based on preclinical studies, it is thought that when administering TLT, the temperature of the brain is insignificantly elevated, and the energy is producing its beneficial actions by alteration of some biochemical reactions. It is known that infrared energy can stimulate mitochondria, increase ATP formation, mitigate apoptosis, and possibly enhance neurorecovery mechanisms. The precise nature and balance of these reactions in the ischemic human brain are not fully understood; therefore, the exact mechanism of action of TLT remains unknown. Nevertheless, this docs open up a whole new range of potential photobiology therapies for a variety of disorders. Brain trauma and hemorrhagic stroke are obvious extensions; it is also possible that TLT will be useful for a range of neurodegenerative diseases that may involve mitochondrial dysfunction.

CONCLUSION

The NEST-2 included a very broad range of stroke patients with respect to baseline severity, prestrike disability, and time to treatment. In this overall population, TLT was safe but did not significantly improve patient outcomes as measured by both mRS and NIHSS; however, both outcome measures showed positive trends in that direction. Post hoc analyses suggest a meaningful beneficial effect in patients with moderate to moderately severe ischemic stroke within 24 hours of onset. Further clinical studies in this redefined population should be considered.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method for irradiating multiple portions of a scalp surface with light, the method comprising:
   providing an optical element comprising a substantially optically transmissive and substantially thermally conductive material, the optical element having a first surface and a second surface;
   placing the first surface in thermal communication with the scalp surface;
   propagating the light along a first optical path through the second surface and through the first surface to a first area of the scalp surface;

propagating the light along the first optical path through the second surface and through the first surface to a second area of the scalp surface, wherein the first and second areas of the scalp surface are each at least 1 cm² and are spaced apart from each other on the scalp surface, wherein the light propagated to at least the first and second areas of the scalp surface is transmitted through intervening tissue to irradiate at least first and second areas of the patient's brain that overlap each other, and wherein a time-averaged power density of the light at the scalp surface is between about 10 mW/cm² to about 10 W/cm²;

detecting, using a sensor that is in signal communication with a logic circuit, radiation propagating along a second optical path from at least a portion of the second surface, the first optical path and the second optical path having a non-zero angle therebetween; and adjusting, by the logic circuit and responsive to the signal communication received from the sensor, one or more parameters of the propagating light.

2. The method of claim 1, wherein the first surface and the second surface face each other in generally opposite directions.

3. The method of claim 1, wherein placing the first surface in thermal communication with the surface comprises contacting the first surface to the surface.

4. The method of claim 1, wherein the first and second optical paths intersect twice.

5. The method of claim 1, wherein the adjusting the one or more parameters of the propagating light maintains the surface below a predetermined temperature level.

\* \* \* \* \*